United States Patent
Boudreaux et al.

(10) Patent No.: US 11,045,275 B2
(45) Date of Patent: Jun. 29, 2021

(54) SURGICAL INSTRUMENT WITH DUAL MODE END EFFECTOR AND SIDE-LOADED CLAMP ARM ASSEMBLY

(71) Applicant: Ethicon Endo-Surgery, LLC, Guaynabo, PR (US)

(72) Inventors: Chad P. Boudreaux, Cincinnati, OH (US); Phillip H. Clauda, Cincinnati, OH (US); John B. Schulte, West Chester, OH (US); William B. Weisenburgh, II, Maineville, OH (US); Timothy S. Holland, Cincinnati, OH (US); Ryan M. Asher, Cincinnati, OH (US); Tylor C. Muhlenkamp, Cincinnati, OH (US); Brian D. Black, Loveland, OH (US); Kristen G. Denzinger, Cincinnati, OH (US); Amy L. Benchek, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 1205 days.

(21) Appl. No.: 15/284,819

(22) Filed: Oct. 4, 2016

(65) Prior Publication Data

US 2017/0105754 A1    Apr. 20, 2017

Related U.S. Application Data

(60) Provisional application No. 62/363,411, filed on Jul. 18, 2016, provisional application No. 62/243,189, filed on Oct. 19, 2015.

(51) Int. Cl.
*A61B 90/00* (2016.01)
*A61B 18/14* (2006.01)
(Continued)

(52) U.S. Cl.
CPC .......... *A61B 90/04* (2016.02); *A61B 17/2804* (2013.01); *A61B 17/285* (2013.01);
(Continued)

(58) Field of Classification Search
CPC .... A61B 2090/0436; A61B 2090/0472; A61B 2090/0481; A61B 17/2812;
(Continued)

(56) References Cited

U.S. PATENT DOCUMENTS 5,322,055 A    6/1994  Davison et al.
5,465,894 A   11/1995  Clark et al.
(Continued)

FOREIGN PATENT DOCUMENTS

CN    1694649 A    11/2005
CN    2820104 Y     9/2006
(Continued)

OTHER PUBLICATIONS

International Search Report and Written Opinion dated Mar. 3, 2017 for Application No. PCT/US2016/057277, 18 pgs.
(Continued)

*Primary Examiner* — Ronald Hupczey, Jr.
*Assistant Examiner* — Bradford C. Blaise
(74) *Attorney, Agent, or Firm* — Frost Brown Todd LLC

(57) ABSTRACT

A surgical instrument includes a body, an ultrasonic blade, a clamp arm, and a resilient member. The body includes an electrical conductor and defines a longitudinal axis. The clamp arm is pivotably coupled with the body at a pivot assembly. The clamp arm is operable to compress tissue against the ultrasonic blade. The clamp arm includes an electrode operable to apply RF energy to tissue, wherein the clamp arm is configured to be loaded onto and removed from the body at the pivot assembly along a path that is transverse to the longitudinal axis defined by the body. The resilient
(Continued)

member is located within the pivot assembly. The resilient member is configured to provide electrical continuity between the electrode of the clamp arm and the electrical conductor of the body.

20 Claims, 63 Drawing Sheets

(51) Int. Cl.
  *A61B 17/28* (2006.01)
  *A61B 17/285* (2006.01)
  *A61B 17/29* (2006.01)
  *A61B 17/295* (2006.01)
  *A61B 17/32* (2006.01)
  *A61B 18/00* (2006.01)
  *A61B 17/00* (2006.01)

(52) U.S. Cl.
  CPC ...... *A61B 17/2812* (2013.01); *A61B 17/2816* (2013.01); *A61B 17/2833* (2013.01); *A61B 17/2841* (2013.01); *A61B 17/29* (2013.01); *A61B 17/295* (2013.01); *A61B 17/320092* (2013.01); *A61B 18/14* (2013.01); *A61B 18/1442* (2013.01); *A61B 18/1445* (2013.01); *A61B 90/03* (2016.02); *A61B 2017/00022* (2013.01); *A61B 2017/00026* (2013.01); *A61B 2017/0046* (2013.01); *A61B 2017/00119* (2013.01); *A61B 2017/00123* (2013.01); *A61B 2017/00128* (2013.01); *A61B 2017/00464* (2013.01); *A61B 2017/00477* (2013.01); *A61B 2017/00778* (2013.01); *A61B 2017/00818* (2013.01); *A61B 2017/2825* (2013.01); *A61B 2017/2829* (2013.01); *A61B 2017/2931* (2013.01); *A61B 2017/2933* (2013.01); *A61B 2017/2939* (2013.01); *A61B 2017/2944* (2013.01); *A61B 2017/2946* (2013.01); *A61B 2017/2947* (2013.01); *A61B 2017/320093* (2017.08); *A61B 2017/320094* (2017.08); *A61B 2017/320095* (2017.08); *A61B 2018/0019* (2013.01); *A61B 2018/0063* (2013.01); *A61B 2018/0094* (2013.01); *A61B 2018/00178* (2013.01); *A61B 2018/00297* (2013.01); *A61B 2018/00309* (2013.01); *A61B 2018/00345* (2013.01); *A61B 2018/00529* (2013.01); *A61B 2018/00589* (2013.01); *A61B 2018/00601* (2013.01); *A61B 2018/00702* (2013.01); *A61B 2018/00708* (2013.01); *A61B 2018/00767* (2013.01); *A61B 2018/00875* (2013.01); *A61B 2018/00892* (2013.01); *A61B 2018/00898* (2013.01); *A61B 2018/00916* (2013.01); *A61B 2018/00922* (2013.01); *A61B 2018/00928* (2013.01); *A61B 2018/00958* (2013.01); *A61B 2018/00988* (2013.01); *A61B 2018/00994* (2013.01); *A61B 2018/1405* (2013.01); *A61B 2018/146* (2013.01); *A61B 2018/1455* (2013.01); *A61B 2018/1467* (2013.01); *A61B 2090/035* (2016.02); *A61B 2090/036* (2016.02); *A61B 2090/0427* (2016.02); *A61B 2090/0436* (2016.02); *A61B 2090/0472* (2016.02); *A61B 2090/0481* (2016.02); *A61B 2090/064* (2016.02); *A61B 2090/0803* (2016.02); *A61B 2090/0808* (2016.02); *A61B 2090/0811* (2016.02); *A61B 2090/0812* (2016.02); *A61B 2090/0813* (2016.02); *A61B 2090/0814* (2016.02)

(58) Field of Classification Search
  CPC .............. A61B 17/2816; A61B 17/282; A61B 17/2841; A61B 2017/0046; A61B 2017/00464; A61B 2017/00477; A61B 2017/00482; A61B 2017/320093; A61B 2017/320094; A61B 2017/320095; A61B 2017/00119; A61B 2017/00123; A61B 2017/00128; A61B 2017/00367; A61B 2017/00371; A61B 2017/00376; A61B 2017/0038; A61B 2017/00384; A61B 2018/0019; A61B 2018/00898; A61B 2018/00958; A61B 2018/00988; A61B 2018/00994; A61B 17/320068; A61B 17/320092
  See application file for complete search history.

(56) References Cited

U.S. PATENT DOCUMENTS

| | | | |
|---|---|---|---|
| 5,556,404 A * | 9/1996 | Belanger | A61B 17/282 425/427 |
| 5,607,094 A | 3/1997 | Clark et al. | |
| 5,797,939 A | 8/1998 | Yoon | |
| 5,827,299 A | 10/1998 | Thomason et al. | |
| 5,873,873 A | 2/1999 | Smith et al. | |
| 5,980,510 A | 11/1999 | Tsonton et al. | |
| 6,325,811 B1 | 12/2001 | Messerly | |
| 6,454,781 B1 | 9/2002 | Witt et al. | |
| 6,773,444 B2 | 8/2004 | Messerly | |
| 6,783,524 B2 | 8/2004 | Anderson et al. | |
| 7,267,677 B2 | 9/2007 | Johnson et al. | |
| 7,563,269 B2 | 7/2009 | Hashiguchi | |
| 8,461,744 B2 | 6/2013 | Wiener et al. | |
| 8,591,536 B2 | 11/2013 | Robertson | |
| 8,623,027 B2 | 1/2014 | Price et al. | |
| 8,845,667 B2 | 9/2014 | Cruz Hernandez et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,375,255 B2 | 6/2016 | Houser et al. | |
| 9,381,058 B2 | 7/2016 | Houser et al. | |
| 9,393,037 B2 | 7/2016 | Olson et al. | |
| 9,610,115 B2 | 4/2017 | Rothweiler et al. | |
| 10,004,528 B2 | 6/2018 | Faller et al. | |
| 2004/0093020 A1 * | 5/2004 | Sinton | A61B 17/2816 606/208 |
| 2005/0192612 A1 | 9/2005 | Houser et al. | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0255130 A1 | 10/2009 | Jalmberger | |
| 2009/0261804 A1 * | 10/2009 | McKenna | A61B 18/1442 324/71.1 |
| 2009/0299367 A1 | 12/2009 | Ginnebaugh et al. | |
| 2010/0063525 A1 | 3/2010 | Beaupre et al. | |
| 2010/0331873 A1 | 12/2010 | Dannaher et al. | |
| 2011/0290853 A1 | 12/2011 | Shelton, IV et al. | |
| 2012/0116265 A1 | 5/2012 | Houser et al. | |
| 2012/0116391 A1 * | 5/2012 | Houser | A61B 18/1442 606/41 |
| 2012/0245582 A1 * | 9/2012 | Kimball | A61B 17/320092 606/41 |
| 2013/0110155 A1 * | 5/2013 | Tsuchiya | A61B 17/2816 606/205 |
| 2013/0303949 A1 * | 11/2013 | Kawaguchi | A61B 17/282 601/2 |
| 2013/0338660 A1 * | 12/2013 | Rothweiler | A61B 18/1442 606/33 |
| 2013/0345732 A1 | 12/2013 | Dannaher et al. | |
| 2014/0066911 A1 * | 3/2014 | Nau, Jr. | A61B 18/22 606/8 |
| 2014/0135804 A1 | 5/2014 | Weisenburgh et al. | |
| 2014/0330298 A1 | 11/2014 | Arshonsky et al. | |

(56) References Cited

U.S. PATENT DOCUMENTS

| | | | |
|---|---|---|---|
| 2015/0080924 A1 | 3/2015 | Stulen et al. | |
| 2015/0080925 A1 | 3/2015 | Schulte et al. | |
| 2015/0148833 A1 | 5/2015 | Stokes et al. | |
| 2015/0196782 A1 | 7/2015 | Akagane | |
| 2015/0305796 A1* | 10/2015 | Wang | A61B 18/1445 606/52 |
| 2015/0313667 A1 | 11/2015 | Allen, IV | |
| 2015/0342583 A1 | 12/2015 | Van De Weghe et al. | |
| 2016/0045770 A1* | 2/2016 | Yamada | A61B 18/1445 601/2 |
| 2016/0199121 A1* | 7/2016 | Kase | A61B 17/320092 606/41 |

FOREIGN PATENT DOCUMENTS

| | | |
|---|---|---|
| CN | 101820825 A | 9/2010 |
| CN | 103561664 A | 2/2014 |
| CN | 104271051 A | 1/2015 |
| DE | 298 11 977 U1 | 10/1998 |
| EP | 1769765 A1 | 4/2007 |
| EP | 2 436 328 A1 | 4/2012 |
| EP | 2 589 347 A1 | 5/2013 |
| JP | 2005-176905 A | 7/2005 |
| JP | 2010-264258 A | 11/2010 |
| JP | 2014-226318 A | 12/2014 |
| WO | WO 02/080798 A1 | 10/2002 |
| WO | WO 2009/149799 A1 | 12/2009 |
| WO | WO 2013/154923 A2 | 10/2013 |
| WO | WO 2013/115036 A1 | 5/2015 |
| WO | WO 2015/107916 A1 | 7/2015 |
| WO | WO 2016/044277 A1 | 3/2016 |

OTHER PUBLICATIONS

International Search Report and Written Opinion dated Mar. 30, 2017 for Application No. PCT/US2016/057280, 19 pgs.
International Search Report and Written Opinion dated Feb. 6, 2017 for Application No. PCT/US2016/057288, 14 pgs.
U.S. Appl. No. 61/410,603, filed Nov. 5, 2010.
U.S. Appl. No. 62/243,189, filed Oct. 19, 2015.
U.S. Appl. No. 62/363,411, filed Jul. 18, 2016.
U.S. Appl. No. 15/284,837, filed Oct. 4, 2016.
U.S. Appl. No. 15/284,855, filed Oct. 4, 2016.
U.S. Appl. No. 15/284,837.
U.S. Appl. No. 15/284,855.
European Search Report and Written Opinion, Under Rule 164(2)(b) EPC, dated Oct. 29, 2019 for Application No. EP 16784766.4, 11 pgs.
European Examination Report dated Aug. 1, 2019 for Application No. EP 16798019.2, 5 pgs.
European Search Report, Partial, and Provisional Written Opinion dated Aug. 2, 2019 for Application No. EP 19185531.1, 13 pgs.
European Search Report and Written Opinion dated Nov. 4, 2019 for Application No. EP 19185531.1, 12 pgs.
European Search Report, Partial, and Provisional Written Opinion dated Aug. 5, 2019 for Application No. EP 19185541.0, 12 pgs.
European Search Report and Written Opinion dated Oct. 30, 2019 for Application No. EP 19185541.0, 14 pgs.
Chinese Office Action dated May 27, 2020 for Application No. 201680061293.1, 14 pages.
Chinese Office Action, The First Office Action, and First Search, dated Jun. 2, 2020, for Application No. CN 201680061050.8, 18 pgs.
Chinese Office Action, The First Office Action, and First Search, dated Jun. 2, 2020, for Application No. CN 201680061406.8, 20 pgs.
European Examination Report dated Aug. 2, 2019 for Application No. EP 16784766.4, 7 pgs.
Japanese Office Action, Notice of Reasons for Refusal, Search Report by Registered Search Organization, dated Oct. 6, 2020 for Application No. JP 2018-539244, 23 pgs.
Japanese Office Action, Notice of Reasons for Refusal, Search Report by Registered Search Organization, dated Oct. 6, 2020 for Application No. JP 2018-539245, 22 pgs.
Japanese Office Action, Notice of Reasons for Refusal, Search Report by Registered Search Organization, dated Oct. 6, 2020 for Application No. JP 2018-539246, 22 pgs.

* cited by examiner

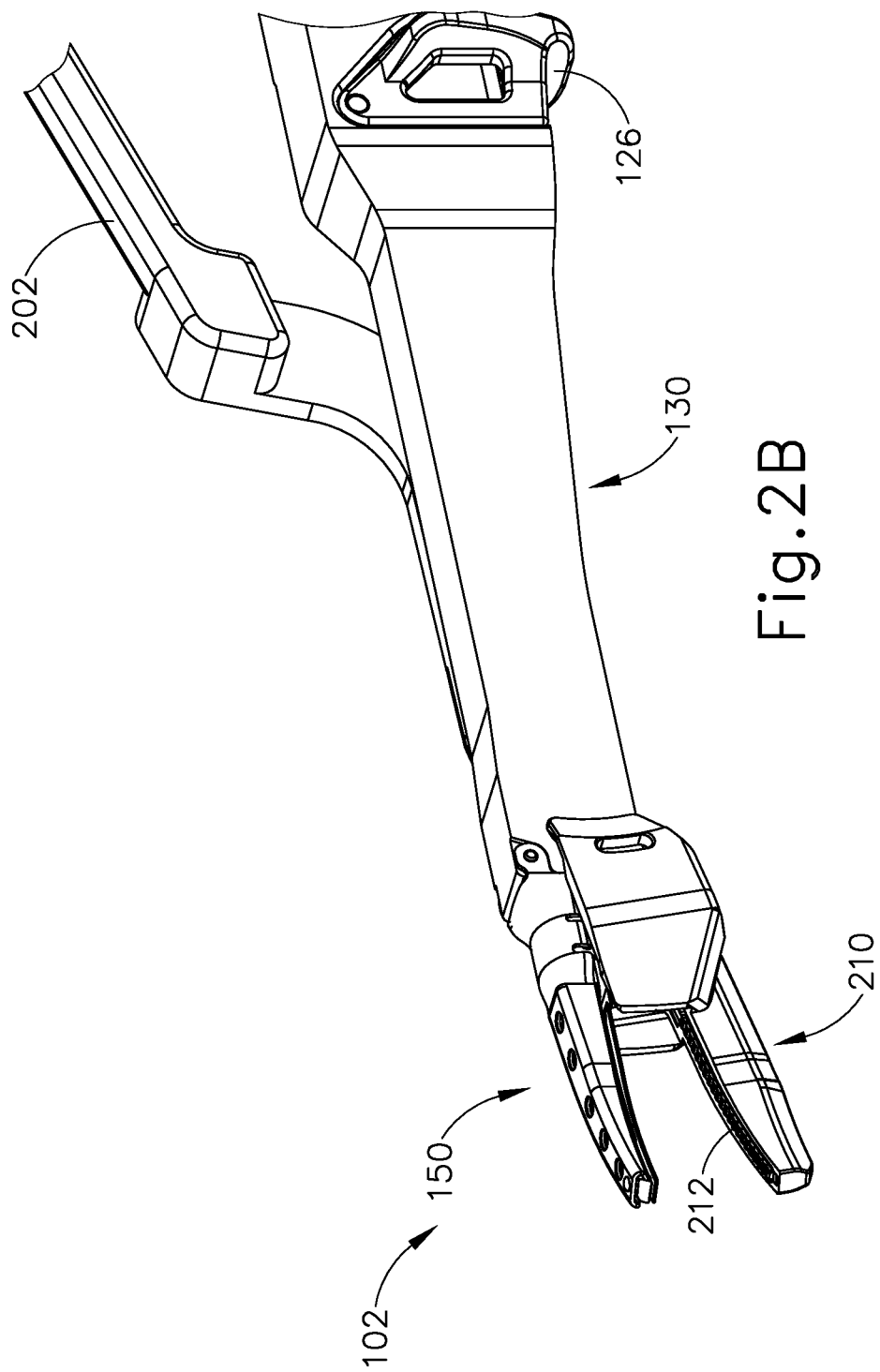

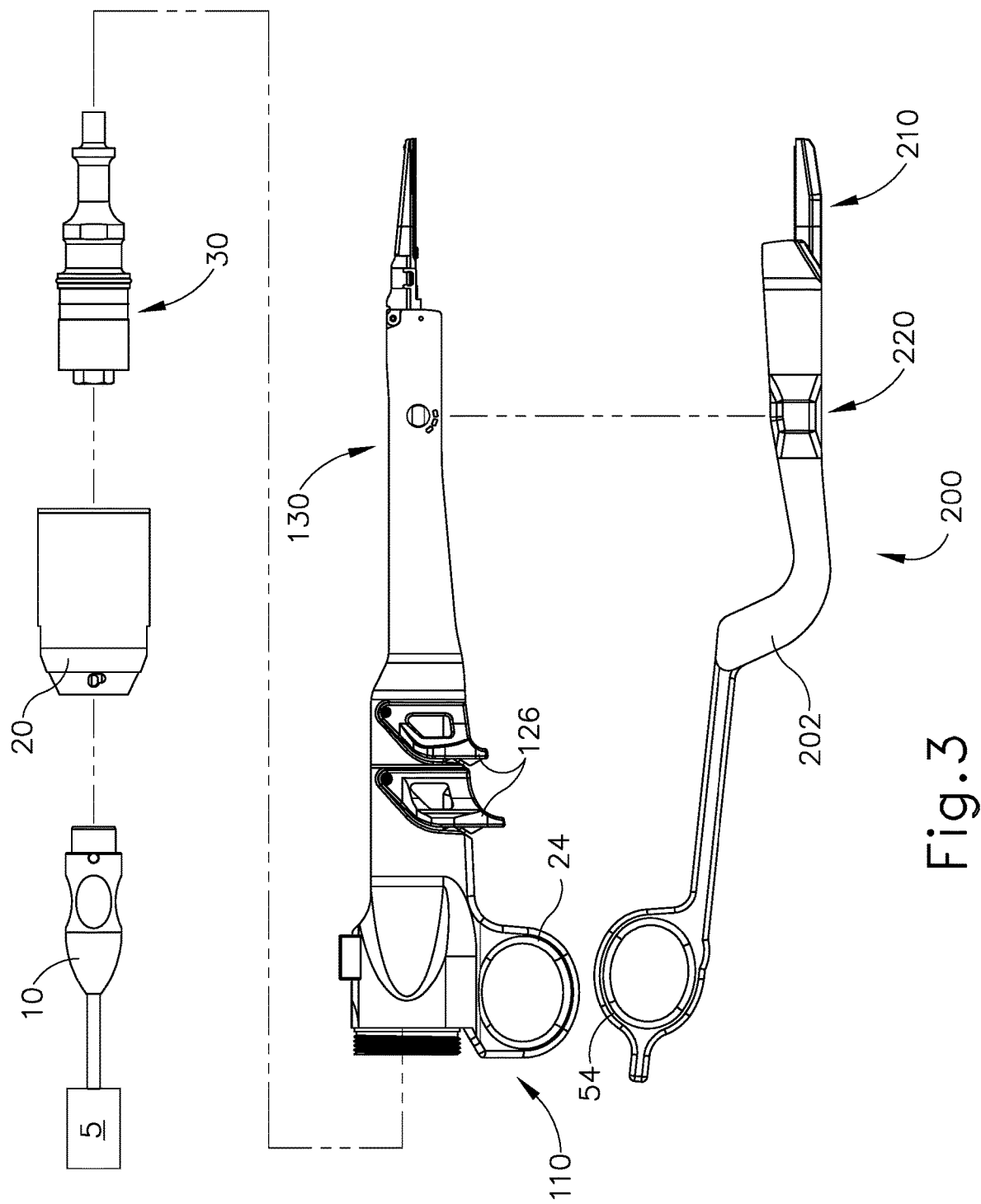

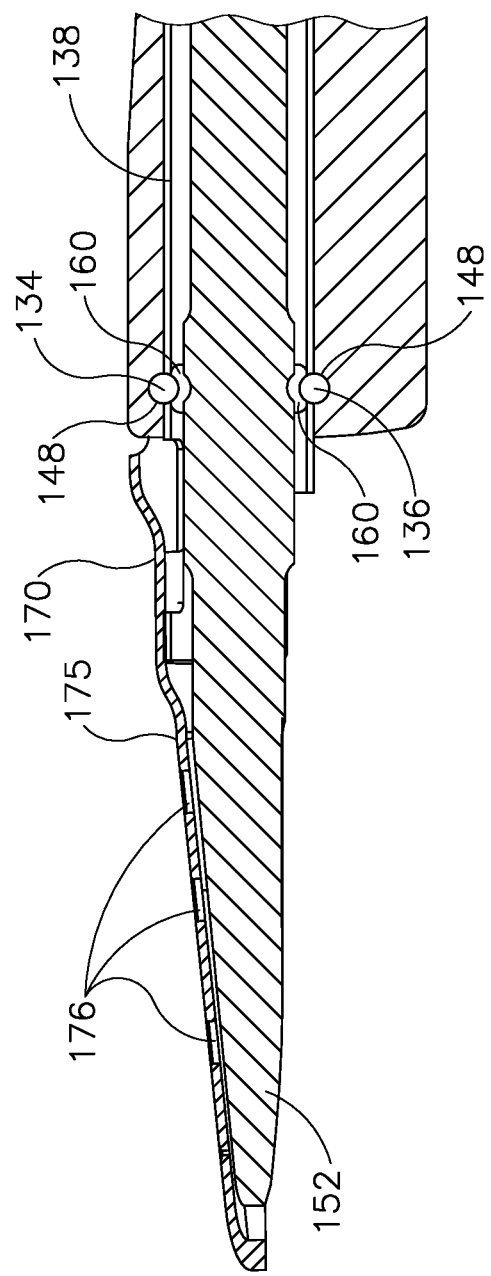

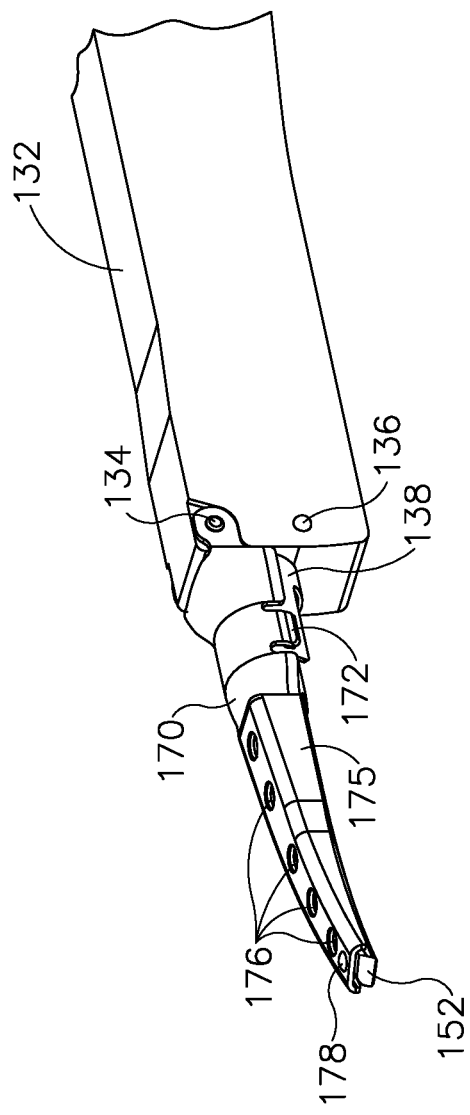

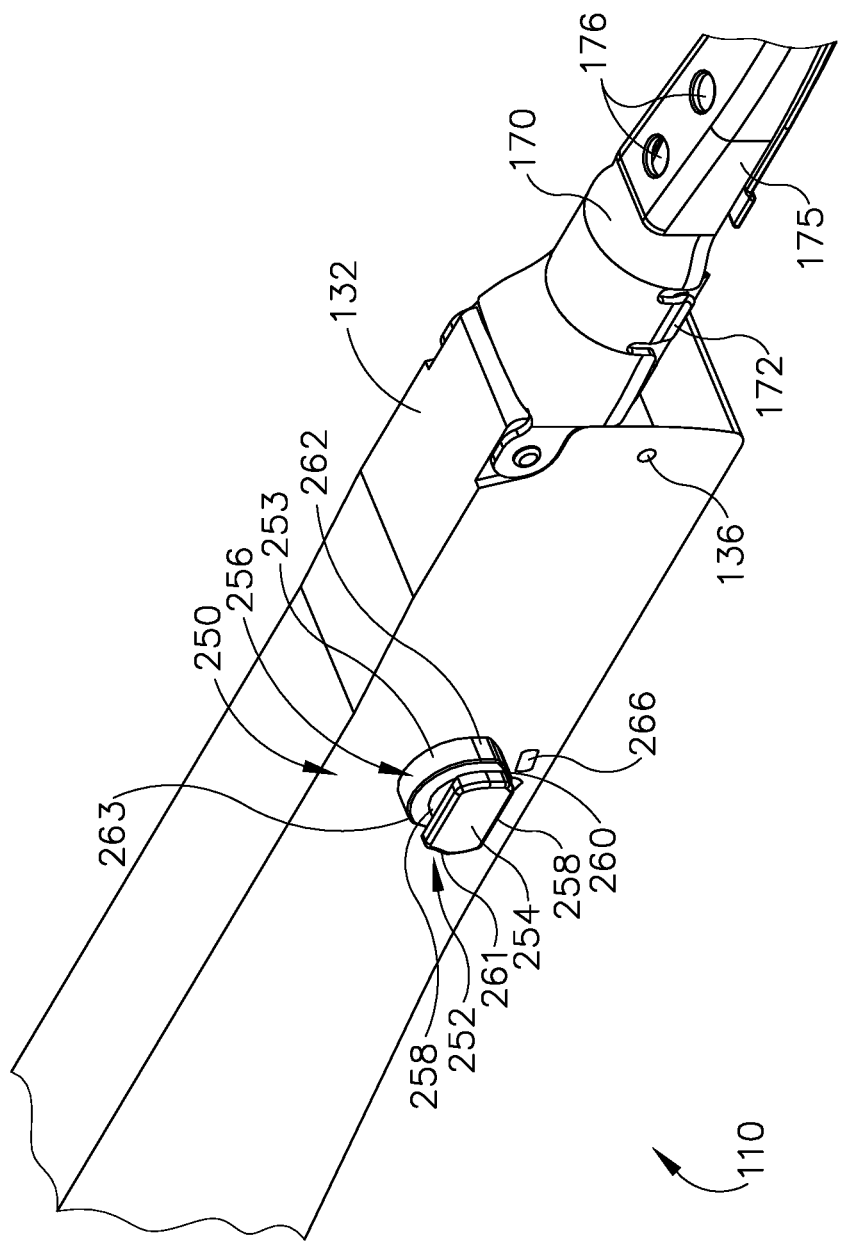

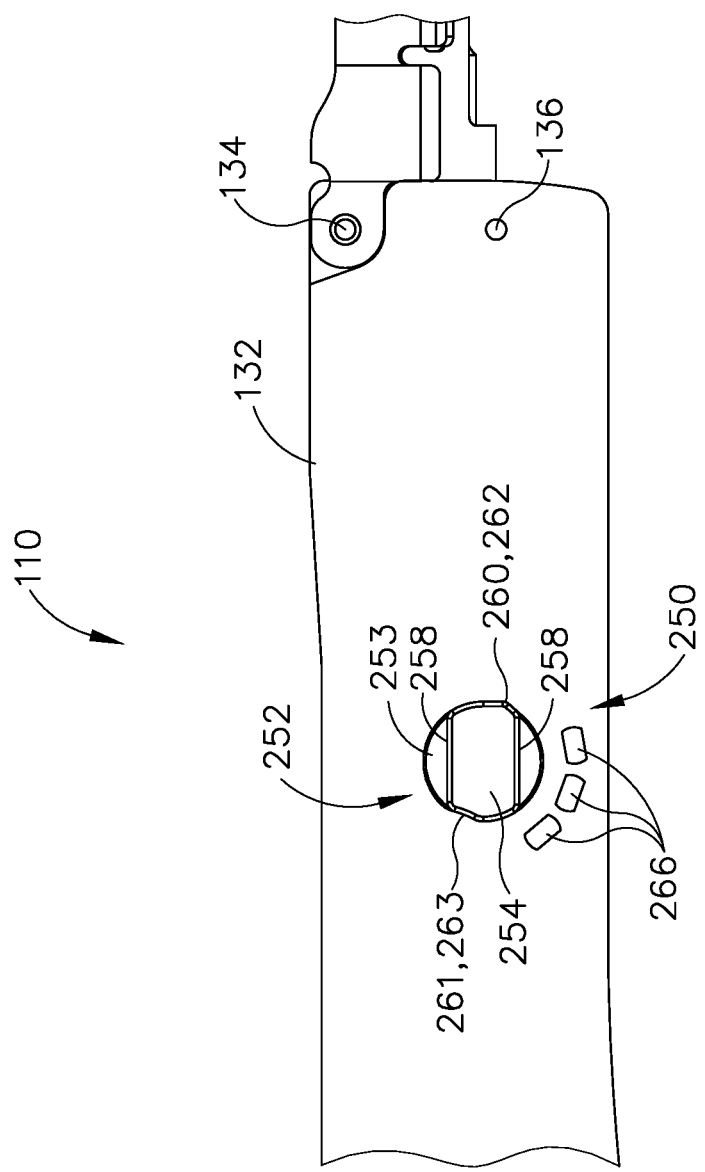

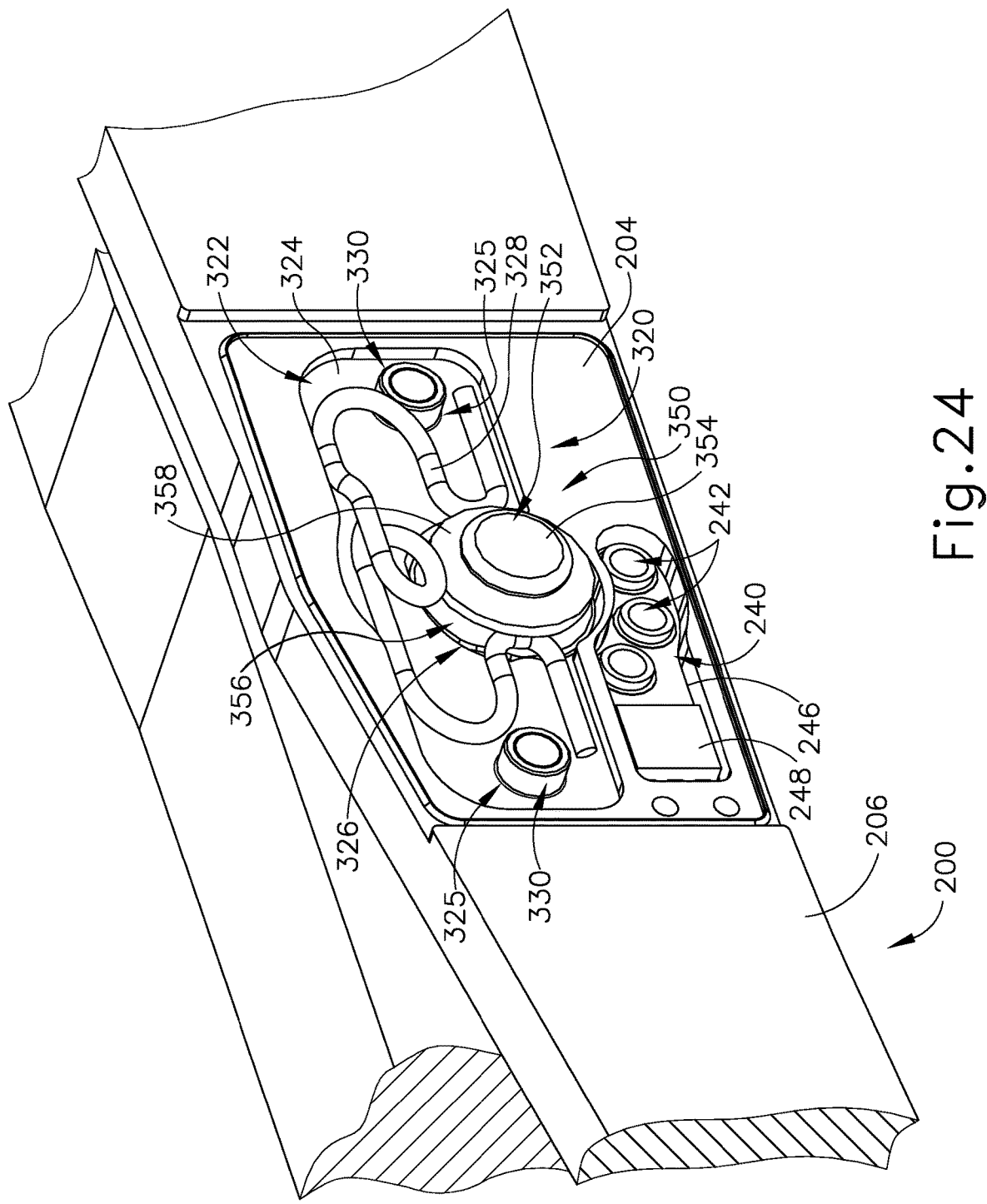

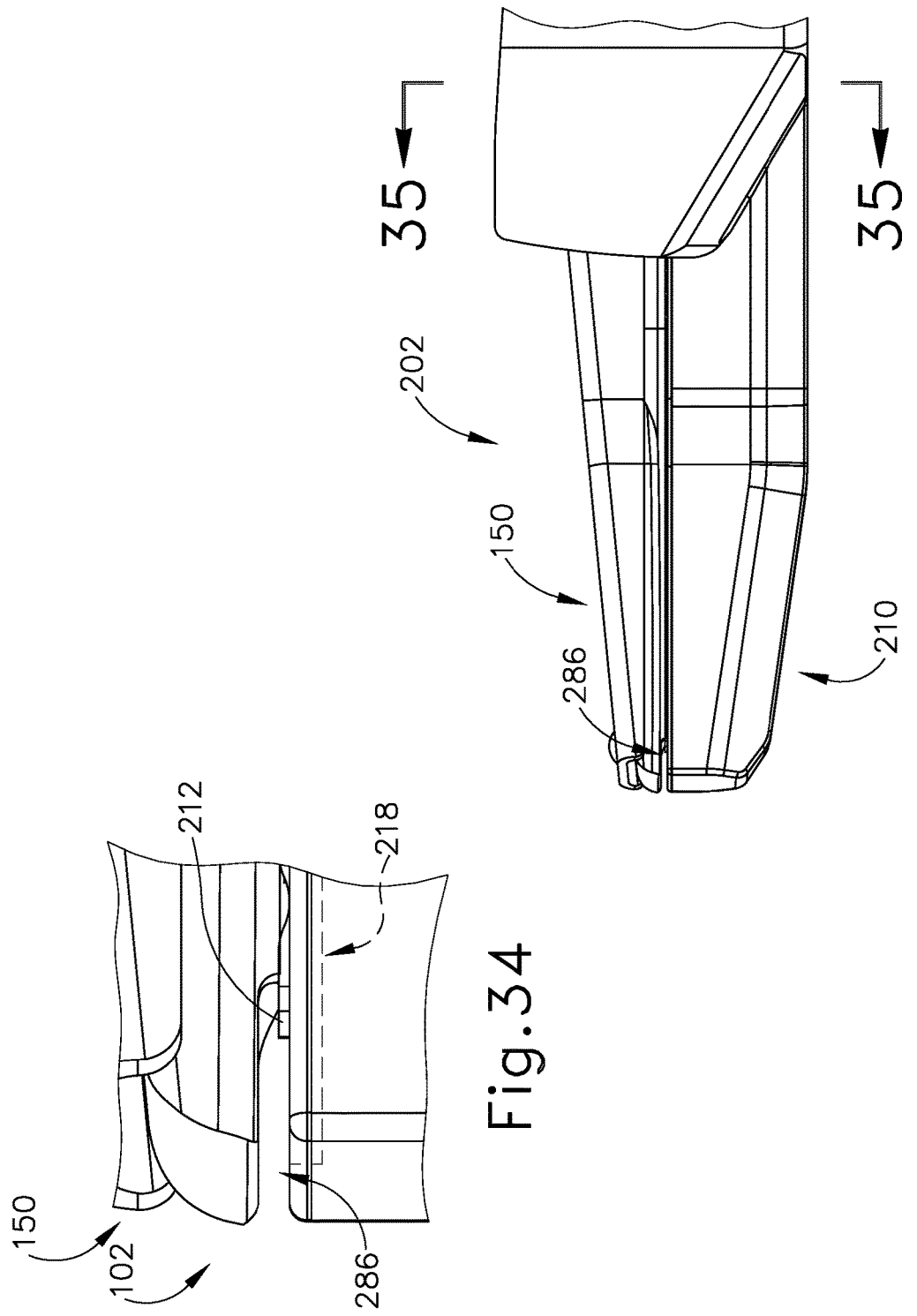

SURGICAL INSTRUMENT WITH DUAL MODE END EFFECTOR AND SIDE-LOADED CLAMP ARM ASSEMBLY

PRIORITY

This application claims priority to U.S. Provisional Patent App. No. 62/363,411, entitled "Surgical Instrument with Dual Mode End Effector," filed Jul. 18, 2016, the disclosure of which is incorporated by reference herein.

This application also claims priority to U.S. Provisional Patent App. No. 62/243,189, entitled "Surgical Instrument with Dual Mode End Effector," filed Oct. 19, 2015, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein, U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, entitled "Surgical Instruments with Articulating Shafts," published Jan. 2, 2014, issued as U.S. Pat. No. 9,393,037 on Jul. 19, 2016, the disclosure of which is incorporated by reference herein; and U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 2B depicts an enlarged perspective view of the end effector of FIG. 1A in an open configuration;

FIG. 3 depicts an exploded view of the instrument of FIG. 1A;

FIG. 7 depicts a cross-sectional side view of the ultrasonic blade of FIG. 6 and the heat shield of FIG. 5;

FIG. 8B depicts a perspective view of the ultrasonic blade of FIG. 6 and the heat shield of FIG. 5, with the heat shield pivoted to a downward position;

FIG. 17 depicts an enlarged perspective view of coupling components of the handle assembly of FIG. 4;

FIG. 18 depicts a side elevational view of the coupling components of FIG. 17;

FIG. 24 depicts a perspective view of an exemplary alternative coupling assembly incorporated into the instrument of FIG. 1A;

FIG. 33 depicts a side elevational view of the end effector of FIG. 1A, with the end effector in a closed configuration;

FIG. 34 depicts an enlarged side elevational view of the distal end of the end effector of FIG. 1A, with the end effector in a closed configuration;

Figure 1A:
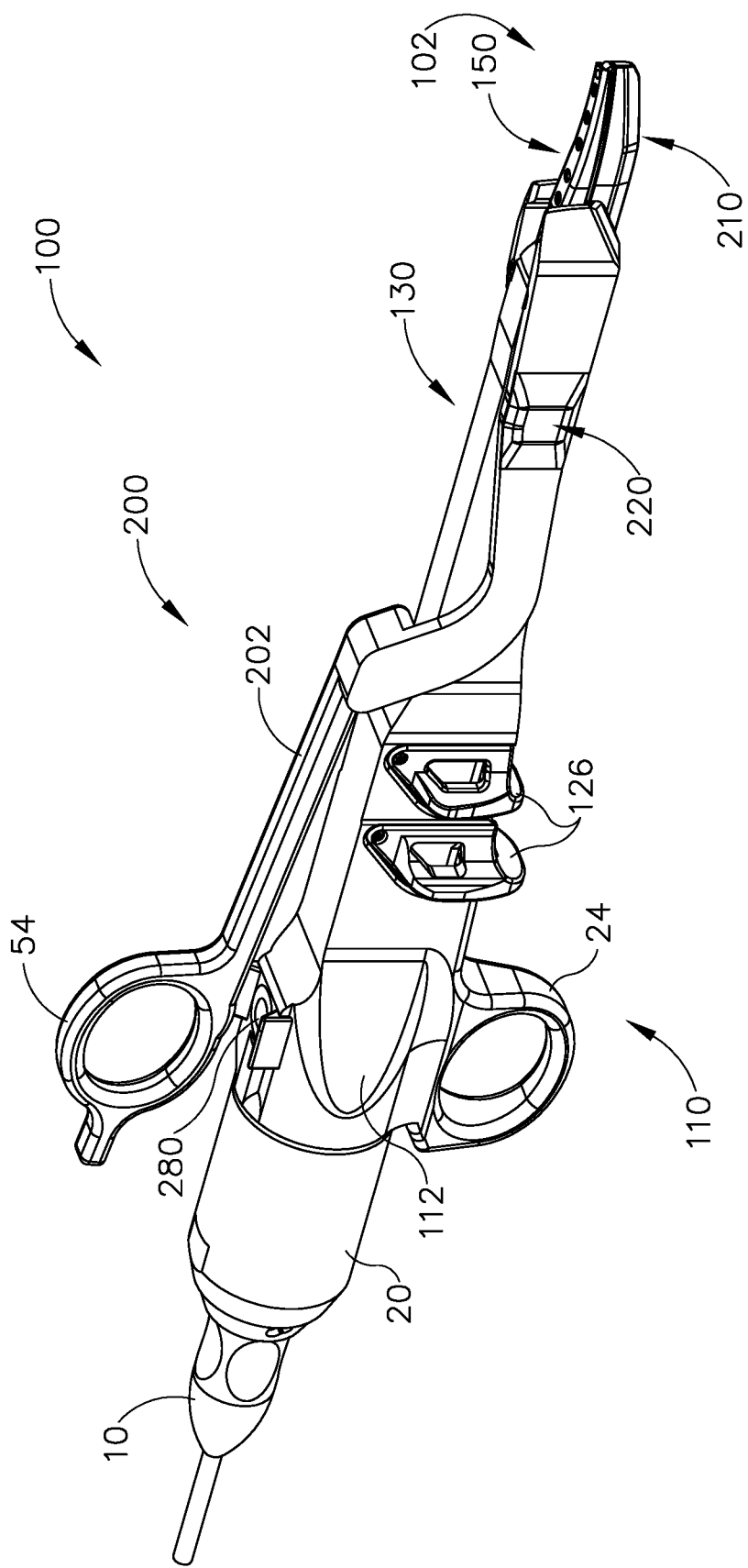
FIG. 1A depicts a perspective view of an exemplary surgical instrument, with an end effector of the instrument in a closed configuration.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument for Open Surgical Procedures

A. Overview

FIGS. 1A-3 illustrate exemplary ultrasonic surgical instrument (100). At least part of instrument (100) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, issued as U.S. Pat. No. 8,623,027 on Jan. 7, 2014; U.S. Pub. No. 2010/0069940, issued as U.S. Pat. No. 9,023,071 on May 5, 2014; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; U.S. Pat. App. No. 61/410,603; and/or U.S. patent application Ser. No. 14/028,717, issued as U.S. Pat. No. 10,172,636 on Jan. 8, 2019. The disclosures of each of the foregoing patents, publications, and applications are incorporated by reference herein. As described therein and as will be described in greater detail below, instrument (100) is operable to cut tissue and seal or weld tissue (e.g., a blood vessel, etc.) substantially simultaneously. It should also be understood that instrument (100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (100) of the present example comprises a plug (10), a proximal casing (20), handle assembly (110), a shaft assembly (130), a blade assembly (150), a clamp arm assembly (200), and an end effector (102). As will be described in greater detail below, clamp arm assembly (200) may be selectively attached to handle assembly (110) and detached from handle assembly (110). The ability to selectively attach and detach clamp arm assembly (200) from handle assembly (110) may provide additional benefits of reusability for either handle assembly (110) or clamp arm assembly (200).

Handle assembly (110) comprises a body (112) including a finger grip ring (24), a button (280) on top of body (112), and a pair of buttons (126) distal to finger grip ring (24). Instrument (100) also includes a clamp arm assembly (200) that is pivotable toward and away from body (122). Clamp arm assembly (200) includes a body (202) with a thumb grip ring (54). Thumb grip ring (54) and finger grip ring (24) together provide a scissor grip type of configuration. It should be understood, however, that various other suitable configurations may be used, including but not limited to a pistol grip configuration.

Figure 2A:
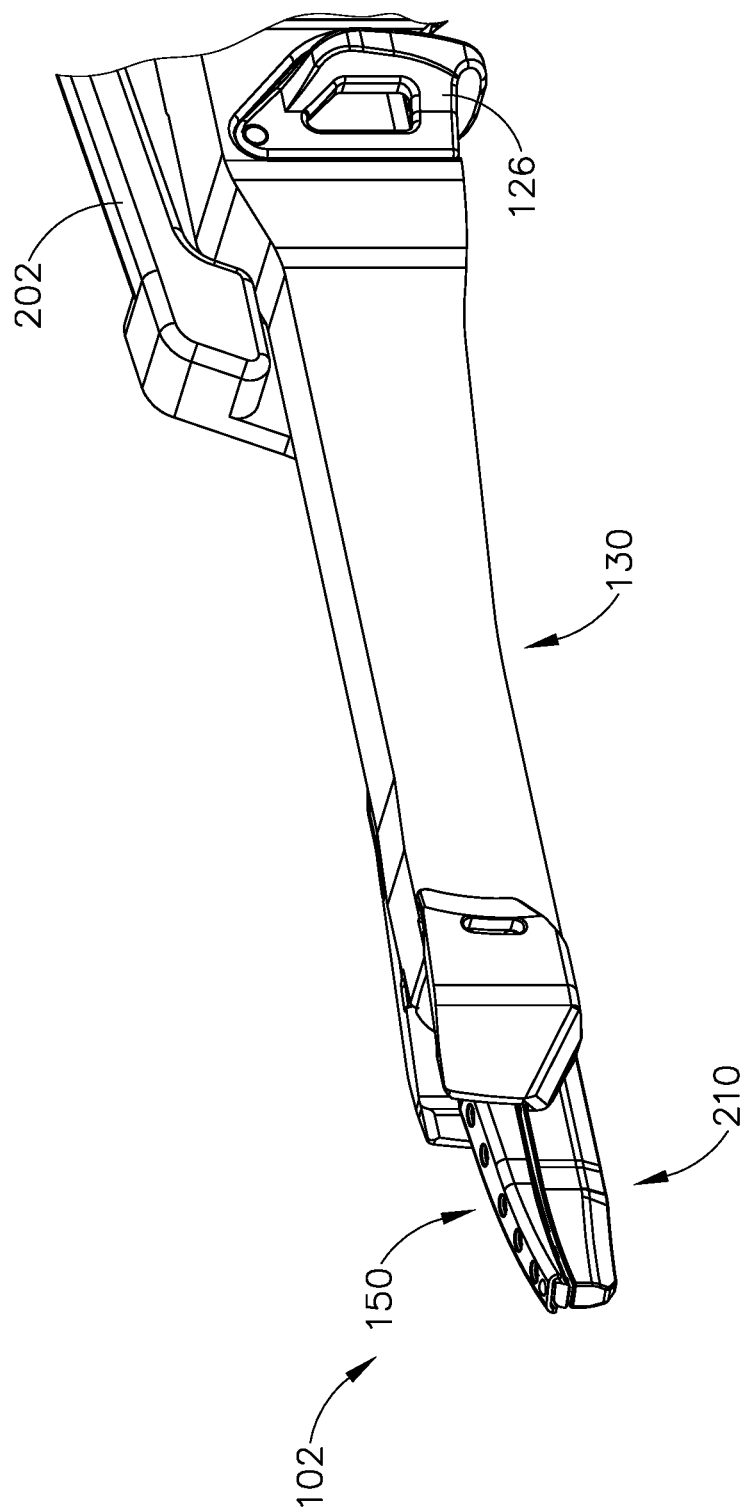
FIG. 2A depicts an enlarged perspective view of the end effector of FIG. 1A in a closed configuration.

Shaft assembly (130) comprises an outer sheath (132) extending distally from body (112). As best seen in FIGS. 2A-2B, end effector (102) comprises an ultrasonic blade (152) and a clamp pad assembly (210). End effector (102) is operable to transition between a closed position, as shown in FIG. 2A, and an open position, as show in FIG. 2B. Ultrasonic blade (152) extends distally from outer sheath (132). As will be described in greater detail below, ultrasonic blade (152) is a part of blade assembly (150).

Clamp pad assembly (210) is an integral feature of clamp arm assembly (200). Clamp pad assembly (210) includes a clamp pad (212) facing ultrasonic blade (152). Clamp pad assembly (210) is pivotally coupled with outer sheath (132) via a coupling assembly (220). Clamp pad assembly (210) is positioned distal to coupling assembly (220); while body (202) and thumb grip ring (154) are positioned proximal to coupling assembly (220). Thus, as shown in FIGS. 1A-2B, clamp pad assembly (210) is pivotable toward and away from ultrasonic blade (152) based on pivoting of thumb grip ring (54) toward and away from body (112) of handle assembly (110). It should therefore be understood that an operator may squeeze thumb grip ring (54) toward body (112) to thereby clamp tissue between clamp pad assembly (210) and ultrasonic blade (152) to compress tissue against ultrasonic blade (152). When ultrasonic blade (152) is activated during such compression, clamp pad assembly (210) and ultrasonic blade (152) cooperate to transect and/or seal the compressed tissue. In some versions, one or more resilient members are used to bias clamp pad assembly (210) to the open position shown in FIGS. 1B and 2B. By way of example only, such a resilient member may comprise a leaf spring, a torsion spring, and/or any other suitable kind of resilient member.

Referring to FIG. 3, an ultrasonic transducer assembly (30) is housed within proximal casing (20) and body (112) of handle assembly (110). Transducer assembly (30) is coupled with a generator (5) via a plug (10). Transducer assembly (30) receives electrical power from generator (5) and converts that power into ultrasonic vibrations through piezoelectric principles. Generator (5) may include a power source and control module that is configured to provide a power profile to transducer assembly (30) that is particularly suited for the generation of ultrasonic vibrations through transducer assembly (30). Generator (5) may also be configured to provide a power profile that enables end effector (102) to apply RF electrosurgical energy to tissue.

By way of example only, generator (5) may comprise a GEN 300 sold by Ethicon Endo-Surgery, Inc. of Cincinnati, Ohio. In addition or in the alternative, generator (not shown) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (5) may be integrated into handle assembly (110), and that handle assembly (110) may even include a battery or other on-board power source such that plug (10) is omitted. Still other suitable forms that generator (5) may take, as well as various features and operabilities that generator (5) may provide, will be apparent to those of ordinary skill in the art in view of the teachings herein.

Ultrasonic vibrations that are generated by transducer assembly (30) are communicated along an acoustic waveguide (154). Waveguide (154) is mechanically and acoustically coupled with transducer assembly (30). Waveguide (154) extends through shaft assembly (130) to reach ultrasonic blade (152). Waveguide (154) is secured within shaft assembly (130) via locator pins (134, 136), which will be described in greater detail below. Pins (134, 136) are located at a position along the length of waveguide (154) corresponding to a node associated with resonant ultrasonic vibrations communicated through waveguide (154). As noted above, when ultrasonic blade (152) is in an activated state (i.e., vibrating ultrasonically), ultrasonic blade (152) is operable to effectively cut through and seal tissue, particularly when the tissue is being clamped between clamp pad (212) and ultrasonic blade 152. It should be understood that waveguide (154) may be configured to amplify mechanical vibrations transmitted through waveguide (154). Furthermore, waveguide (154) may include features operable to control the gain of the longitudinal vibrations along waveguide (154) and/or features to tune waveguide (154) to the resonant frequency of the system.

In the present example, the distal end of ultrasonic blade (152) is located at a position corresponding to an anti-node associated with resonant ultrasonic vibrations communicated through waveguide (154), in order to tune the acoustic assembly to a preferred resonant frequency $f_o$ when the acoustic assembly is not loaded by tissue. When transducer assembly (30) is energized, the distal end of ultrasonic blade (152) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (30) of the present example is activated, these mechanical oscillations are transmitted through the waveguide to reach ultrasonic blade (152), thereby providing oscillation of ultrasonic blade (152) at the resonant ultrasonic frequency. Thus, when tissue is secured between ultrasonic blade (152) and clamp pad (212), the ultrasonic oscillation of ultrasonic blade (152) may simultaneously sever the tissue and denature the proteins in adjacent tissue cells, thereby providing a coagulative effect with relatively little thermal spread. In some versions, an electrical current may also be provided through ultrasonic blade (152) and/or clamp pad (212) to also seal the tissue.

As will be described in greater detail below, instrument (100) is also configured to provide radiofrequency (RF) energy to a surgical site via end effector (102). By way of example only, an operator may rely mainly on the use of ultrasonic energy from blade (152) to sever tissue that is captured between ultrasonic blade (152) and clamp pad (212). The operator may further rely on the use of RF energy from end effector (102) to seal the severed tissue. Of course, it will be understood that the ultrasonic energy from blade (152) may seal tissue to some degree, such that the RF energy from end effector (102) may supplement the sealing that would already be provided from the ultrasonic energy. It will also be understood that there may be instances where the operator may wish to simply wish to use end effector (102) to only apply RF energy to tissue, without also applying ultrasonic energy to tissue. As will be appreciated from the description herein, some versions of instrument (100) are capable of providing all of the above noted kinds of functionality.

An operator may activate buttons (126) to selectively activate transducer assembly (30) to thereby activate ultrasonic blade (152). In the present example, two buttons (126) are provided. In some versions, one button (126) is provided for activating ultrasonic blade (152) at a first power profile (e.g., a first frequency and/or first amplitude) and another button (126) is provided for activating ultrasonic blade (152) at a second power profile (e.g., a second frequency and/or second amplitude). In some other versions, one button (126) is provided for activating ultrasonic blade (152) with ultrasonic energy, and the other button (126) is provided for activating end effector (102) with RF energy. It should be understood that any other suitable number of buttons and/or otherwise selectable power levels and/or power modalities may be provided. For instance, a foot pedal may be provided to selectively activate transducer assembly (30).

Buttons (126) of the present example are positioned such that an operator may readily fully operate instrument (100) with a single hand. For instance, the operator may position their thumb in thumb grip ring (54), position their ring finger in finger grip ring (124), position their middle finger about body (112), and manipulate buttons (126) using their index finger. Of course, any other suitable techniques may be used to grip and operate instrument (100); and buttons (126) may be located at any other suitable positions.

The foregoing components and operabilities of instrument (100) are merely illustrative. Instrument (100) may be configured in numerous other ways as will be apparent to those of ordinary skill in the art in view of the teachings herein. By way of example only, at least part of instrument (100) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; and/or U.S. Pub. No. 2015/0080925, entitled "Alignment Features for Ultrasonic Surgical Instrument," published Mar. 19, 2015, now abandoned, the disclosure of which is incorporated by reference herein. Additional merely illustrative features and variations for instrument (100) will be described in greater detail below. It should be understood that the below described variations may be readily incorporated into to instrument (100) described above and into any of the instruments described in any of the references that are cited herein, among others.

B. Exemplary Blade Assembly

Figure 4:
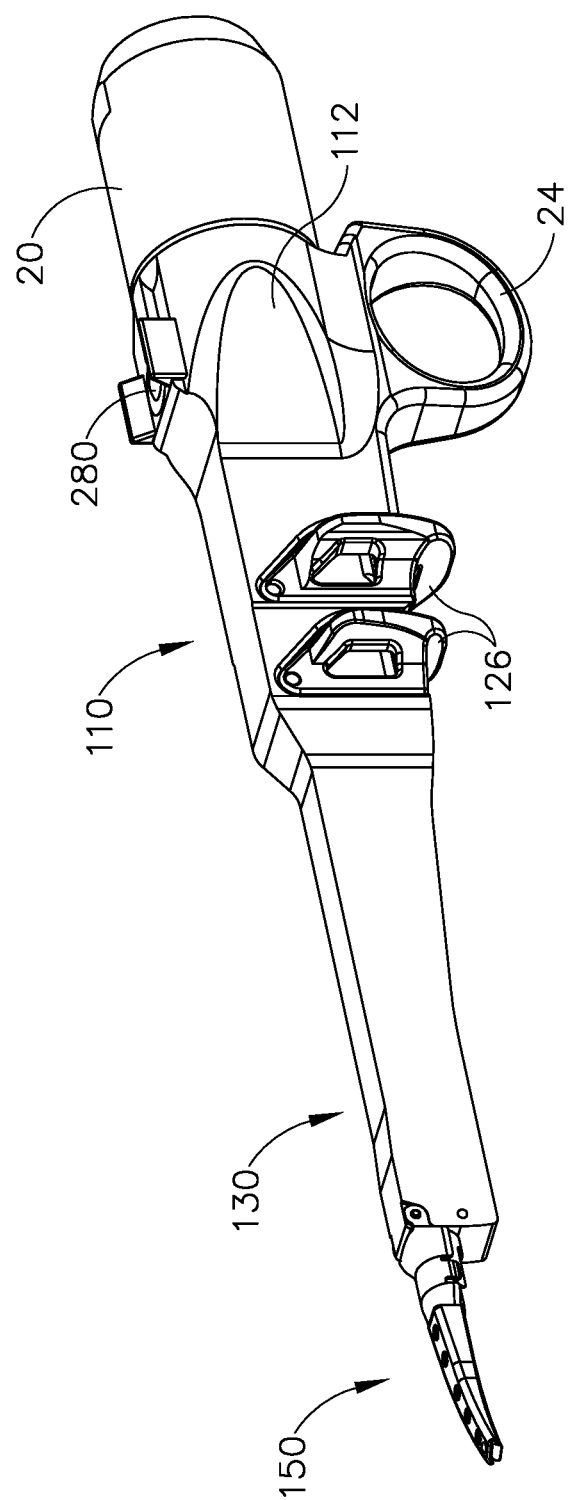
FIG. 4 depicts a perspective view of a handle assembly of the instrument of FIG. 1A.

FIG. 4 shows proximal casing (20), handle assembly (110), shaft assembly (130), and blade assembly (150) with clamp arm assembly (200) detached. As described above, it may be beneficial to have a clamp arm assembly (200) that may selectively detach from the rest of instrument (100) so that certain aspects of instrument (100) may be reusable while other features of instrument (100) are disposed of. In such case, the reusable aspects of instrument (100) will have to be cleaned and sterilized. Providing easy access to areas of instrument (100) that need to be cleaned and sterilized may ensure a thorough cleaning for the next surgical procedure.

Figure 5:
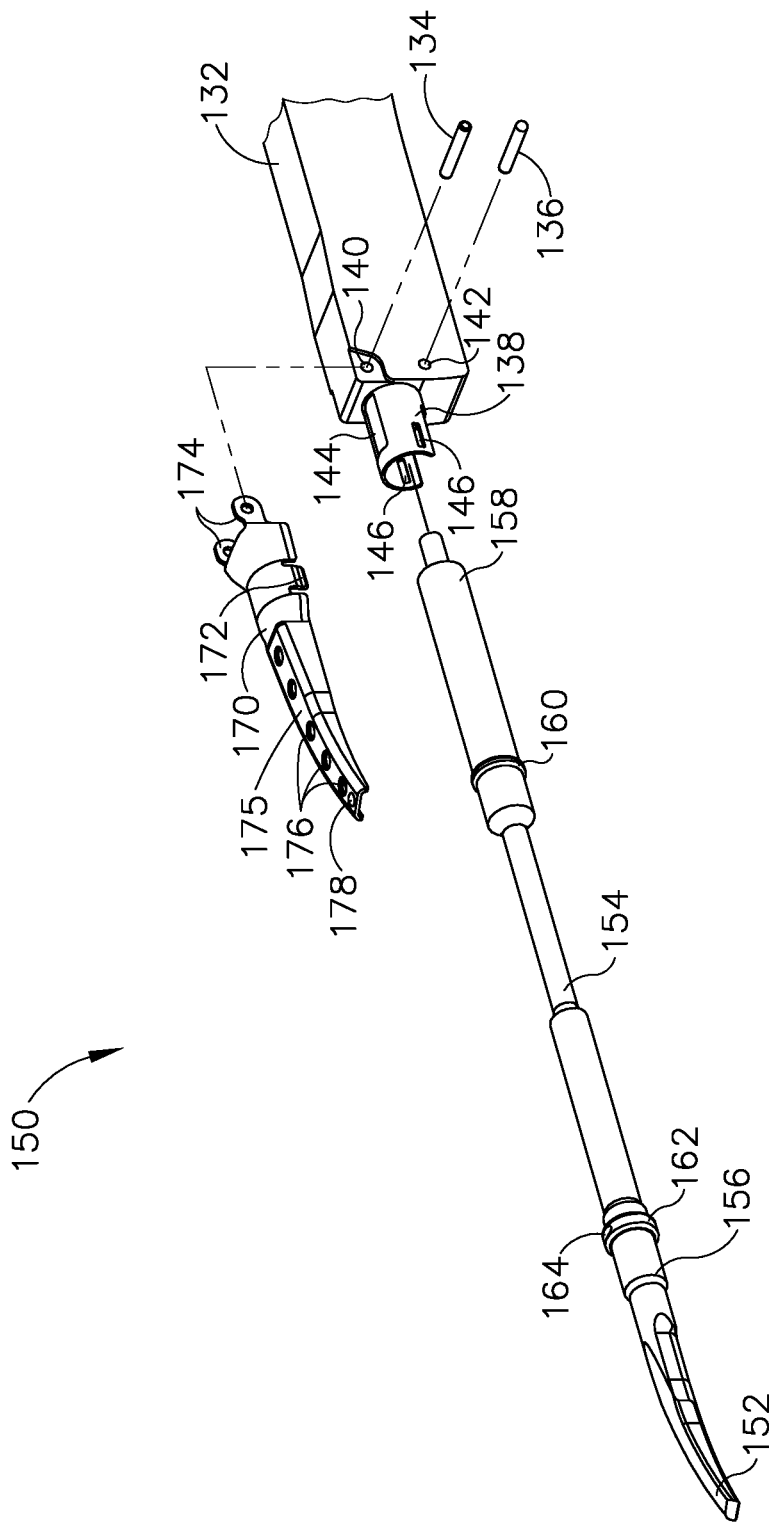
FIG. 5 depicts an exploded view showing a waveguide and heat shield separated from the distal end of the handle assembly of FIG. 4.

FIG. 5 shows a more detailed view of blade assembly (150). Blade assembly (150) includes ultrasonic blade (152), acoustic waveguide (154), and heat shield (170). As will be described in greater detail below, heat shield (170) is capable of pivoting from an unlocked position to a locked position. As also shown in FIG. 5, a tube (138) projects distally from the distal end of outer sheath (132).

Ultrasonic blade (152) is unitarily connected to acoustic waveguide (154). Acoustic waveguide (154) includes a proximal end (158), a distal end (156), a proximal seal (160), and a distal seal (162). As described above, acoustic waveguide (154) communicates ultrasonic vibrations from transducer assembly (30) to ultrasonic blade (152). Acoustic waveguide (154) is housed within shaft assembly (130), more specifically within tube (138) of shaft assembly (130). Proximal seal (160) and distal seal (162) are each located at a respective position along the length of waveguide (154) corresponding to a respective node associated with resonant ultrasonic vibrations communicated through waveguide (154).

Proximal seal (160) and distal seal (162) are sized to abut against the interior of tube (138). Because proximal seal (160) and distal seal (162) are positioned along the length of waveguide (154) corresponding to nodes associated with resonant ultrasonic vibrations, contact between tube (138) and seals (160, 162) may not affect ultrasonic vibrations communication through waveguide (154). Interaction between distal seal (162) and tube (138) may prevent fluids from traveling proximally within tube (138) in relation to distal seal (162).

Figure 6:
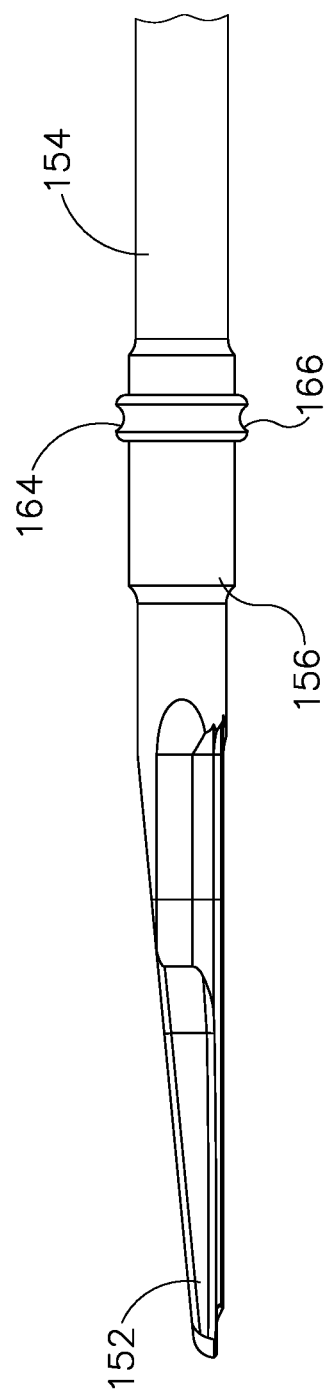
FIG. 6 depicts a side elevational view of an ultrasonic blade of the instrument of FIG. 1A.

As shown in FIG. 6, distal seal (162) includes an upper locking feature (164) and a lower locking feature (166), which are sized to receive locator pins (134, 136). In some versions, locking features (164, 166) are both defined by a single annular recess that extends about the circumferential perimeter of distal seal (162). In some other versions, locking features (164, 166) are formed as discrete scallops or recesses in distal seal (162). As can be seen in FIG. 5, outer sheath (132) includes upper and lower pin holes (140, 142) that are also sized to receive locator pins (134, 136).

Distal seal (162) is located along waveguide (154) such that upper and lower locking features (164, 166) longitudinally align with upper and lower pin holes (140, 142) respectively, when waveguide (154) is fully seated in handle assembly (110). Additionally, as shown in FIG. 7, tube (138) includes slots (148) that are located within outer sheath (132). Slots (148) are positioned to align with upper and lower pin holes (140, 142) of outer sheath (132). Slots (148) are also sized and located along the length of tube (130) in order to receive locator pins (134, 136). Therefore, when acoustic waveguide (154) is housed within tube (138) and fully seated in handle assembly (110), locator pins (134, 136) may be inserted into upper and lower pin holes (140, 142), thereby entering slots (148) of tube (138) and making contact with upper locating feature (164) and lower locating feature (166), respectively. Contact between upper locating feature (164) and locator pin (134), as well as contact between lower locating feature (166) and locator pin (136) impart a frictional braking force on acoustic waveguide (154). This frictional braking force simultaneously prevents acoustic waveguide (154) from rotating about its own longitudinal axis and sliding longitudinally relative to outer sheath (132). Thus, interaction between locator pins (134, 136) and locating features (164, 166) may help acoustic waveguide (154) remain fixed relative to outer sheath (132). Locating features (164, 166) and locator pins (134, 136) may also help reduce tolerance stack between ultrasonic blade (152) and clamp arm assembly (200) due to the location of locating features (164, 166) being positioned close to the distal tip of ultrasonic blade (152).

FIGS. 5 and 8A-9 show heat shield (170) of the present example. As described above, heat shield (170) is capable of pivoting between an unlocked position (FIG. 8A) and a locked position (FIG. 8B). Heat shield (170) includes a pair of spring locks (172), a pair of coupling holes (174), an elongate body (175) that is sized to cover a portion of ultrasonic blade (152), a plurality of apertures (176) located along elongate body (175), and a distal bumper (178). Heat shield (170) may be metal sampled. Head shield (170) may also be coated with a non-stick, non-conductive coating, such as silicone, polytetrafluoroethylene (PTFE), and/or any other suitable material as will be apparent to those of ordinary skill in the art in view of the teachings herein. Because blade assembly (150) may be used multiple times, heat shield (170) may be durable in order to survive multiple uses, handling, and cleaning. By way of example only, heat shield (170) may be constructed in accordance with at least some of the teachings of U.S. Pub. No. 2015/0148833, entitled "Shielding Features for Ultrasonic Blade of a Surgical Instrument," published May 28, 2015, issued as U.S. Pat. No. 9,993,260 on Jun. 12, 2018, the disclosure of which is incorporated by reference herein.

Coupling holes (174) are spaced to align on the outside of upper pin hole (140). Coupling holes (174) are also sized to receive locator pin (134). When coupling holes (174) are aligned with pin hole (140), locator pin (134) may travel through coupling holes (174) and upper pin hole (140), thereby rotatably coupling heat shield (170) to outer sheath (132). Therefore, when assembled, heat shield (170) may rotate about the axis defined by locator pin (134), as shown in the series depicted in FIGS. 8A-8B.

Figure 8A:
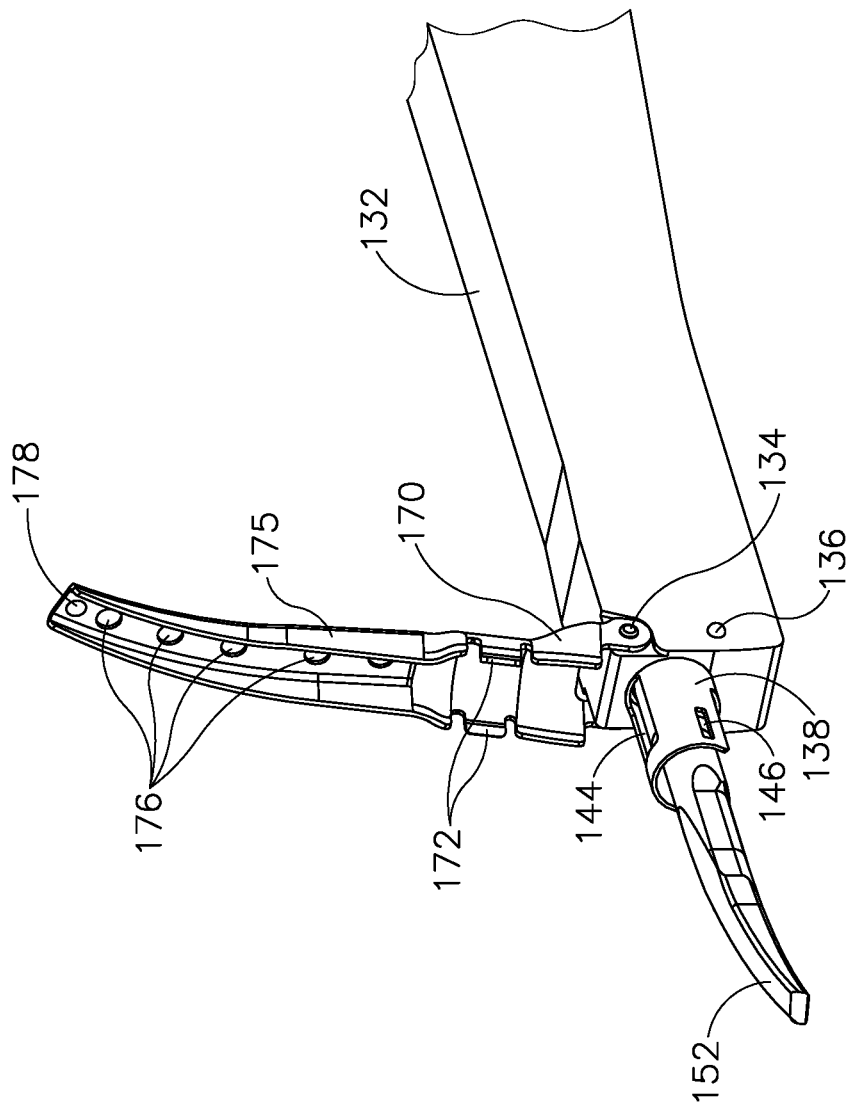
FIG. 8A depicts a perspective view of the ultrasonic blade of FIG. 6 and the heat shield of FIG. 5, with the heat shield pivoted to an upward position.

When heat shield (170) is in an unlocked position, as shown in FIG. 8A, elongate body (175) may be substantially perpendicular with the longitudinal axis defined by outer sheath (132). While heat shield (170) is in the unlocked position, access is provided for cleaning portions of ultrasonic blade (152) and waveguide (154) that would otherwise be covered by heat shield (170). Additionally, tube (138) also defines an access hole (144) to provide further access to cleaning waveguide (154). When heat shield (170) is in a locked position as shown in FIG. 8B, heat shield (170) may prevent ultrasonic blade (152) from inadvertently touching non targeted tissue. Apertures (176) may allow for undesired fluid and tissue to escape the confines of heat shield (170) and ultrasonic blade (152), as to not disturb the vibration of activated ultrasonic blade (152).

As noted above, heat shield (170) includes a pair of spring locks (172). Spring locks (172) are sized to engage tube (138) when heat shield (170) pivots toward the locked position as shown in FIG. 8B. Spring locks (174) are resilient, and capable of flexing to conform to the profile of tube (138) while heat shield (170) pivots toward ultrasonic blade (152). Spring locks (172) are also dimensioned to enter locking slots (146) while heat shield (170) is in the locked position. In other words, the resilient nature of spring locks (172) allows spring locks (172) to return to their natural position once they no longer engage the profile of tube (138) by entering locking slots (146). Once spring locks (172) enter their natural position by engaging locking slots (146) of tube (138), engagement between spring locks (172) and the edges of tube (138) defining locking slots (146) maintains the rotational position of heat shield (170) relative to tube (138). Therefore, heat shield (170) may be substantially fixed relative to the rest of blade assembly (150) when heat shield (170) is in a locked position. Due to the resilient nature of spring locks (172), an operator may rotate heat shield (170) away from ultrasonic blade (152) with enough force to deflect spring locks (172) out of locking slots (146), thereby decoupling spring locks (172) from tube (138). Spring locks (172) will flex outwardly to conform to the profile of tube (138) until heat shield (170) is further pivoted to a fully unlocked position.

Figure 9:
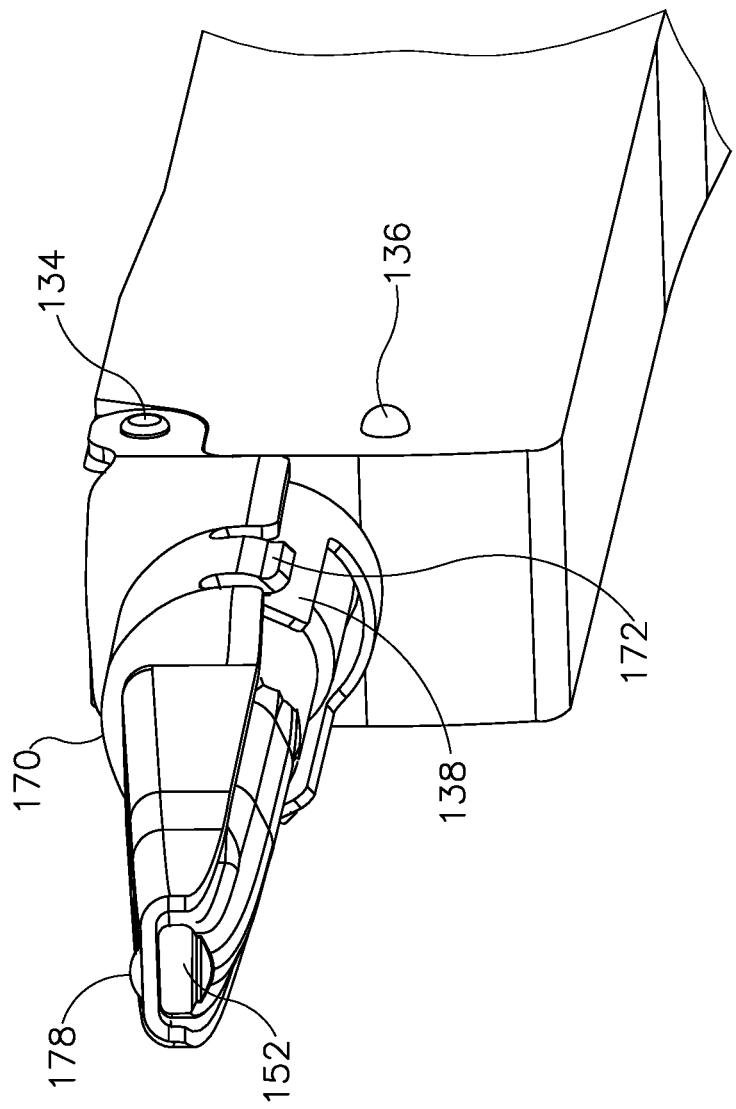
FIG. 9 depicts another perspective view of the ultrasonic blade of FIG. 6 and the heat shield of FIG. 5, with the heat shield in the downward position.

As best seen in FIG. 9, heat shield (170) also includes distal bumper (178). In the present example, distal bumper (178) is formed of an electrically insulative material. By way of example only, distal bumper (178) may comprise polytetrafluoroethylene (PTFE) and/or any other suitable material(s) as will be apparent to those of ordinary skill in the art in view of the teachings herein. Distal bumper (178) may be pressed into place on the distal end of heat shield (170) or attached to the distal end of heat shield (170) using any other suitable features or techniques.

When ultrasonic blade (152) is in use, ultrasonic blade (152) may deflect laterally away from the longitudinal axis in response to forces provided by contact with tissue. Such deflection may urge blade (152) into contact with heat shield (170). If heat shield (170) is made of a metallic substance and instrument (100) is configured to provide RF energy to a surgical location, as described below, a short in the circuit providing RF energy to the surgical location may occur. Distal bumper (178) may thus provide a safe contact surface for ultrasonic blade (152) to contact such that if blade (152) does deflect against the metallic material in heat shield (170) and instead just contacts distal bumper (178), a short circuit of delivered RF energy may be prevented.

C. Exemplary Clamp Arm Assembly

Figure 10:
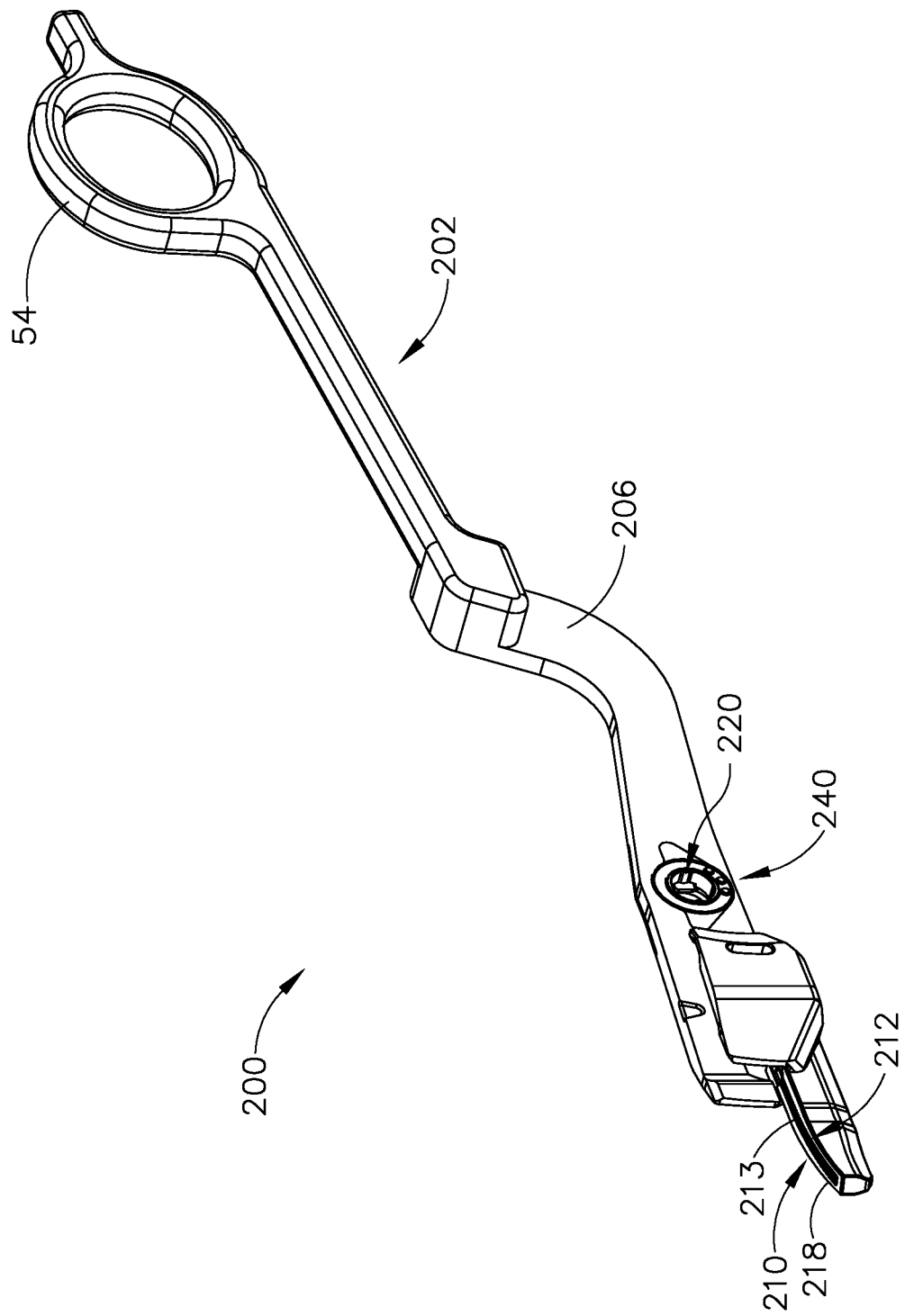
FIG. 10 depicts a perspective view of a clamp arm of the instrument of FIG. 1A.
Figure 11:
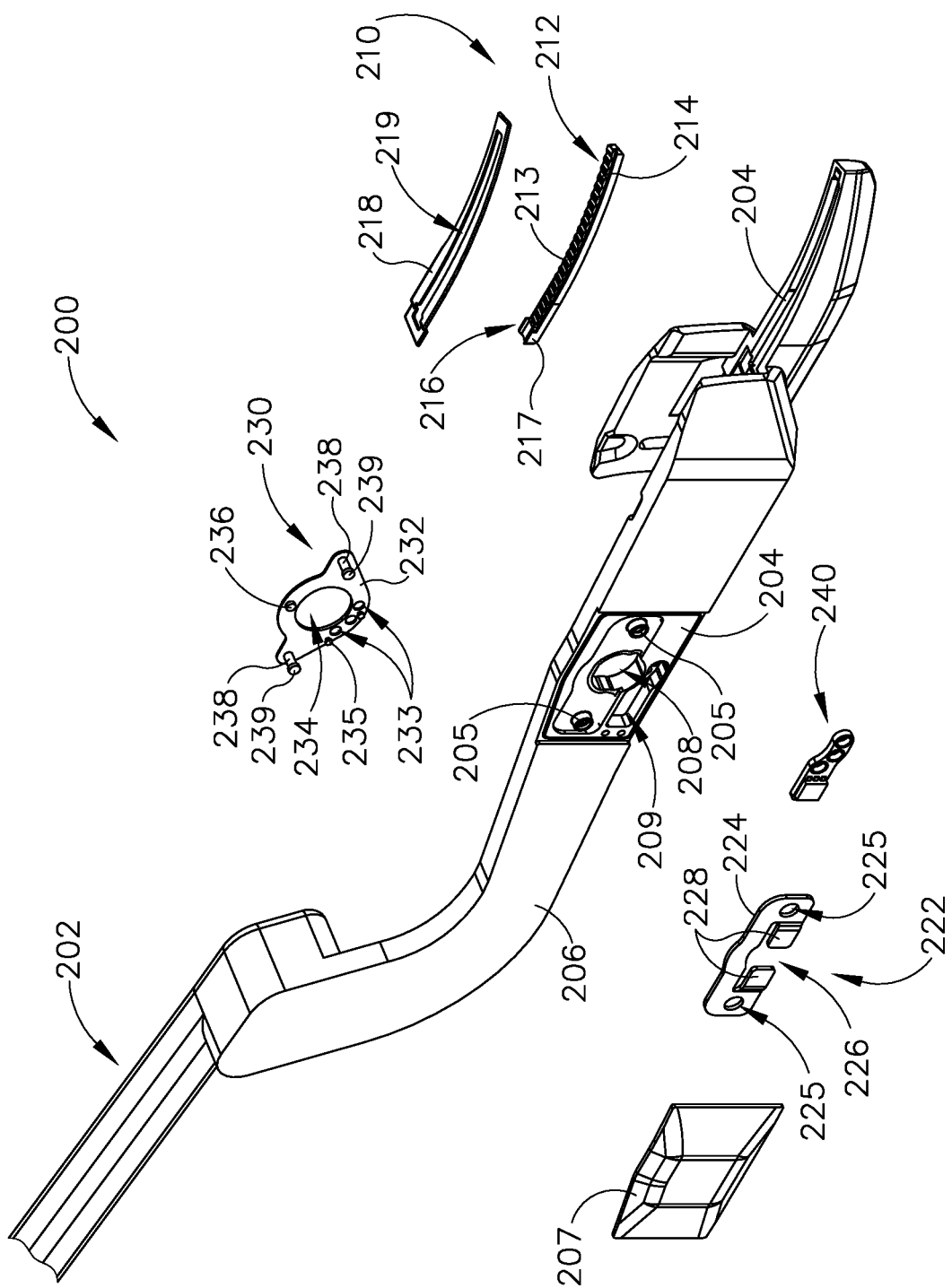
FIG. 11 depicts an exploded view of coupling components of the clamp arm of FIG. 10.

FIGS. 10 and 11 show clamp arm assembly (200) in greater detail. As can be seen, clamp arm assembly (200)

comprises a body (202), a clamp pad assembly (210), a coupling assembly (220), and a data communication assembly (240). Body (202) generally extends from grip (54) to provide a lever that is attachable to handle assembly (110) to support actuate end effector (102). Body (202) generally comprises a structural core (204) with a plastic or rubber overmolded exterior portion (206). As will be described in greater detail below, structural core (204) comprises a generally electrically conducting material that is suitable to transfer RF energy through structural core (204). Core (204) thus provides a path for electrical continuity in addition to providing structural support. As will also be described in greater detail below, the material of structural core (204) is configured to provide structural rigidity to clamp arm assembly (200), while exhibiting at least some elastic properties. In contrast, exterior portion (206) electrically insulates structural core (204), thereby confining RF electrical energy within certain predetermined energy paths.

As can best be seen in FIG. 11, structural core (204) includes two bracket openings (205), a single coupling opening (208), and a single data communication channel (209). As will be described in greater detail below, bracket openings (205) permit at least a portion of coupling assembly (220) to pass through structural core (204) such that coupling assembly (220) is securable to structural core (204). Similarly, coupling opening (208) is configured to permit at least a portion of handle assembly (110) to extend through structural core (204) to engage at least a portion of coupling assembly (220). As will also be described in greater detail below, data communication channel (209) permits at least a portion of data communication assembly (240) to pass through structural core (204) to be in communication with at least a portion of handle assembly (110).

As best seen in FIG. 11, exterior portion (206) includes a removable cover (207) that is selectably detachable from exterior portion (206). Cover (207) is configured to cover and un-cover at least a portion of structural core (204) to provide operator access to coupling assembly (220) and data communication assembly (240). In some examples such access may be desirable for assembly purposes. Cover (207) of the present example is generally securable to exterior portion (206) by a press fit. Although not shown, it should be understood that in some examples cover (207) includes snaps, detents, tabs, and/or other features that may be used to secure cover (207) to exterior portion (206). Of course, any other suitable attachment feature may be used as will be apparent to those of ordinary skill in the art in view of the teachings herein.

1. Exemplary Clamp Pad Assembly

Figure 12:
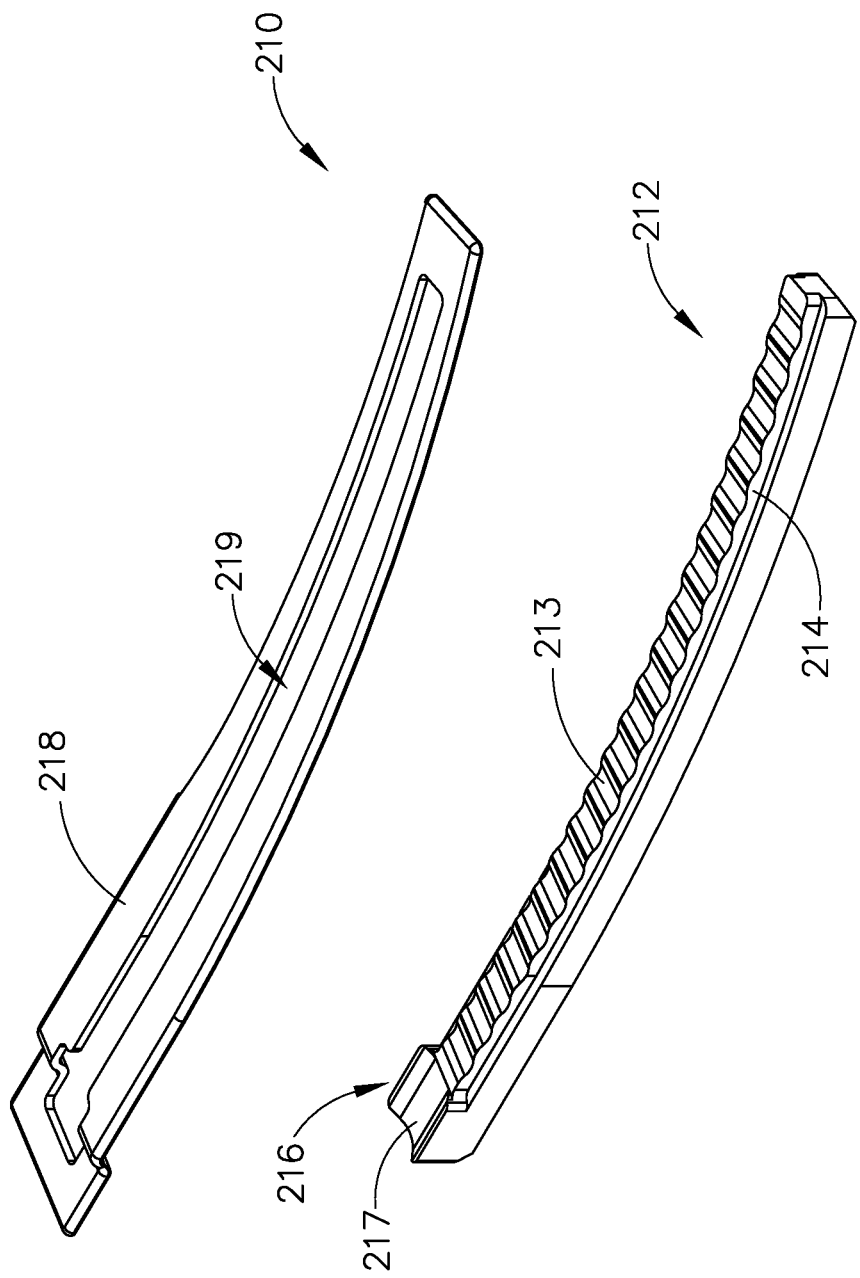
FIG. 12 depicts an exploded view of a clamp pad assembly of the clamp arm of FIG. 10.

FIG. 12 shows clamp pad assembly (210) in greater detail. As can be seen, clamp pad assembly (210) comprises a clamp pad (212) and an electrode (218). Clamp pad (212) comprises a single generally homogenous insulating material such as polytetrafluoroethylene (PTFE), rubber, and/or other similar insulating materials. Clamp pad (212) comprises a gripping portion (213) and a locating portion (216). Gripping portion (213) is configured to grip tissue and hold such tissue in position as the tissue is being clamped between clamp pad assembly (210) and ultrasonic blade (152). In the present example, gripping portion (213) includes a repeating pattern of ribs or teeth to enhance the grippability of gripping portion (213). In other examples, gripping portion (213) is equipped with numerous other features to enhance grippability such as knurling, irregular surface patterns, or any other generally rough surface. In still other examples, gripping portion (213) is equipped with a merely flat surface without any particular feature to enhance grippability.

Gripping portion (213) terminates inwardly of the outer lateral edges of clamp pad (212). This defines a shoulder (214) in clamp pad (212). As will be described in greater detail below, shoulder (214) is generally configured to maintain clamp pad (212) within body (202) via electrode (218).

Locating portion (216) is defined in clamp pad (212) at the proximal end of clamp pad (212). Locating portion (216) extends upwardly above gripping portion (213) with an indented upper surface (217). As will be described in greater detail below, locating portion (216) is generally configured to maintain relative positioning between clamp pad (212) and blade (152) during clamping, by receiving blade (152) within upper surface (217). Accordingly, it should be understood that upper surface (217) generally corresponds to the curvature of blade (152) such that upper surface is configured to receive blade (152).

Electrode (218) comprises a single relatively thin strip of relatively rigid electrically conducting material. In some examples electrode (218) comprises an electrically conductive metal such as copper, gold, steel, aluminum, silver, etc. In still other examples, electrode (218) comprises an electrically conductive non-metallic material such as conducting polymers, silicides, graphite, etc. The thickness of electrode (218) is generally thinner than gripping portion (213) of clamp pad (212), such that gripping portion (213) protrudes above the upper surface of electrode (218). However, electrode (218) is still generally thick enough to maintain a suitable amount of structural rigidity, as will be described in greater detail below.

The particular shape of electrode (218) generally corresponds to the shape of clamp pad (212). In particular, electrode (218) generally defines a shape similar to an outline of clamp pad (212). Electrode (218) further defines an opening (219) therein. Opening (219) is configured to receive gripping portion (213) of clamp pad (212) therethrough such that electrode (218) is configured to engage with shoulder (214) of clamp pad (212).

When clamp pad assembly (210) is assembled, clamp pad (212) is first inserted into a clamp pad receiving channel (208) defined in the distal end of body (202). Electrode (218) is then inserted over clamp pad (212), with electrode (218) seating on shoulder (214) of clamp pad (212), and with gripping portion (213) of clamp pad (212) protruding through opening (219). Electrode (218) is then resistance welded or otherwise secured to body (202). In the present example, electrode (218) is resistance welded in place to structural core (204) of body (202) at the proximal and distal ends of electrode (218). In other examples, electrode (218) is resistance welded at any other suitable location in addition to, or in lieu of, welding at the distal and proximal ends of electrode (218). In still other examples, resistance welds are omitted entirely and electrode (218) is secured to body (202) by any other suitable means such as other welding processes and/or adhesive bonding, etc. It should be understood that once electrode (218) is secured to body (202), electrode (218) also couples clamp pad (212) to body (202) by engagement between electrode (218) and shoulder (214) of clamp pad (212). Accordingly, the thickness of electrode (218) is generally thick enough to provide enough rigidity to couple clamp pad (212) to body (202).

Electrode (218) is configured to cooperate with blade (152) to provide bipolar RF electrosurgical energy to tissue that is captured between clamp pad assembly (210) and blade (152). In particular, electrode (218) is activated with RF energy and blade (152) provides a return path for the RF energy. It should therefore be understood that blade (152) is capable of serving two distinct roles in the present example—one role of applying ultrasonic energy to tissue that is in contact with blade (152) and another role of cooperating with electrode (218) to provide bipolar RF energy to tissue that is captured between clamp pad assembly (210) and blade (152). In some versions, the ultrasonic energy and RF energy are applied simultaneously. In some other versions, the ultrasonic energy and RF energy are applied in an automatically alternating fashion. In some other versions, the ultrasonic energy and RF energy are applied in a simple series (e.g., ultrasonic energy first, followed by RF energy). In some other versions, the ultrasonic energy and RF energy are selectively applied independently (e.g., with one button (126) activating ultrasonic energy and the other button activating RF energy). Various suitable features that may be used to provide communication of RF energy through electrode (218) and blade (152) will be described in greater detail below. Other suitable features that may be used to provide communication of RF energy through electrode (218) and blade (152) will be apparent to those of ordinary skill in the art in view of the teachings herein.

In the present example, because electrode (218) is generally thinner than gripping portion (213) of clamp pad (212), gripping portion (213) generally protrudes upwardly from electrode (218) to prevent blade (152) from directly contacting electrode (218) when end effector (102) is in a closed configuration. Thus, it should be understood that electrode (218) is generally not configured to physically contact blade (152). However, as will be described in greater detail below, electrical continuity for RF energy is generally achieved by passing electrical current through a patient's tissue as it is cut and/or sealed using instrument (100), and in some versions this electrical current flows between electrode (218) and blade (152).

2. Exemplary Coupling Assembly

Figure 13:
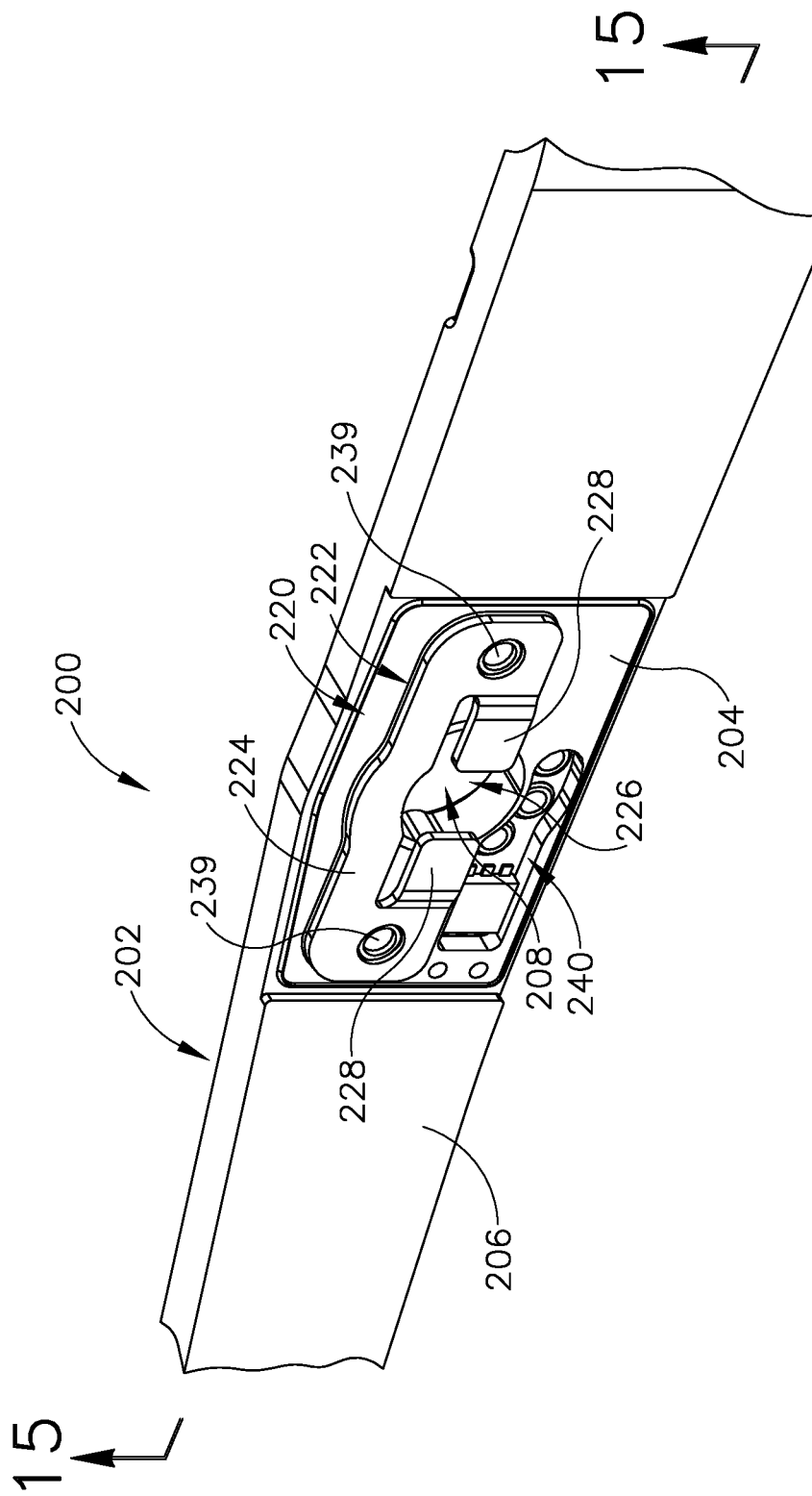
FIG. 13 depicts a perspective view of the coupling components of FIG. 11.
Figure 14:
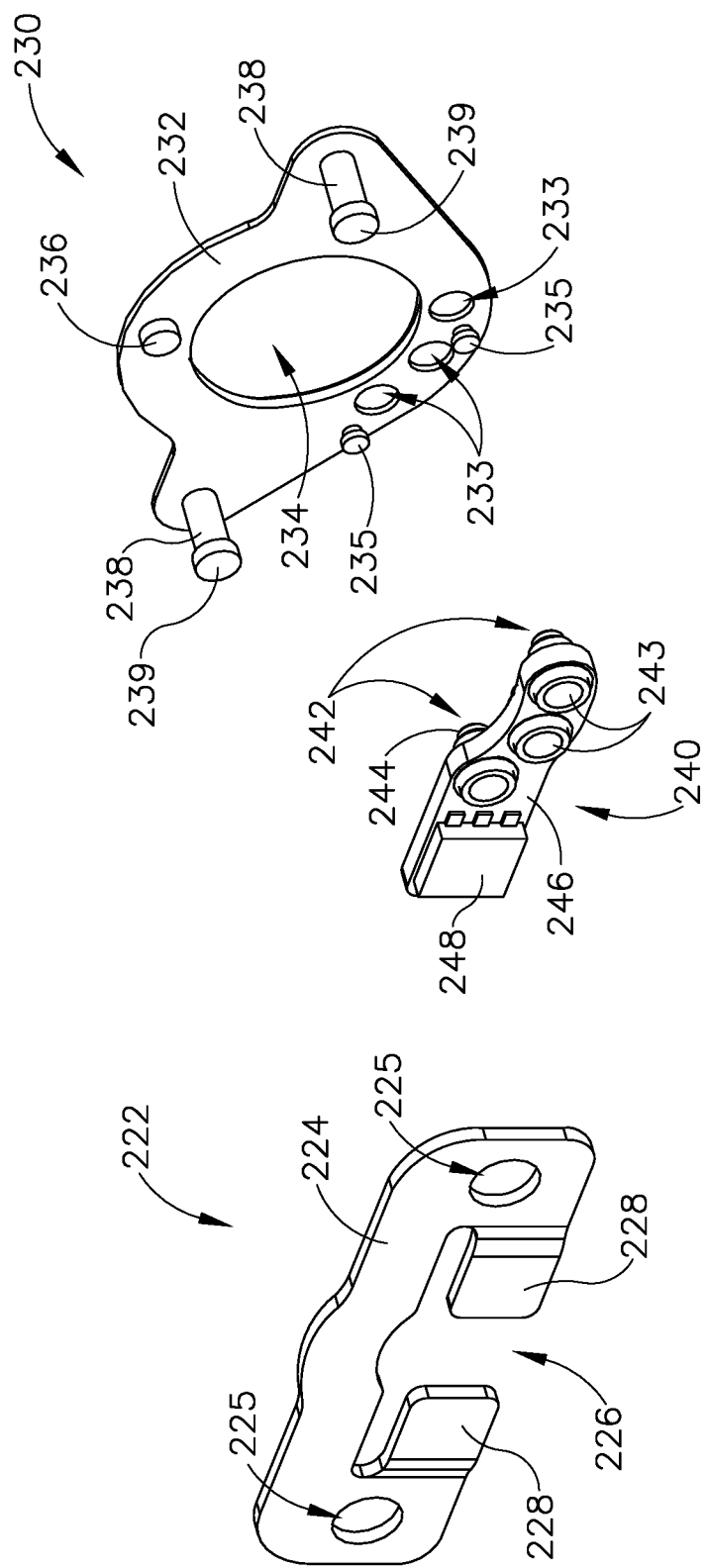
FIG. 14 depicts an enlarged exploded view of some of the coupling components of FIG. 11.

FIGS. 13-16 show coupling assembly (220) in greater detail. As is best seen in FIG. 14, coupling assembly (220) comprises a coupling plate (222) and a retaining bracket (230). Coupling plate (222) is generally configured to receive at least a portion of handle assembly (110) to selectively couple clamp arm assembly (200) to handle assembly (110). It should be understood that the term "couple" referred to herein encompasses fixedly securing clamp arm assembly (200) to handle assembly (110) relative to at least one axis. For instance, as will be described in greater detail below, in the present example clamp arm assembly (200) is couplable to handle assembly (110) such that lateral movement of clamp arm assembly (200) is restricted relative to handle assembly (110). However, as will also be described in greater detail below, coupling assembly (220) is configured to permit at least some longitudinal movement and rotational movement of clamp arm assembly (200) relative to handle assembly (110).

Coupling plate (222) of the present example comprises a generally rectangular base (224) with a plurality of inwardly extending coupling arms (228). Although coupling plate (222) is shown as a generally unitary part, it should be understood that in other examples, coupling plate (222) comprises an assembly of a plurality of discrete parts. Regardless of whether coupling plate (222) comprises a single unitary part or a plurality of discrete parts, it should be understood that coupling plate (222) is generally comprised of a conductive metallic or conductive non-metallic material. As will be described in greater detail below, coupling plate (222) is generally configured to transfer electrical RF energy from at least a portion of handle assembly (110) to structural core (204) of body (202).

Base (224) of coupling plate (222) defines a pair of bracket openings (225) and a single arm opening (226). As will be described in greater detail below, bracket openings (225) are generally configured to receive at least a portion of retaining bracket (230) such that retaining bracket (230) and coupling plate (222) are securable to structural core (204) of body (202). As will also be described in greater detail below, arm opening (226) is sized to receive coupling arms (228) such that at least a portion of handle assembly (110) may extend through base (224) to engage coupling arms (228).

Coupling arms (228) of the present example comprises two coupling arms (228), although in other examples any suitable number of coupling arms (228) is used. Each coupling arm (228) extends inwardly into arm opening (226) of base (224) from opposite sites of base (224). However, each arm (228) stops short of extending all the way to the adjacent arm, thereby leaving at least a portion of arm opening (226) open. As will be described in greater detail below, this portion of arm opening (226) is configured to permit at least a portion of handle assembly (110) to extend through base (224) and past arms (228) such that at least a portion of handle assembly (110) engages arms (228).

Each coupling arm (228) is laterally offset from base (224). In the present example this structure is formed by stamping a bend in base (224) and each coupling arm (228) to position each arm (228) laterally away from base (224). As will be described in greater detail below, this feature of arms (228) is configured to suitably align handle assembly (110) when at least a portion of handle assembly (110) engages arms (228). Additionally, each coupling arm (228) of the present example is configured to be resilient. As will also be described in greater detail below, this resilient feature of arms (228) provides spring like characteristics to arms (228) to further promote alignment between handle assembly (110) and clamp arm assembly (200) along a transverse plane.

Retaining bracket (230) comprises a base portion (232) and a pair of retaining studs (238). Base portion (232) comprises a plate having a generally triangular shape, although any other suitable shape may be used in other examples. Base portion (232) further includes a plurality of data communication openings (233), and a single coupling opening (234). Base portion (232) of the present example defines three discrete data communication openings (233), although in other examples any other suitable number of data communication openings (233) may be defined in base portion (232). As will be described in greater detail below, data communication openings (233) are configured to permit at least a portion of data communication assembly (240) to extend through retaining bracket (230) to communicate with handle assembly (110).

Coupling opening (234) is centrally disposed within base portion (232). As will be described in greater detail below, coupling opening (234) is sized to permit at least a portion of handle assembly (110) to pass through base portion (232) to engage coupling plate (222). As will also be described in greater detail below, coupling opening (234) is further configured to align with a corresponding opening (208) in structural core (204) of body (202) to further permit at least a portion of handle assembly (110) to pass thorough base portion (232) to engage coupling plate (222).

Base portion (232) further includes a plurality of alignment features (235, 236). Each alignment feature (235, 236) comprises a laterally extending cylindrical protrusion. Alignment features (235, 236) are generally configured to locate base portion (232) relative to clamp arm assembly (200). For instance, alignment features (235, 236) comprise a pair of data communication alignment features (235) that locate data communication assembly (240) relative to base portion (232). Similarly, alignment features (235, 236) further comprise a single base alignment feature (236) that locates base portion (232) relative to structural core (204) of body (202). Although not shown, it should be understood that each alignment feature (235, 236) is configured to engage a corresponding bore or opening (not shown) of data communication assembly (240) and structural core (204), respectively.

Retaining studs (238) comprise a generally cylindrical shape and extend laterally from base portion (232). Each retaining stud (238) comprises a retaining feature (239) disposed on the lateral end of each retaining stud (238). Each retaining feature (239) is formed as a head that is generally cylindrical in shape and includes a diameter that is greater than the diameter of each retaining stud (238). As will be understood, retaining features (239) are generally configured to secure retaining bracket (230) to clamp arm assembly (200) and further secure base portion (232) to clamp arm assembly (200).

Figure 15:
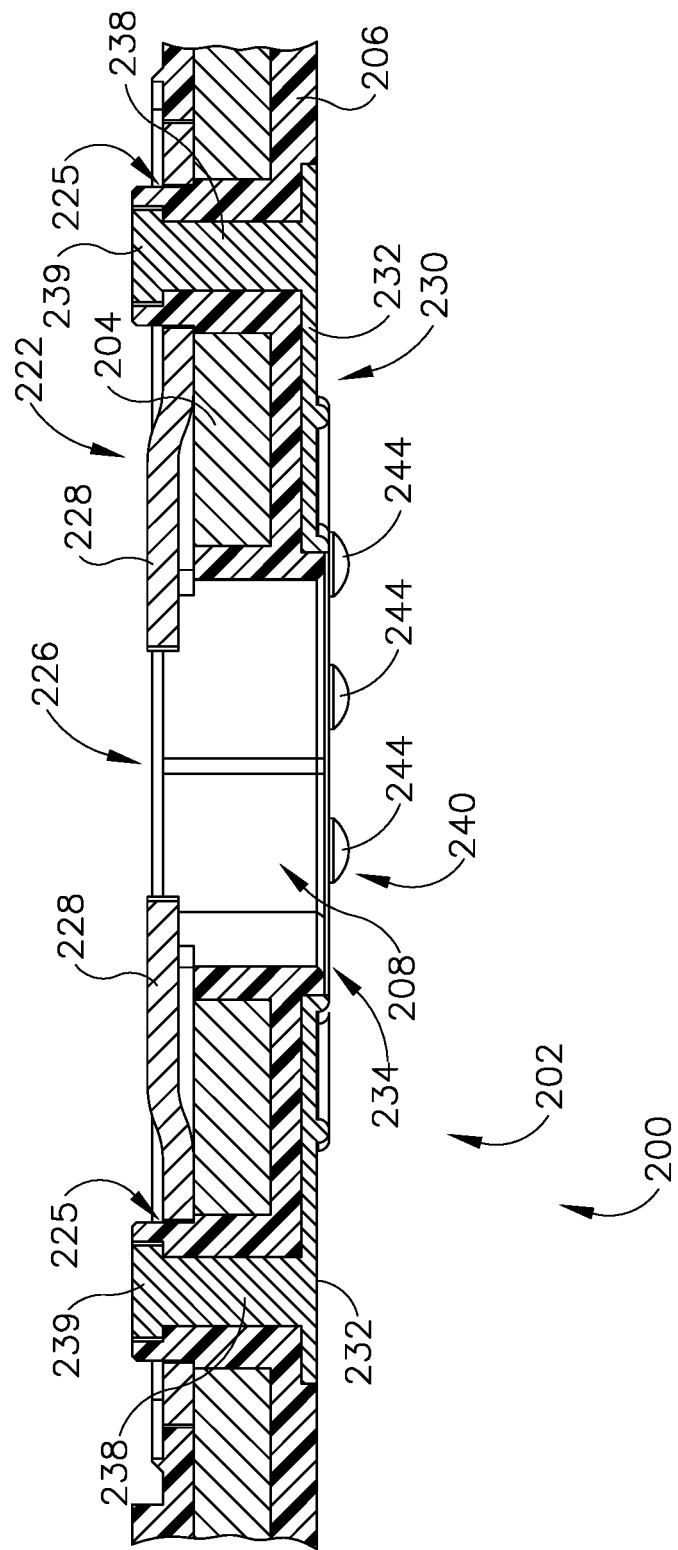
FIG. 15 depicts a cross-sectional view of the coupling components of FIG. 11, taken along line 15-15 of FIG. 13.

As is best seen in FIG. 15, when clamp arm assembly (200) is fully assembled retaining studs (238) extend through bracket openings (205) of structural core (204) and through bracket openings (225) of coupling plate (222). In the present example, exterior portion (206) of body (202) is also overmolded into bracket openings (205) of structural core (204) to surround retaining studs (238), although such a configuration is merely optional.

Coupling plate (222) is fixedly secured to retaining bracket (230) and correspondingly to structural core (204) by retaining studs (238). In particular, retaining studs (238) extend through bracket openings (205) of structural core (204) and through bracket openings (225) of coupling plate (222). To maintain the position of retaining bracket (230), exterior portion (206) of body (202) is overmolded into a shape corresponding to the geometry of retaining studs (238). The positioning of coupling plate (222) is then maintained relative to body (202) and retaining bracket (230) by a compression fit between exterior portion (206) of body (202) and retaining studs (238). While FIG. 15 shows one merely exemplary configuration for securing coupling plate (222) and retaining bracket (230) to structural core (204), it should be understood that in other example numerous alternative configurations are used. For instance, in some examples retaining studs (238) extend through bracket openings (205, 225) without exterior portion (206) and connect directly to coupling plate (222) via screws, washers, bolts and/or other attachment features. Of course other suitable configurations for securing coupling plate (222) and retaining bracket (230) to structural core (204) will be apparent to those of ordinary skill in the art in view of the teachings herein.

In the configuration shown in FIG. 15, coupling plate (222) is in direct physical contact with structural core (204) of body (202). Because both structural core (204) and coupling plate (222) are both electrical conductors, it should be understood that coupling plate (222) is in electrical communication with structural core (204). As will be described in greater detail below, this permits electrical RF energy to be communicated from at least a portion of handle assembly (110) to electrode (218) via coupling plate (222) and structural core (204).

3. Exemplary Data Transfer Assembly

FIGS. 13-14 show data communication assembly (240) in more detail. As is best seen in FIG. 14, data communication assembly (240) comprises a plurality of electrical connectors (242), a printed circuit board (246), and an electrical circuit (248). Data communication assembly (240) of the present example comprises three electrical connectors (242), although in other examples any suitable number may be used. Each electrical connector (242) of the present example is generally configured as a pogo pin-style connector. In particular, each electrical connector (242) comprises a barrel (243) and a ball (244) protruding from each barrel (243). Of course, connectors (242) may take any other suitable form.

Barrel (243) is attached to printed circuit board (246) to provide electrical communication between electrical connector (242) and printed circuit board (246). Although not shown, it should be understood that each barrel (243) also includes one or more resilient features such as a spring located within each barrel (243). Each ball (244) protrudes from each barrel (243) and is held in position by the one or more resilient features. Each ball (244) is configured to act as an electrical contact to communicate electrical current through barrel (243) to printed circuit board (246). Additionally, due to the one or more resilient features of barrel (243), each ball (244) is configured to travel through a predetermined range of motion to permit some movement of ball (244) while still maintaining electrical continuity with a corresponding electrical contact. As will be described in greater detail below, each electrical connector (242) is generally configured to pass through structural core (204) of body (202) to provide data communication between handle assembly (110) and clamp arm assembly (200).

Printed circuit board (246) communicates electrical current from electrical connectors (242) to electrical circuit (248). Thus, electrical circuit (248) is in electrical communication with electrical connectors (242) via printed circuit board (246) to send and/or receive data. In the present example, electrical circuit (248) includes at least a non-volatile memory chip, as well as other operational components such as integrated circuits. As will be described in greater detail below, electrical circuit (248) is generally configured to provide various types of data regarding clamp arm assembly (200) to generator (5) via handle assembly (110).

As is best seen in FIG. 15, when clamp arm assembly (200) is fully assembled, data communication assembly (240) extends through body (202) and protrudes laterally from body (202). In particular, each ball (244) of each electrical connector (242) is resiliently biased to protrude laterally at least partially through body (202) from a side opposite of coupling plate (222). The particular amount of protrusion of balls (244) in the present example is approximately equivalent to the predetermined range of motion of each ball (244), although the amount of protrusion is varied in other examples. As will be described in greater detail below, balls (244) generally protrude from body (202) to provide electrical continuity between data communication assembly (240) and handle assembly (110).

Figure 16:
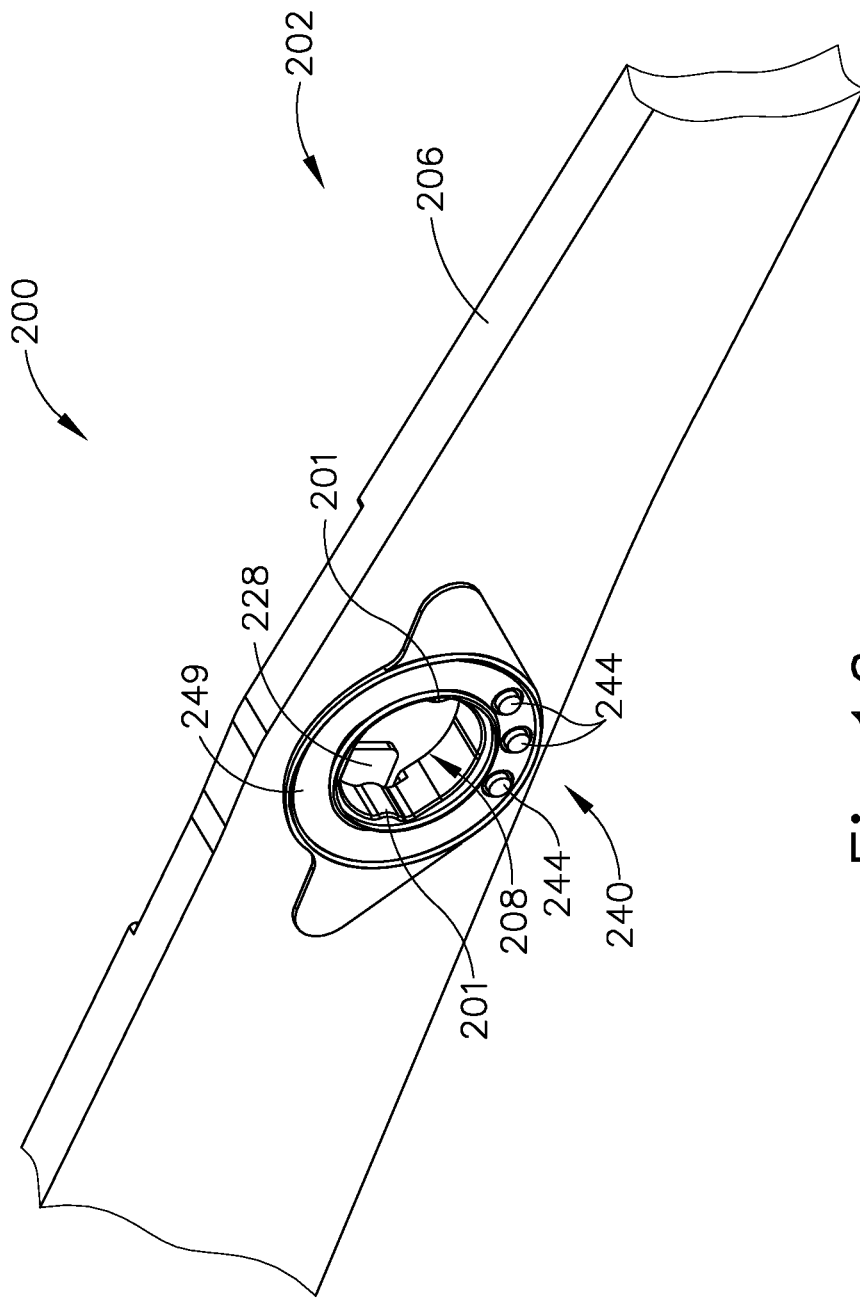
FIG. 16 depicts an enlarged perspective view of some of the coupling components of FIG. 11.

FIG. 16 shows another view of balls (244) protruding through body (202). As can be seen, the exterior of body (202) is equipped with a seal (249) covering retaining bracket (230). Seal (249) of the present example is overmolded onto body (202), although in other examples numerous other means of attachment are used to secure seal (249) to body (202). Seal (249) is configured to provide a fluid seal between the exterior of clamp arm assembly (200) and data communication assembly (240). This prevents various fluids encountered during a surgical procedure that may harm components of data communication assembly (240) (e.g., electrical circuit (248)) from otherwise entering data commutation assembly (240).

D. Exemplary Coupling of Handle Assembly with Clamp Arm Assembly

FIGS. 17-18 show a coupling assembly (250) of handle assembly (110) that is generally configured to selectively couple with clamp arm assembly (200). In particular, coupling assembly (250) includes an attachment member (252) and a plurality of electrical contacts (266). Attachment member (252) comprises a base (253), and an attachment portion (254). Base (253) is generally cylindrical in shape and extends laterally from the interior of handle assembly (110). At the lateral-most end of base (253) the outer diameter of base (253) narrows to define a generally circular channel (256) between base and attachment portion (254).

Attachment portion (254) of the present example is of unitary construction with base (253) such that base (253) and attachment portion (254) are formed of a single component. Of course, in other examples attachment portion (254) is a discrete component that is secured or otherwise fastened to base (253). Attachment portion (254) is disposed laterally of base (253), adjacent to channel (256). Attachment portion (254) is generally disc-shaped with two flat portions (258) on opposing sides of attachment portion (254). As will be described in greater detail below, flat portions (258) are generally configured to selectively engage coupling plate (222) of clamp arm assembly (200).

As best seen in FIG. 18, attachment portion (254) further includes a first translation feature (260) and a second translation feature (262). Translation features (260, 262) extend transversely along the exterior of attachment portion (254). A corresponding first translation feature (261) and second translation feature (263) are similarly associated with base (253) such that base (253) also includes translation features (261, 263) that extend transversely along the exterior of base (253). As will be described in greater detail below, translation features (260, 261, 262, 263) are configured to translate clamp arm assembly (200) relative to handle assembly (110) as clamp arm assembly (200) is pivoted relative to handle assembly (110), through interaction with corresponding protrusions (201) (shown in FIG. 16) in body (206) of clamp arm assembly (200).

FIG. 18 also shows electrical contacts (266). As can be seen, coupling assembly (250) of handle assembly (110) includes three discrete electrical contacts (266). As will be understood, electrical contacts (266) are configured to correspond to electrical connectors (242) of data communication assembly (240) such that electrical current may be communicated between electrical contacts (266) and electrical connectors (242). In the present example, electrical contacts (266) are spaced a predetermined angular distance from each other along an arc. Each electrical contact (266) is generally positioned flush with the exterior of handle assembly (110). Alternatively, in some examples each electrical contact (266) is positioned to be recessed slightly below the outer surface of handle assembly (110). Regardless of the particular positioning of electrical contacts (266), it should be understood that electrical contacts (266) are generally in communication with the interior of handle assembly (110) to communicate electrical signals from clamp arm assembly (200) to generator (5).

1. Exemplary Procedure for Coupling Clamp Arm Assembly with Handle Assembly

Figure 19A:
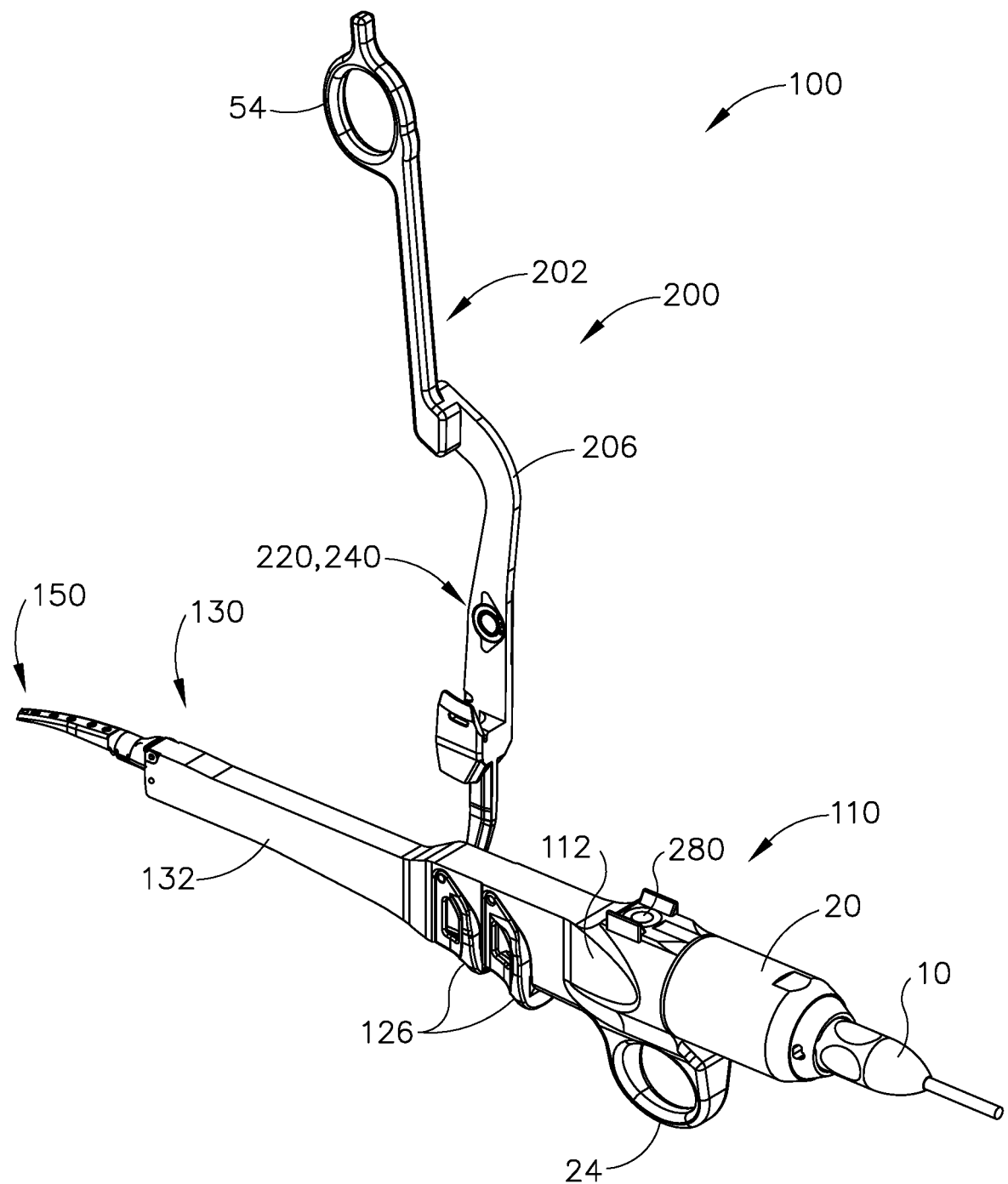
FIG. 19A depicts a perspective view of the instrument of FIG. 1A, with the clamp arm disassembled from the handle assembly.

FIGS. 19A through 21 show an exemplary procedure for coupling clamp arm assembly (200) to handle assembly (110). As is best seen in FIG. 19A, a detached clamp arm assembly (200) is initially positioned relative to handle assembly (110) such that the longitudinal axis of clamp arm assembly (200) is positioned at 90° relative to the longitudinal axis of handle assembly (110). Opening (208) is coaxially aligned with attachment member (252); and clamp arm assembly (200) is spaced laterally from handle assembly (110).

Figure 19B:
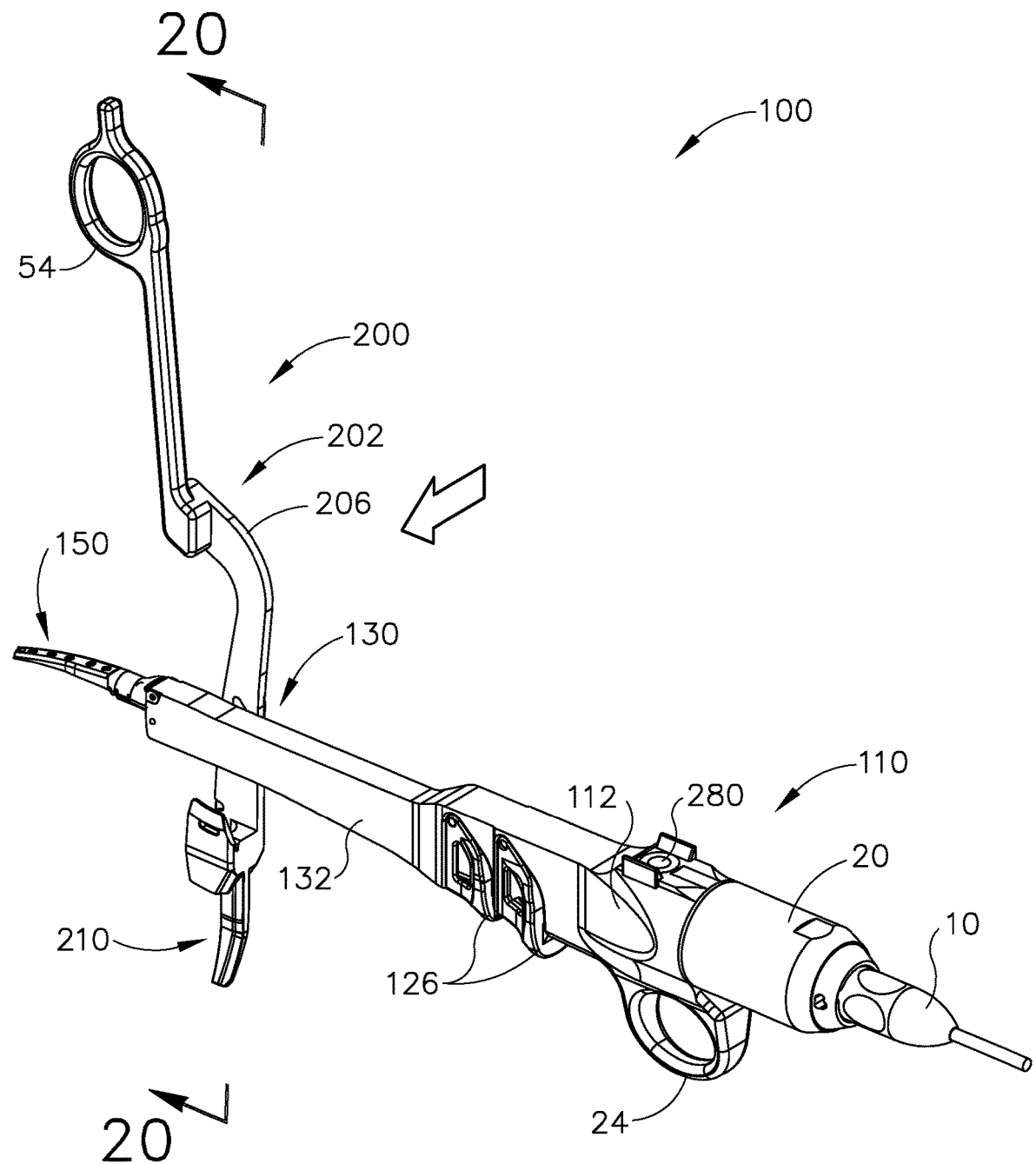
FIG. 19B depicts a perspective view of the instrument of FIG. 1A, with the clamp arm partially assembled with the handle assembly.
Figure 19C:
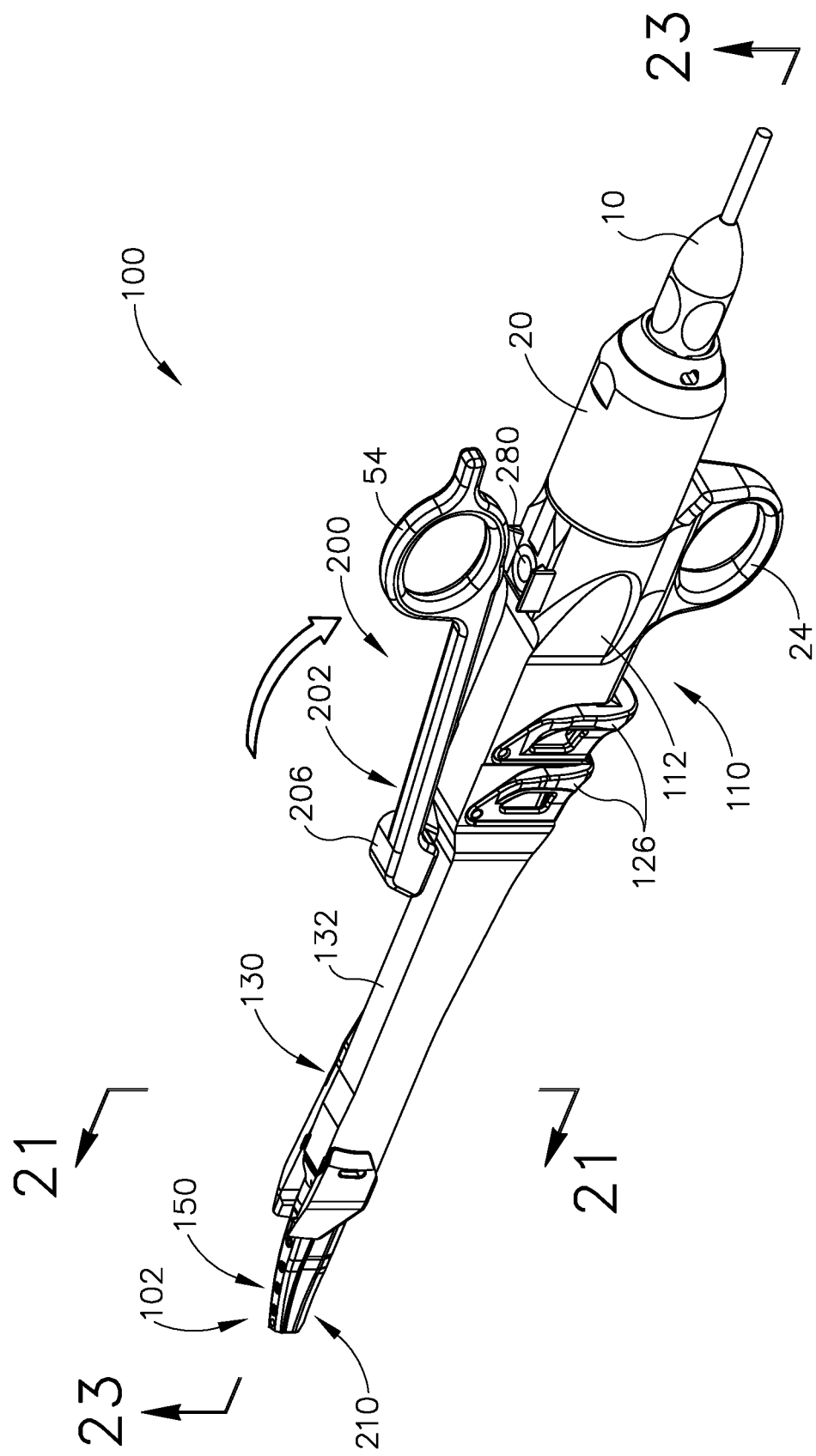
FIG. 19C depicts a perspective view of the instrument of FIG. 1A, with the clamp arm fully assembled with the handle assembly.

Once clamp arm assembly (200) is positioned as shown in FIG. 19A, an operator may begin coupling clamp arm assembly (200) to handle assembly (110). As shown in FIG. 19B, clamp arm assembly (200) is moved laterally by an operator along the axis shared by opening (208) and attachment member (252) to bring clamp arm assembly (200) into contact with handle assembly (110). As clamp arm assembly (200) and handle assembly (110) are brought into contact with each other, attachment member (252) of handle assembly (110) is guided through opening (208) of clamp arm assembly (200) to the position shown in FIG. 20.

Figure 20:
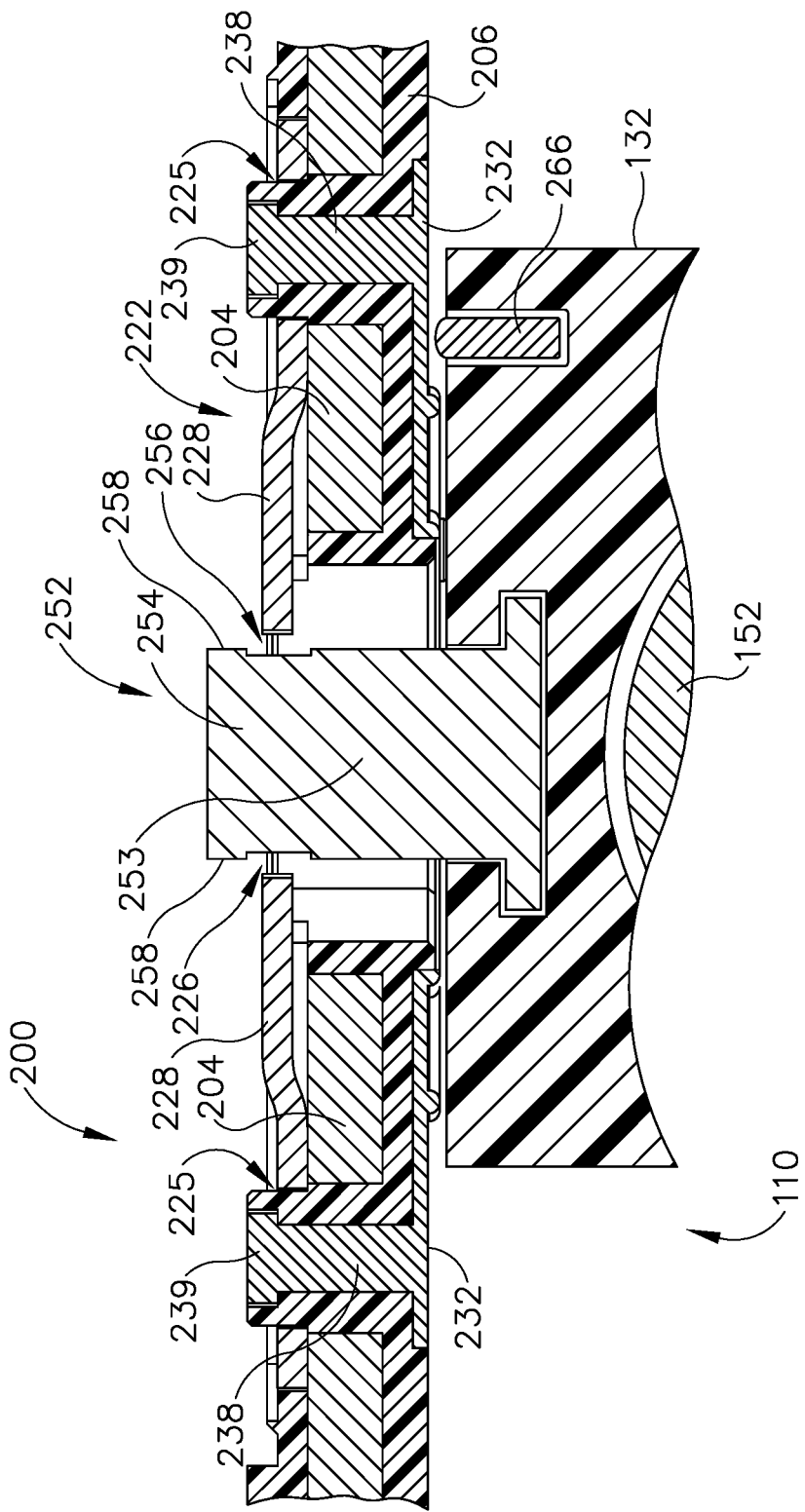
FIG. 20 depicts a partial cross-sectional view of the instrument of FIG. 1A, taken along line 20-20 of FIG. 19B.
Figure 21:
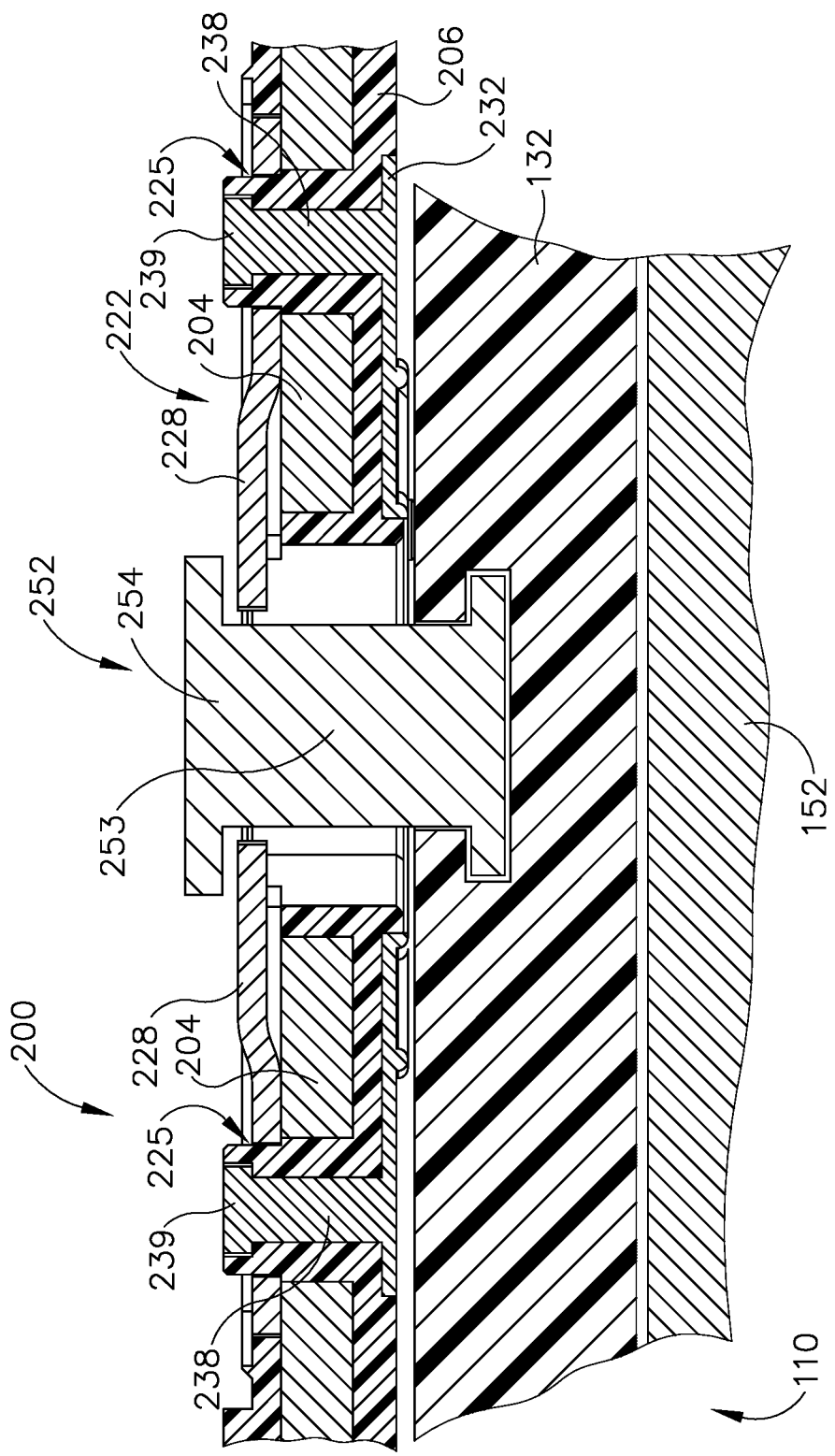
FIG. 21 depicts a partial cross-sectional view of the instrument of FIG. 1A, taken along line 21-21 of FIG. 19C.

As can be seen in FIG. 20, when clamp arm assembly (200) is brought into contact with handle assembly (110) when in the position shown in FIG. 19B, attachment member (252) of handle assembly (110) passes through body (202) of clamp arm assembly (200). As can also be seen in FIG. 20, when clamp arm assembly (200) is in the position shown in FIG. 19B, flat portions (258) of attachment portion (254) are aligned with coupling arms (228) of coupling plate (222) such that attachment portion (254) is aligned to pass through arm opening (226) of coupling plate (222). It should be understood that when attachment member (252) is in the position shown in FIG. 20, attachment portion (254) is correspondingly disposed laterally of coupling arms (228) such that channel (256) of attachment portion (254) is laterally aligned with coupling arms (228).

Once attachment member (252) is suitably positioned relative to clamp arm assembly (200) as shown in FIG. 20, an operator may rotate or pivot clamp arm assembly (200) relative to handle assembly (110), about the axis shared by opening (208) and attachment member (252), to selectively couple clamp arm assembly (200) to handle assembly (110). In particular, as seen in corresponding FIGS. 19C and 21, as clamp arm assembly (200) is rotated, coupling arms (228) correspondingly rotate relative to attachment member (252) such that flat portions (258) of attachment portion (254) move out of alignment with coupling arms (228). With flat portions (258) out of alignment with coupling arms (228), attachment portion (254) engages coupling arms (228) to thereby couple clamp arm assembly (200) to handle assembly (110). The free ends of coupling arms (228) are captured in channel (256) between base (253) and attachment portion (254). Although not shown, it should be understood that in some examples attachment portion (254) includes chamfers, fillets, and/or other features that are configured to promote engagement between attachment portion (254) and coupling arms (228).

Once an operator has successfully coupled clamp arm assembly (200) to handle assembly (110), instrument (100) may be used by an operator to cut and/or seal tissue as described below. It should be understood that at any time during use, an operator may decouple clamp arm assembly (200) from handle assembly (110) by returning clamp arm assembly (200) to the position relative to handle assembly (110) shown in FIG. 19B (e.g., oriented perpendicularly relative to handle assembly (110)). While clamp arm assembly (200) is coupled to handle assembly (110) at angular positions other than that shown in FIGS. 19B and 20, lateral movement of clamp arm assembly (200) relative to handle assembly (110) is generally restrained; while rotational movement and at least some translation is permitted. Although lateral movement of clamp arm assembly (200) is generally restrained, it should be understood that at least some lateral movement may be permitted by the resilient nature of coupling arms (228). Of course, in some examples the particular amount of such movement is varied by providing clamp arms (228) of more or less resiliency. While gross lateral movement of clamp arm assembly (200) is generally undesirable, some minimal amount of lateral movement may be desirable in some examples to account for tolerance variations in instrument.

2. Exemplary Transfer of Data Between Clamp Arm Assembly and Handle Assembly

Figure 22A:
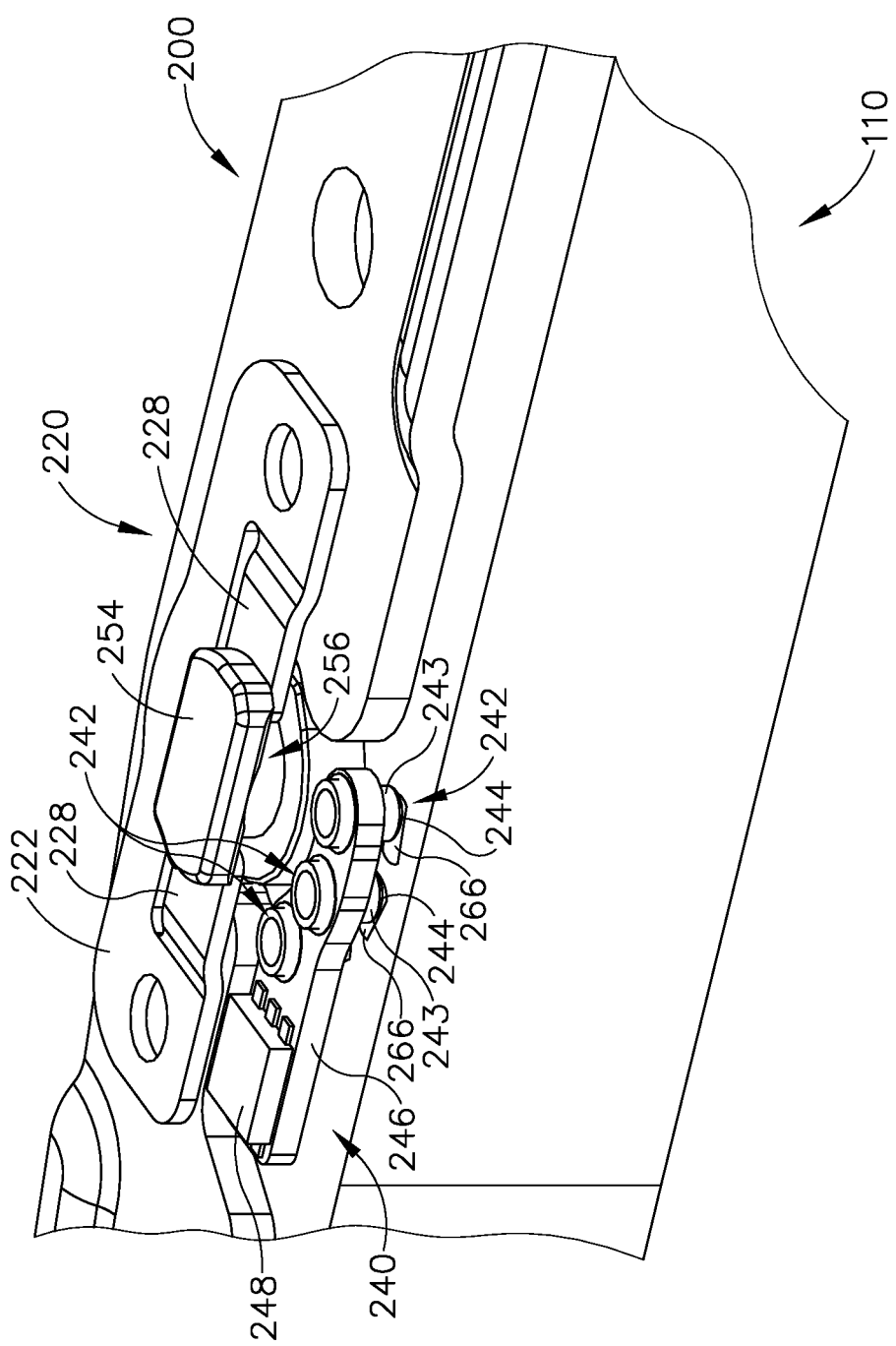
FIG. 22A depicts an enlarged perspective view of some of the coupling components of FIG. 11, with the clamp arm assembly of FIG. 10 at a first pivotal position in relation to the handle assembly of FIG. 4.
Figure 22B:
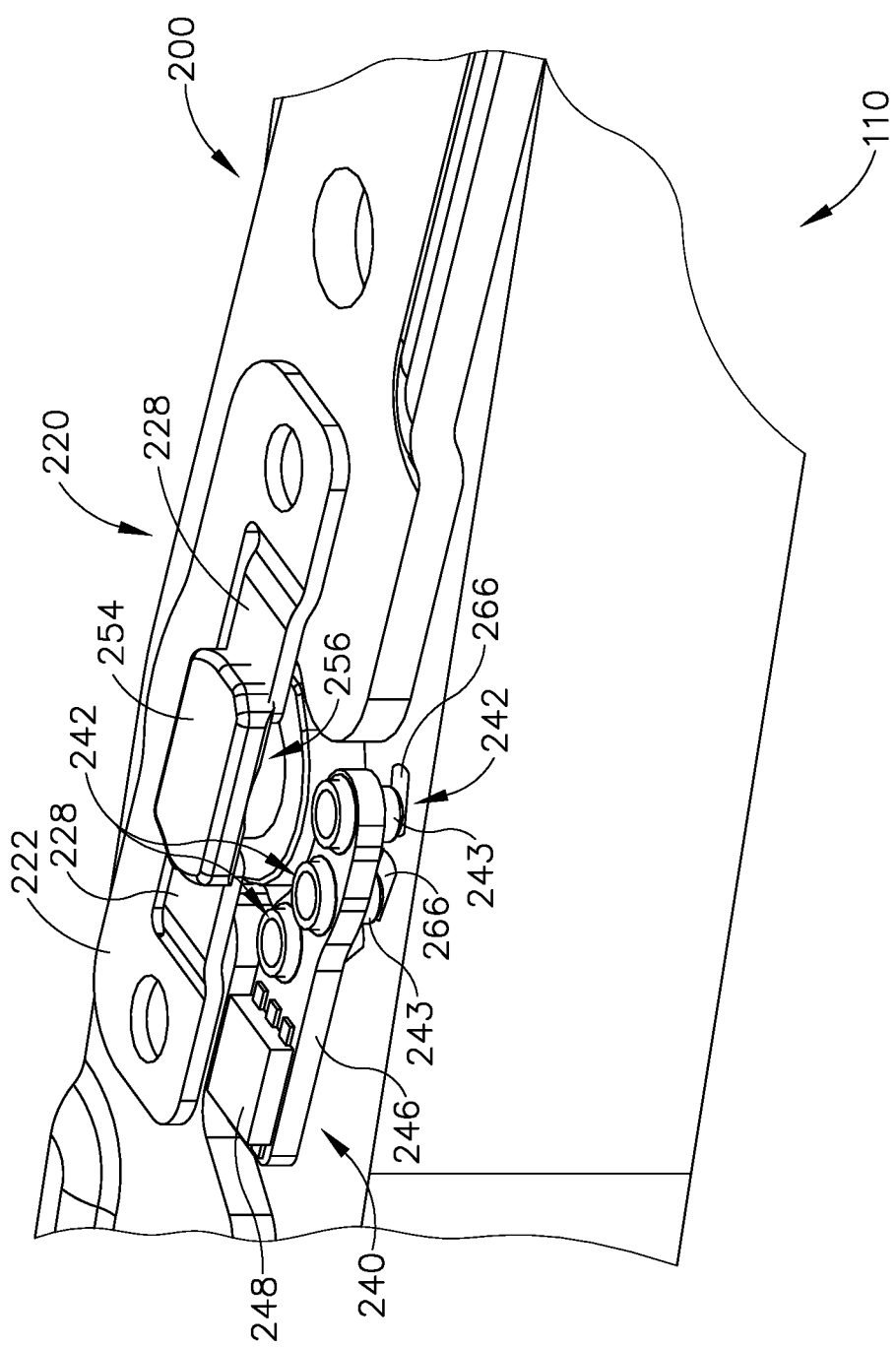
FIG. 22B depicts an enlarged perspective view of some of the coupling components of FIG. 11, with the clamp arm assembly of FIG. 10 at a second pivotal position in relation to the handle assembly of FIG. 4.
Figure 22C:
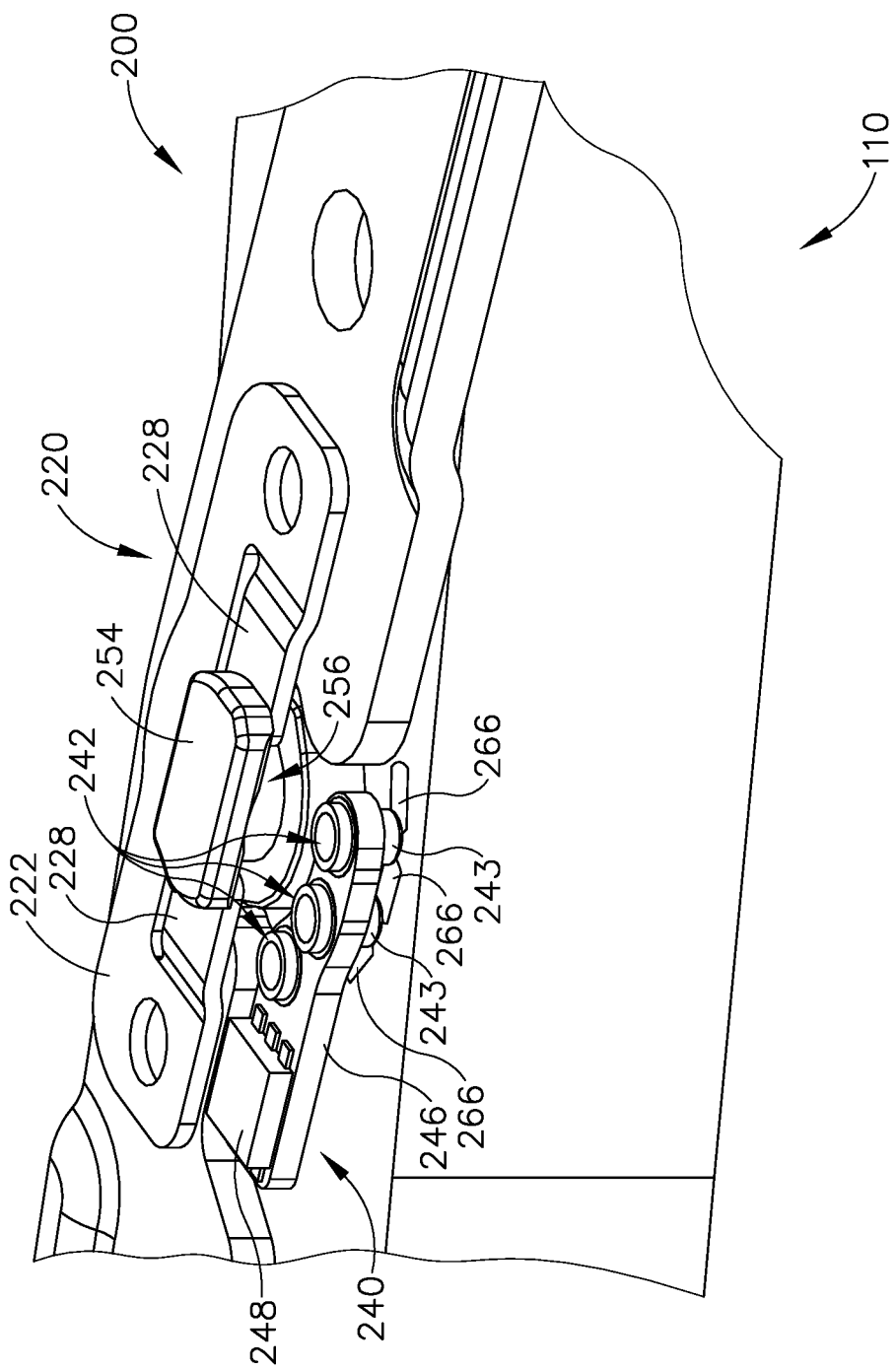
FIG. 22C depicts an enlarged perspective view of some of the coupling components of FIG. 11, with the clamp arm assembly of FIG. 10 at a third pivotal position in relation to the handle assembly of FIG. 4.

FIGS. 22A-C show an exemplary mode of operation between data communication assembly (240) of clamp arm assembly (200) and electrical contacts (266) of handle assembly (110). FIG. 22A corresponds to the position of data communication assembly (240) relative to electrical contacts (266) when end effector (102) is in the closed configuration (e.g., as shown in FIGS. 1A and 2A). As can be seen, when end effector (102) is in the closed configuration, clamp arm assembly (200) is pivoted such that each electrical connector (242) of data communication assembly (240) is in electrical communication with the distal most portion of each corresponding electrical contact (266) of handle assembly (110). Accordingly, when end effector (102) is in the closed configuration, there is electrical continuity between electrical connectors (242) of clamp arm assembly (200) and electrical contacts (266) of handle assembly (110).

Figure 1B:
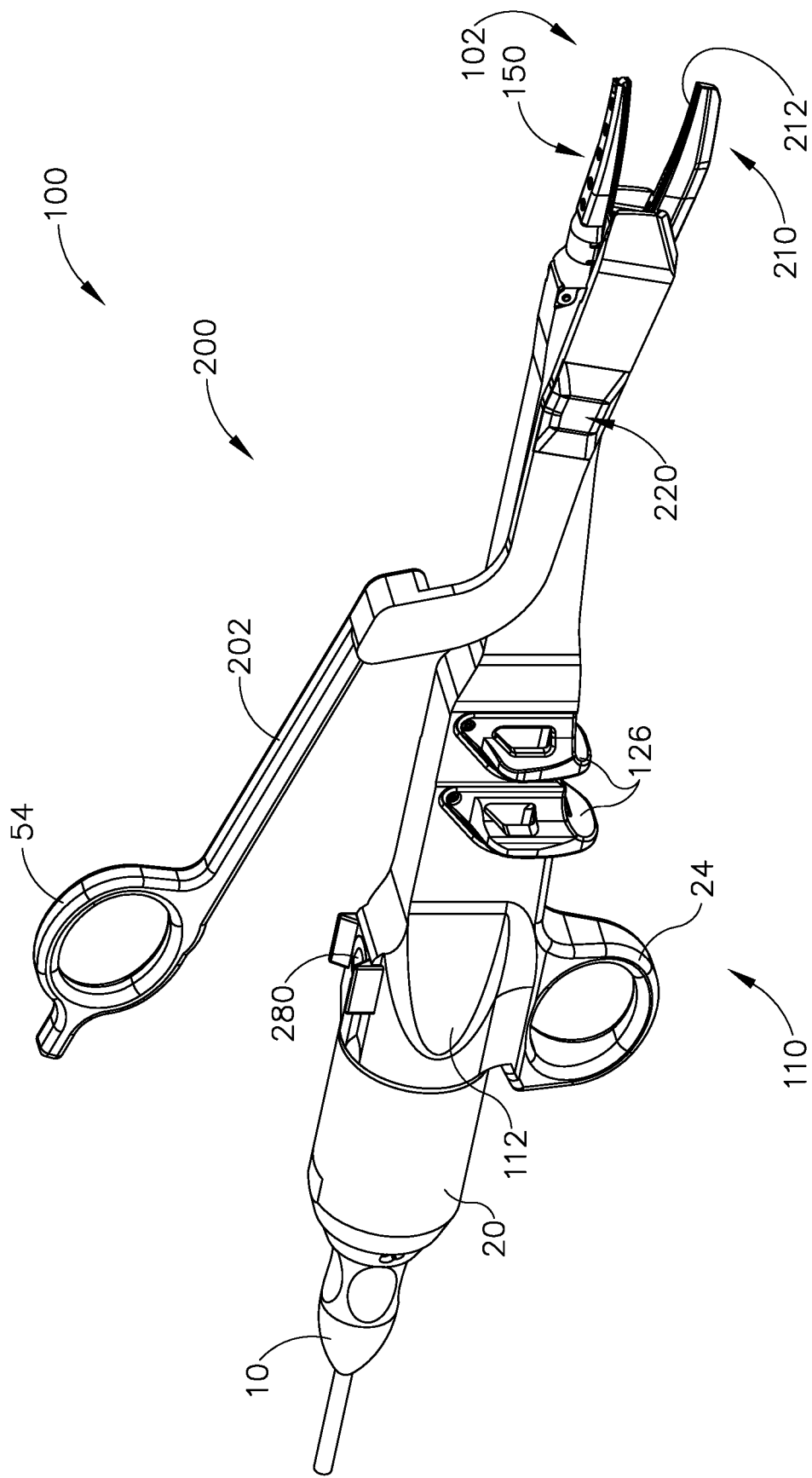
FIG. 1B depicts a perspective view of the instrument of FIG. 1A, with the end effector in an open configuration.

FIG. 22B corresponds to the position of data communication assembly (240) relative to electrical contacts (266) when end effector (102) is on the open configuration (e.g., as shown in FIGS. 1B and 2B). As can be seen, when end effector (102) is in the open configuration, clamp arm assembly (200) is pivoted such that each electrical connector (242) of data communication assembly (240) is in electrical communication with the proximal most position of each corresponding electrical contact (266) of handle assembly (110). Accordingly, when end effector (102) is in the open configuration (and pivotal states between the open configuration and closed configuration), electrical continuity remains between electrical connectors (242) of clamp arm assembly (200) and electrical contacts (266) of handle assembly (110). In the present example, it should be understood that the "open position" of end effector (102) corresponds to the maximum recommended end effector (102) opening during a surgical procedure. Although this is described herein as a maximum recommended configuration, it should be understood that end effector (102) may be optionally opened a greater distance (particularly for decoupling clamp arm assembly (200) from handle assembly (110)). As will be described in greater detail below, in some examples end effector (102) or other components of instrument (10) include detents or other features suitable to alert an operator to being in the properly open configuration.

FIG. 22C corresponds to the position of data communication assembly (240) relative to electrical contacts (266) when end effector (102) is in a fault configuration—where clamp arm assembly (200) is opened beyond the proper open configuration described above. As can be seen, when end effector (102) is in a fault configuration, clamp arm assembly (200) is pivoted such that each electrical connector (242) of data communication assembly (240) is in an open circuit state relative to each corresponding electrical contact (266) of handle assembly (110). Thus, when end effector (102) is in a fault configuration, electrical continuity between electrical connectors (242) of clamp arm assembly (200) and electrical contacts (266) of handle assembly (110) is eliminated. In the present example, this condition signals to generator (5) that end effector (102) has been opened into an undesirable range. In some examples, this triggers an alarm or automatic shutoff of instrument (10). In addition, such a condition may be used in some examples to indicate an error condition, such as clamp arm assembly (200) not being properly coupled to handle assembly (110). In still further examples, such a condition may be used to indicate removal of clamp arm assembly (200) to indicate to generator (5) that clamp arm assembly (200) has been used for a surgical procedure. Such an event may then be stored in non-volatile memory of electrical circuit (248) to deter reuse of clamp arm assembly (200) with other instruments (10) or the same instrument (10). Of course, any other suitable use of such a condition may be provided as will be apparent to those of ordinary skill in the art in view of the teachings herein.

3. Exemplary Transfer of RF Energy from Handle Assembly to Clamp Arm Assembly

Figure 23:
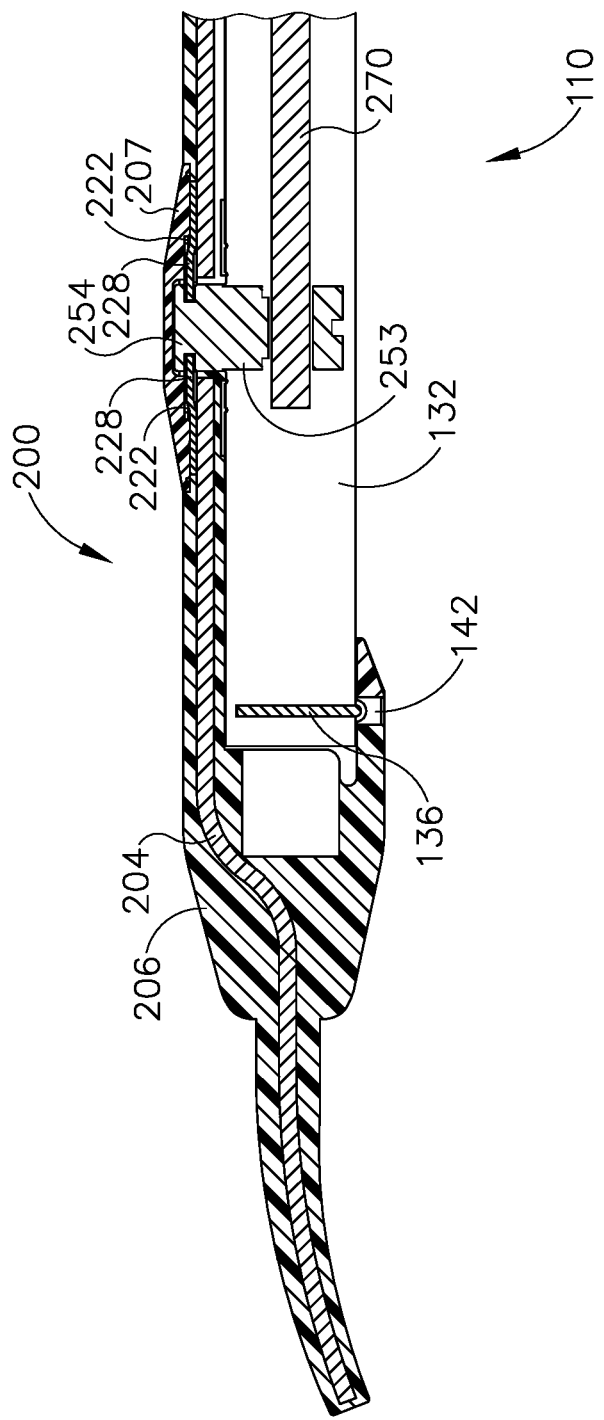
FIG. 23 depicts a partial cross-sectional view of the instrument of FIG. 1A, taken along line 23-23 of FIG. 19C.

FIG. 23 shows an exemplary current path for coupling assembly (220). As can be seen, structural core (204) of body (202) extends through body (202) to the distal end of body (202). Although not shown, it should be understood that, at the distal end of body (202), structural core (204) is coupled to electrode (218) by resistance welding as described above. Thus, structural core (204) is configured to be in electrical communication with electrode (218).

As described above, coupling plate (222) of coupling assembly (220) is secured to body (202) to be in electrical communication with structural core (204). Thus, coupling plate (222) is configured to be in electrical communication with electrode (218) via structural core (204). As also described above, attachment member (252) of coupling assembly (250) is also in electrical communication with coupling plate (222). Thus, the mechanical coupling between attachment member (252) and coupling plate (222) also provides an electrical coupling between clamp arm assembly (200) and handle assembly (110). Because coupling plate (222) is configured to be in electrical communication with electrode (218), the electrical coupling between attachment member (252) and coupling plate (222) is configured to permit electrical communication between handle assembly (110) and electrode (218).

Attachment member (252) of handle assembly (110) is in electrical communication with generator (5) via contact (270). In particular, contact (270) extends longitudinally through handle assembly (110) and is configured to be electrically coupled to attachment member (252). In some examples, contact (270) comprises a printed circuit board with one or more electrical traces disposed therein. In such examples, at least one trace is coupled to attachment member (252) (e.g., soldered) to be in electrical communication with attachment member (252). In some other examples, contact (270) is simply configured as a wire.

Although not shown, it should be understood that contact (270) also includes one or more discrete conductors that are in electrical communication with electrical contacts (266) of handle assembly (110). Such conductors similarly extend through the interior of handle assembly (110) and provide electrical communication between electrical contacts (266)

and generator (5). Electrical communication between contact (270) and electrical contacts (266) is generally configured to permit data communication assembly (240) to communicate data to generator (5). By way of example only, clamp pad assembly (210) may comprise one or more sensors that are operable to sense characteristics of clamp pad assembly (210), and/or tissue; and data from such one or more sensors may be communicated to generator (5) via contact (270) and electrical contacts (266). In addition or in the alternative, clamp pad assembly (210) may comprise an EEPROM in or similar device in communication with contacts (266) that enables generator (5) to determine that clamp arm assembly (200) is only used once (e.g., generator (5) may disable functionality and/or provide an error message when generator (5) determines that clamp arm assembly (200) has been previously used, based on data from an EEPROM communicated via contact (270) and electrical contacts (266)). Additionally, in some examples, at least one electrical contact (266) is configured to form a bridge circuit with the electrical communication path of electrode (218), structural core (204), coupling plate (222), and attachment member (252). In such examples, this circuit may be desirable because such a bridge circuit may permit generator (5) to detect when there is suitable electrical continuity to complete an RF energy circuit path before tissue is present to complete the RF energy circuit between blade (152) and electrode (218).

E. Exemplary Alternative Coupling Assembly

FIG. 24 shows an exemplary alternative coupling assembly (320) that may be readily incorporated into clamp arm assembly (200) of instrument (10). Unless otherwise noted herein, it should be understood that coupling assembly (320) is substantially the same as coupling assembly (220) described above. For instance, like with coupling assembly (220), coupling assembly (320) comprises a coupling plate (322) and a retaining bracket (330). Retaining bracket (330) is substantially the same as retraining bracket (230) described above such that the particular details of retaining bracket will not be repeated herein.

Coupling plate (322), like coupling plate (222), is generally configured to receive at least a portion of handle assembly (110) to selectively couple clamp arm assembly (200) to handle assembly (110). Coupling plate (322) of the present example comprises a generally rectangular base (324). Like coupling plate (222), coupling plate (322) is generally comprised of a conductive metallic or conductive non-metallic material.

Base (324) of coupling plate (322) defines a pair of bracket openings (325) and a single spring opening (326). As with bracket opening (225) described above, bracket openings (325) are generally configured to receive at least a portion of retaining bracket (330) such that retaining bracket (330) and coupling plate (322) are securable to structural core (204) of body (202). Like arm opening (226) described above, spring opening (326) is sized such that at least a portion of handle assembly (110) may extend through base (224).

However, unlike arm opening (226) described above, spring opening (326) is not sized for any structure similar to coupling arms (228) because coupling arms (228) are omitted in the present example. Instead, as will be described in greater detail below, the functional features of coupling arms (228) are replaced with a spring member (328).

Spring member (328) comprises a cylindrical wire with resilient and electrically conductive characteristics. As will be described in greater detail below, spring member (328) is generally configured to be resiliently biased toward the configuration shown in FIG. 24, but also be elastically deformable in response to coupling with handle assembly (110). By way of example only, some merely exemplary materials for cylindrical wire include metals such as steel, aluminum, copper, gold, or aluminum. Alternatively, in some examples spring member (328) comprises a non-metallic conductor having resilient characteristics. Regardless of materials, spring member (328) is bent into a configuration resembling coupling arms (228) described above. However, spring member (328) also forms at least one coil for added resilient characteristics. Although not shown, it should be understood that in some examples base (324) includes protrusions or other features to maintain spring member (328) in the position shown in FIG. 24.

The present example also includes an alternative coupling assembly (350) that is associated with handle assembly (110). It should be understood that coupling assembly (350) of the present example is substantially the same as coupling assembly (250) described above unless otherwise specifically noted herein. For instance, like coupling assembly (250), coupling assembly (350) of the present example includes an attachment member (352) and a plurality of electrical contacts (not shown). The electrical contacts are substantially the same as electrical contacts (266) described above such that the electrical contacts will not be described in further detail herein.

Like attachment member (252) described above, attachment member (352) of the present example comprises a base (not shown), and an attachment portion (354). Base (353) is configured substantially the same as base (253) described above such that the particular details of base (253) will not be described in further detail herein. At the lateral-most end of base (353), the outer diameter of base narrows to define a generally circular channel (356) between base and attachment portion (354). As will be described in greater detail below, channel (356) is configured to receive spring member (328) to couple clamp arm assembly (200) to handle assembly (110).

Attachment portion (354) of the present example is of unitary construction with base (353) such that base (353) and attachment portion (354) are formed of a single component. Attachment portion (354) is disposed laterally of base (353), adjacent to channel (356). Attachment portion (354) is generally cylindrical in shape. However, unlike attachment portion (254), described above, attachment portion (354) omits structures similar to flat portions (258). Instead, attachment portion (354) is generally circular in shape with an annularly chamfered lateral end (358). As will be described in greater detail below, chamfered lateral end (358) is generally configured to promote outward deformation of spring member (328) as clamp arm assembly (200) is inserted onto handle assembly (110).

Figure 25A:
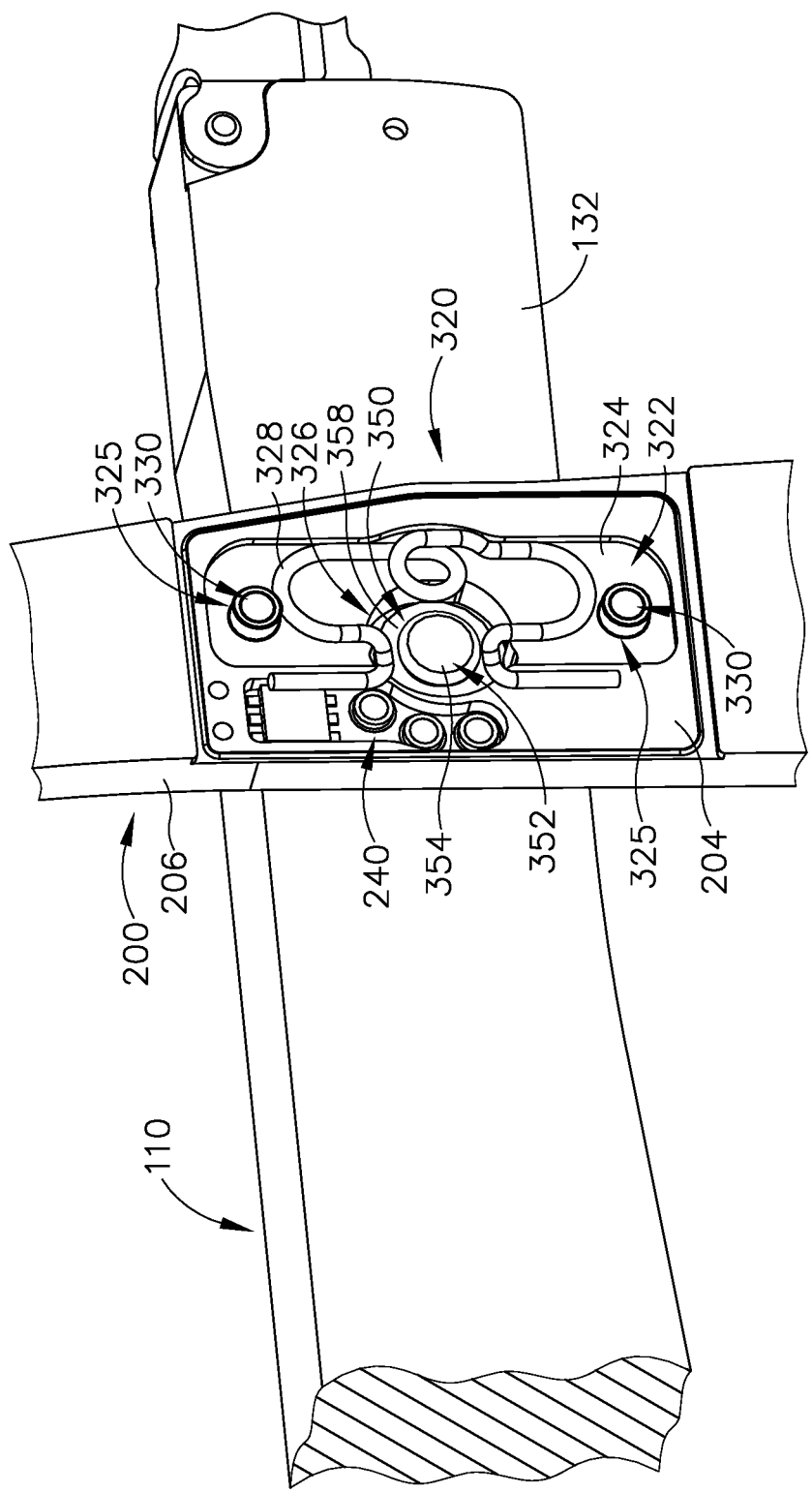
FIG. 25A depicts a partial perspective view of the coupling assembly of FIG. 24 incorporated into the instrument of FIG. 1A, with the modified clamp arm in a first transverse position in relation to the handle assembly.
Figure 25B:
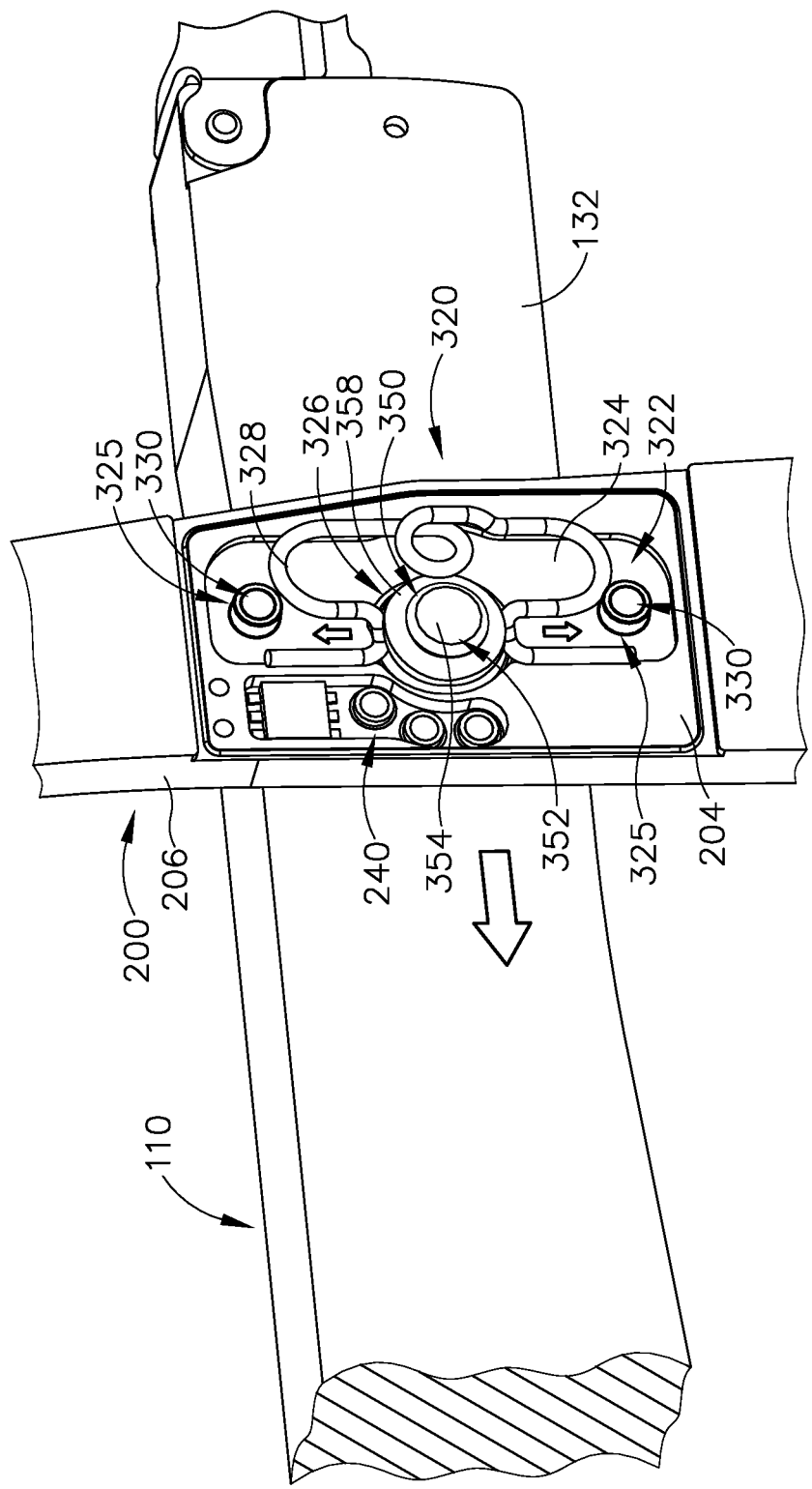
FIG. 25B depicts a partial perspective view of the coupling assembly of FIG. 24 incorporated into the instrument of FIG. 1A, with the modified clamp arm in a second transverse position in relation to the handle assembly.
Figure 25C:
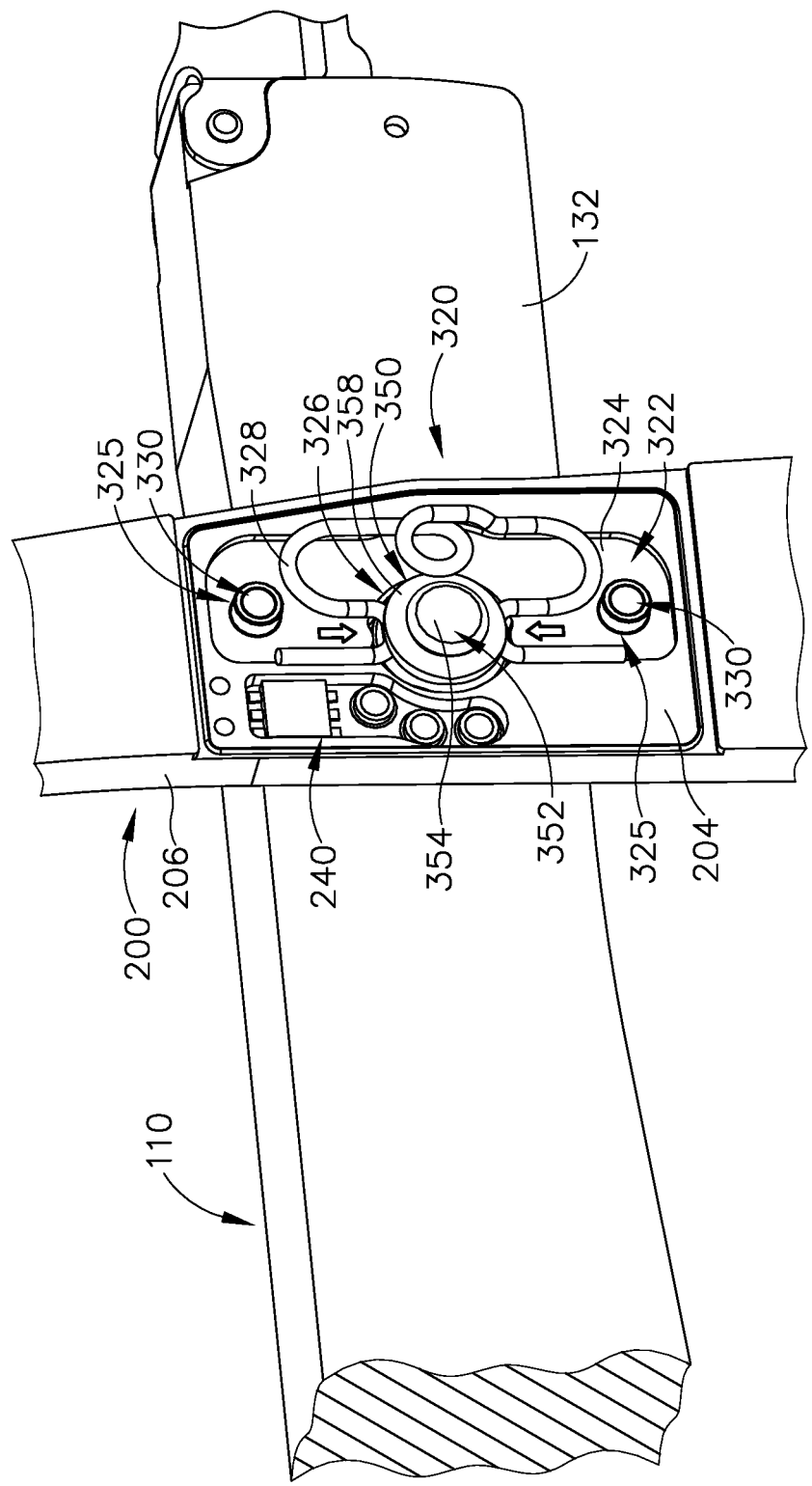
FIG. 25C depicts a partial perspective view of the coupling assembly of FIG. 24 incorporated into the instrument of FIG. 1A, with the modified clamp arm in a third transverse position in relation to the handle assembly.

FIGS. 25A-25C show an exemplary operation for attaching clamp arm assembly (200) to handle assembly (110) when equipped with respective coupling assemblies (320, 350). It should be understood that the procedure for coupling is generally substantially similar to the procedure described above with respect to coupling assemblies (220, 250), except where otherwise specifically noted herein. For instance, as shown in FIG. 25A and as similarly described above, clamp arm assembly (200) is initially oriented perpendicularly relative to handle assembly (110) and laterally offset from handle assembly (110). However, unlike with coupling assembly (220) described above, it should be understood that coupling assembly (320) may be oriented at numerous other alternative angular positions relative to handle assembly (110) at the stage shown in FIG. 25A. In particular, because attachment portion (354) is generally cylindrical in shape and spring member (328) is generally deformable, spring member (328) may engage attachment portion (354) at any suitable angular position about attachment portion (354) (provided clamp arm assembly (200) and handle assembly (110) remain laterally aligned along the longitudinal axis of attachment portion (354)).

To couple clamp arm assembly (200) to handle assembly (110), an operator merely translates clamp arm assembly (200) transversely toward handle assembly (110), along the longitudinal axis of attachment portion (354), as shown in FIG. 25B. This translation causes chamfered lateral end (358) of attachment portion (354) to engage spring member (328) of coupling assembly (320). Engagement between chamfered lateral end (358) and spring member (328) as clamp arm assembly (200) is translated as shown in FIG. 25B causes spring member (328) to deform outwardly. Spring member (328) continues to deform outwardly until spring member (328) continues past attachment portion (354).

Once spring member (328) has been moved past attachment portion (354), spring member (328) enters channel (356) and elastically returns to its initial position as shown in FIG. 25C. Once spring member (328) returns to its initial position, clamp arm assembly (200) is coupled to handle assembly (110) and instrument (10) may be used by an operator as described herein. If an operator should desire to decouple clamp arm assembly (200) from handle assembly (110), clamp arm assembly (200) is merely pulled transversely from handle assembly (110) with sufficient force to deform spring member (328) outwardly, thereby removing spring member (328) from channel (356).

F. Exemplary Alternative Clamp Arm Assembly

FIGS. 26A-31 show an alternative clamp arm assembly (400) connecting to an alternative shaft assembly (530) and blade assembly (550). It should be understood that clamp arm assembly (400), shaft assembly (530), and blade assembly (550) are substantially the same as clamp arm assembly (200), shaft assembly (130), and blade assembly (150) as mentioned above, except for the differences described below. Therefore, is should be understood that clamp arm assembly (400), shaft assembly (530) and blade assembly (550) may substitute clamp assembly (200), shaft assembly (130), and blade assembly (150) in instrument (100).

Shaft assembly (530) includes an outer sheath (532) and a t-nut (502) extending laterally from outer sheath (532). T-nut (502) is dimensioned to receive clamp arm assembly (400), and clamp arm assembly (400) is configured to rotate about axis defined by t-nut (502), as will be described in greater detail below.

Clamp arm assembly (400) includes a body (402), a coupling assembly (420), and a clamp pad assembly (410). Body (402) and clamp pad assembly (410) are substantially similar to body (202) and clamp pad assembly (210) described above. Coupling assembly (420) is substantially similar to coupling assembly (220) described above except for the differences described below.

Coupling assembly (420) includes a pivot base (430), a pivot lock (440), and a pivot cap (460). Pivot base (430) includes a recess (432) for receiving pivot lock (440) and pivot cap (460), a pair of protrusions (434), and an elongate opening (436) for receiving t-nut (502). Pivot lock (440) includes a pair of coupling openings (442), a resilient lock (444), and an elongate opening (446) for receiving t-nut (502). Pivot cap (460) includes an unlocking feature (464) and an elongate opening (466) for receiving t-nut (502). While it is shown that coupling assembly (420) has three individual pieces of pivot base (430), pivot lock (440), and pivot cap (460), it is contemplated that coupling assembly (420) could instead be formed by just one unitary piece, two pieces, four pieces, or more.

Figure 26A:
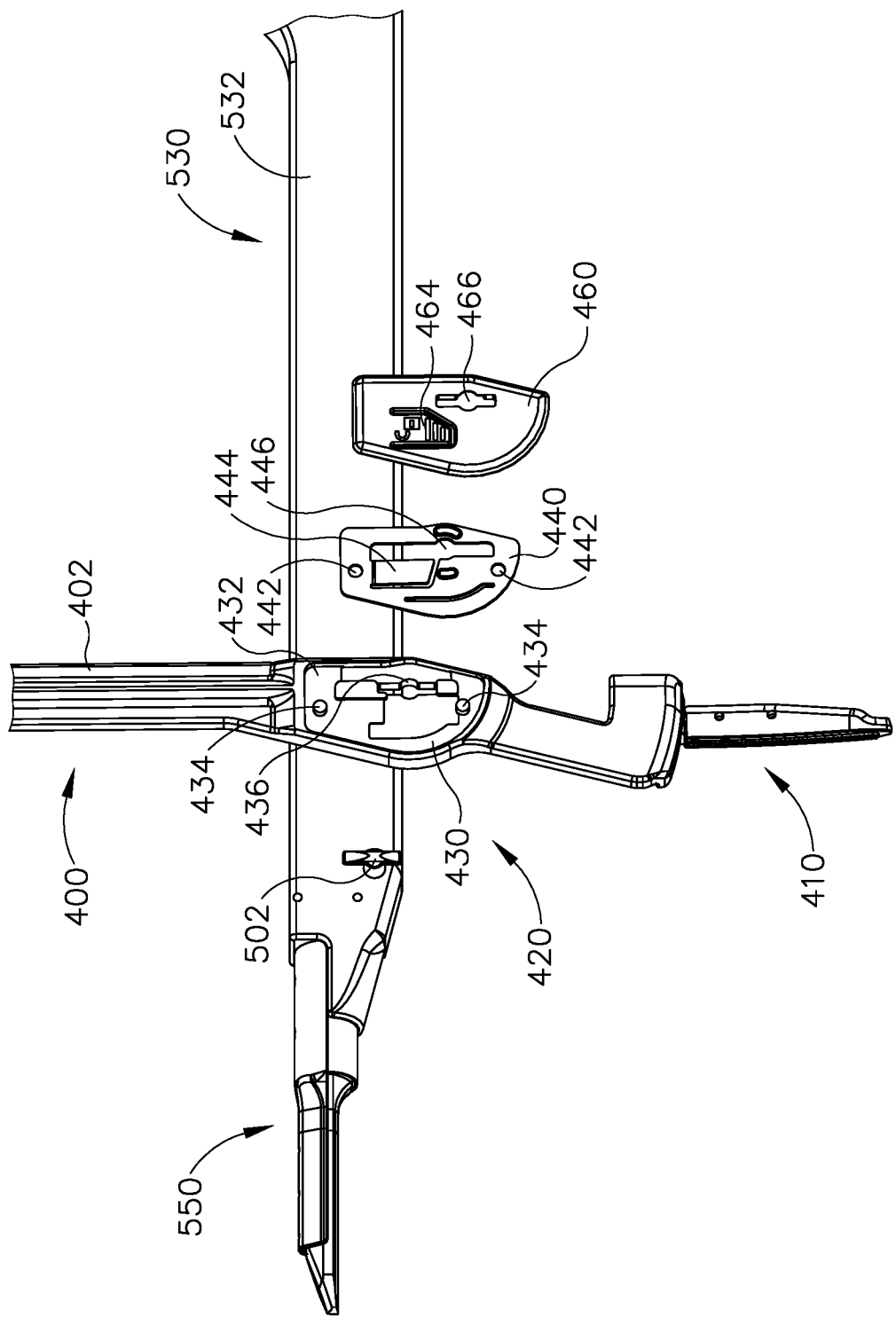
FIG. 26A depicts a side elevational view of a distal portion of an exemplary alternative surgical instrument, with a clamp arm separated from a handle assembly.
Figure 26B:
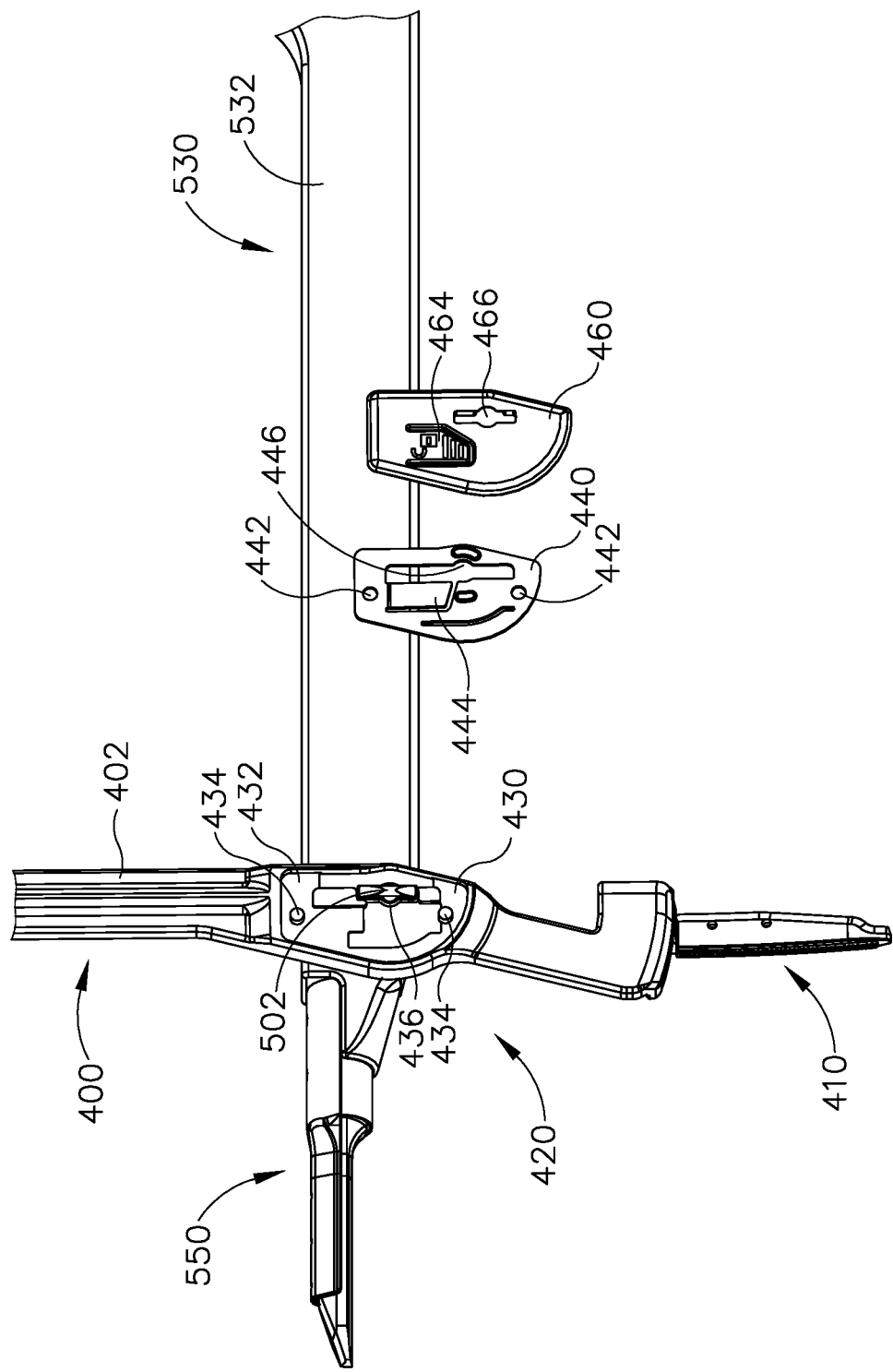
FIG. 26B depicts a side elevational view of the distal portion of the instrument of FIG. 26A, with the clamp arm in a first state of assembly with the handle assembly.
Figure 26C:
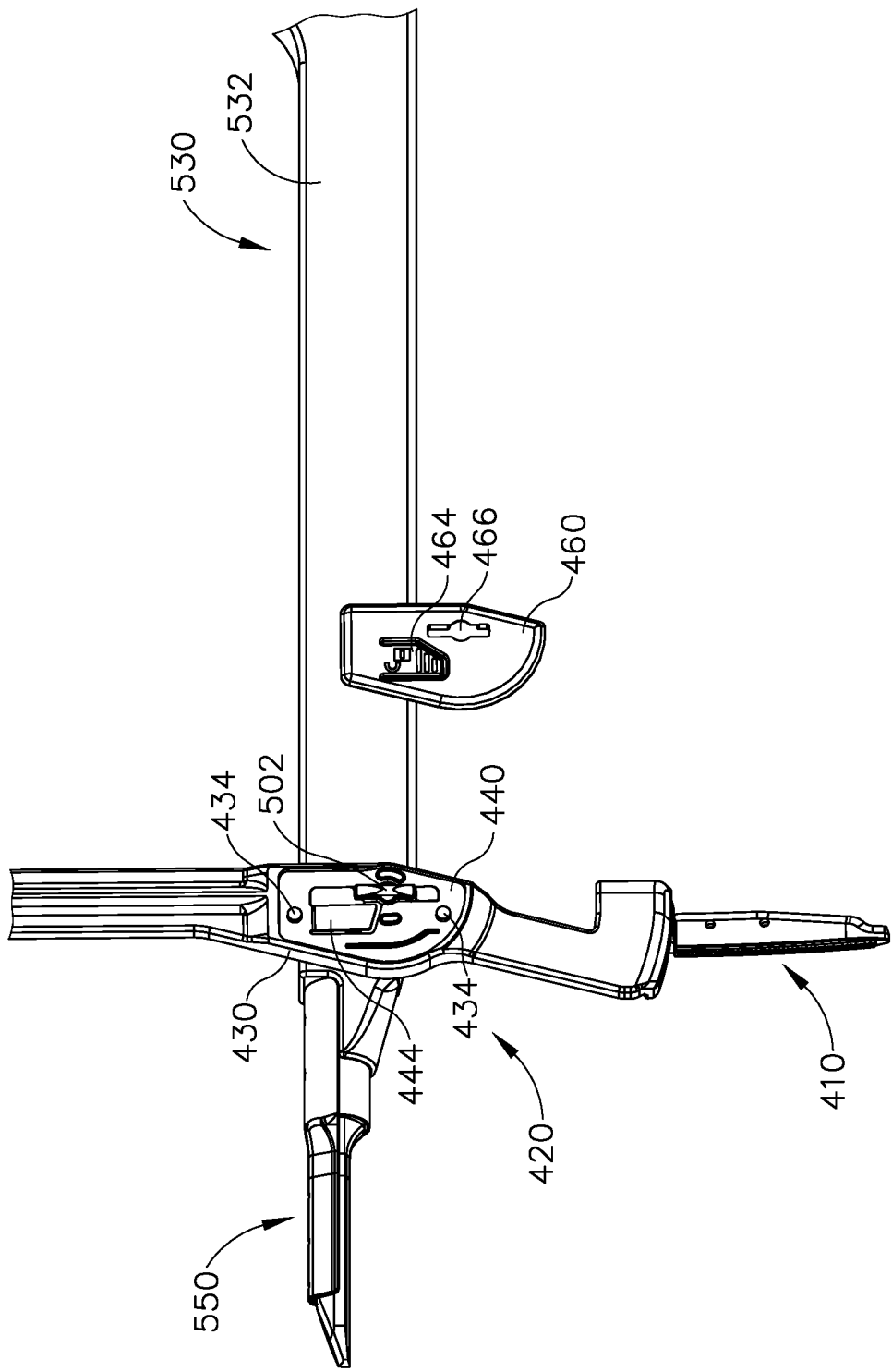
FIG. 26C depicts a side elevational view of the distal portion of the instrument of FIG. 26A, with the clamp arm in a second state of assembly with the handle assembly.
Figure 26D:
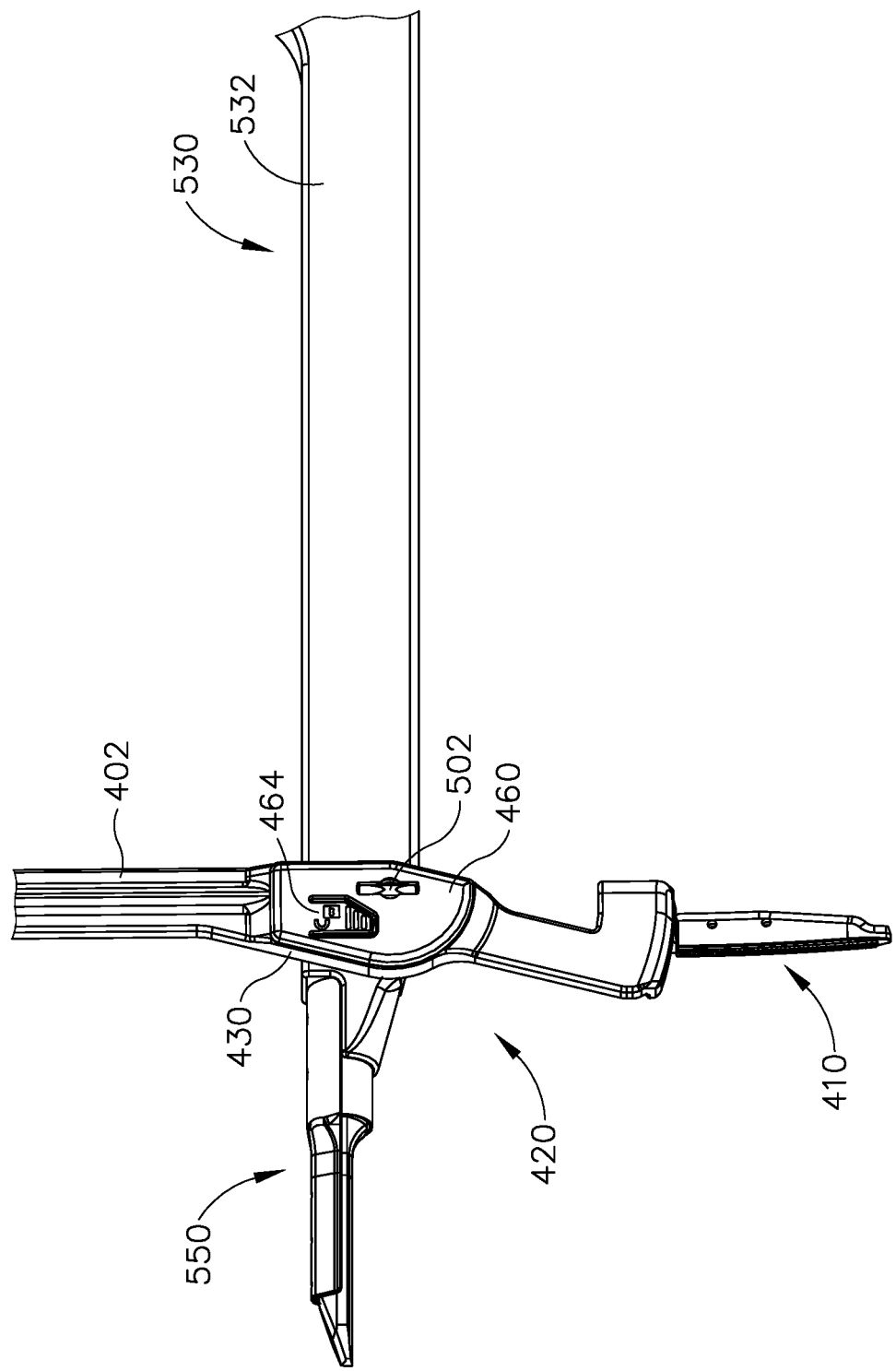
FIG. 26D depicts a side elevational view of the distal portion of the instrument of FIG. 26A, with the clamp arm in a third state of assembly with the handle assembly.

As shown in FIGS. 26A-26B, body (402) of clamp arm assembly (400) is initially oriented perpendicular to outer sheath (532) and laterally offset from outer sheath (532), so that t-nut (502) is aligned with complementary openings (436, 446, 466). As shown in FIG. 26B, pivot base (430) is then translated transversely toward outer sheath (532) so that t-nut (502) is inserted into complementary opening (436). As shown in FIG. 26C, pivot lock (440) is then translated transversely toward pivot base (430) so that protrusions (434) and couplings openings (442) mate. At this point, pivot lock (440) is secured within the confines of recess (432) while t-nut (502) in also inserted into complementary opening (446). Then, as shown in FIG. 26D, pivot cap (460) is translated transversely into position on top of both pivot base (430) and pivot lock (440) such that complementary recess (460) aligns with t-nut (502). Pivot cap (460) may be secured to pivot base (430) through a snap fit or any other suitable means known in the art in view of the teachings herein.

While it is shown in FIGS. 26A-26D that pivot base (430), pivot lock (440), and pivot cap (460) are each installed relative to shaft assembly (530) separately, it should be understood that pivot lock (440) and pivot cap (460) may be pre-installed on pivot base (430) prior to assembling coupling assembly (420) with shaft assembly (530). Thus, the series shown in FIGS. 26A-26C should not be viewed as an exhaustive representation of how clamp arm assembly (400) may be secured to outer sheath (532). Instead, the series shown in FIGS. 26A-26C may be viewed as simply showing the relationships between the components of coupling assembly (420).

Figure 26E:
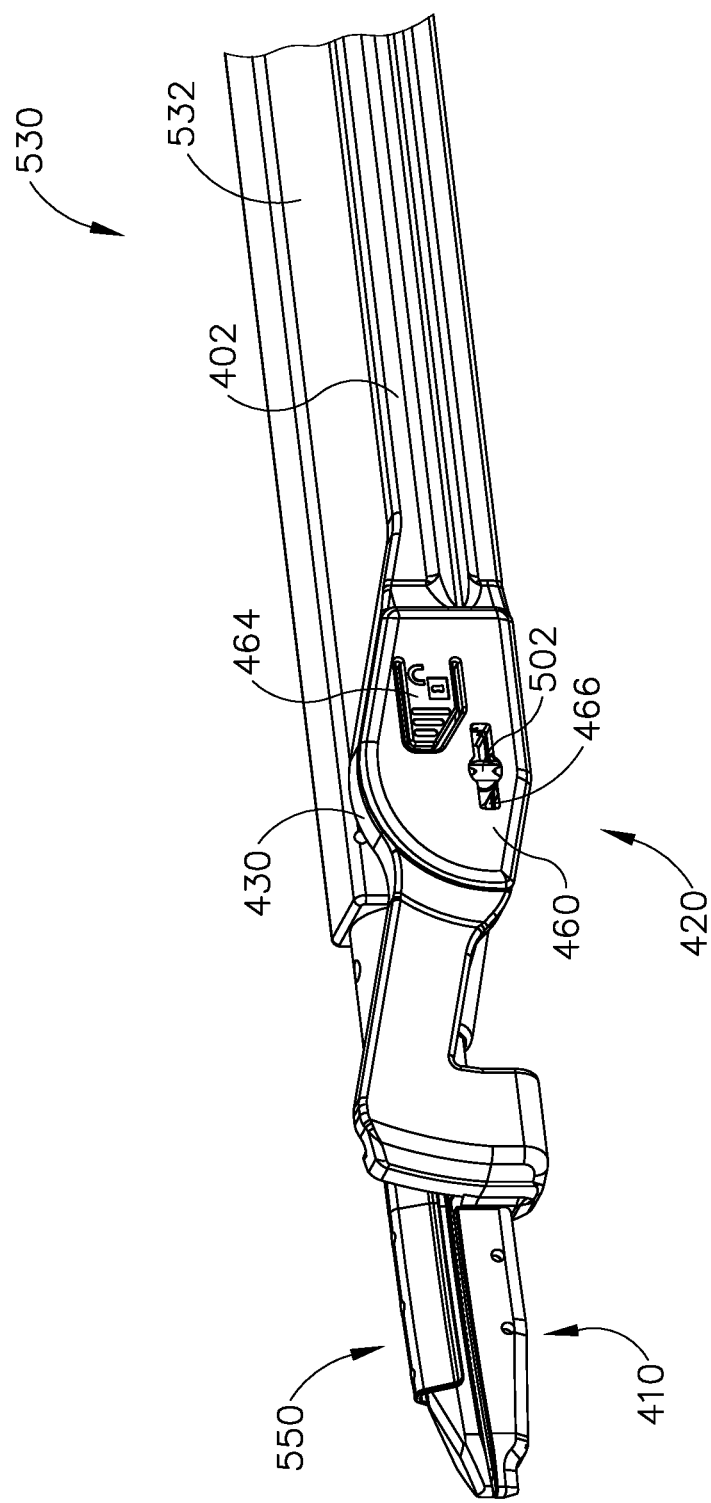
FIG. 26E depicts a perspective view of the distal portion of the instrument of FIG. 26A, with the clamp arm in a fourth state of assembly with the handle assembly.

As shown in FIG. 26E, once t-nut (502) is inserted through complementary openings (436, 446), body (402) may be rotated toward shaft assembly (530). Due to t-nut (502) and complementary openings (436, 446) no longer being aligned, coupling assembly (420) is now rotatably coupled to shaft assembly (530) via t-nut (502), such that t-nut (502) prevents clamp arm assembly (400) from moving laterally along the longitudinal axis of t-nut (502). However, at this point, clamp arm assembly (400) may rotate about the axis defined by t-nut (502) to open and close clamp pad assembly (410) relative to blade assembly (550). Clamp arm assembly (400) and shaft assembly (500) may only be decoupled when t-nut (502) and complementary openings (436, 446, 466) are aligned as shown in FIGS. 26A-26D.

Figure 28A:
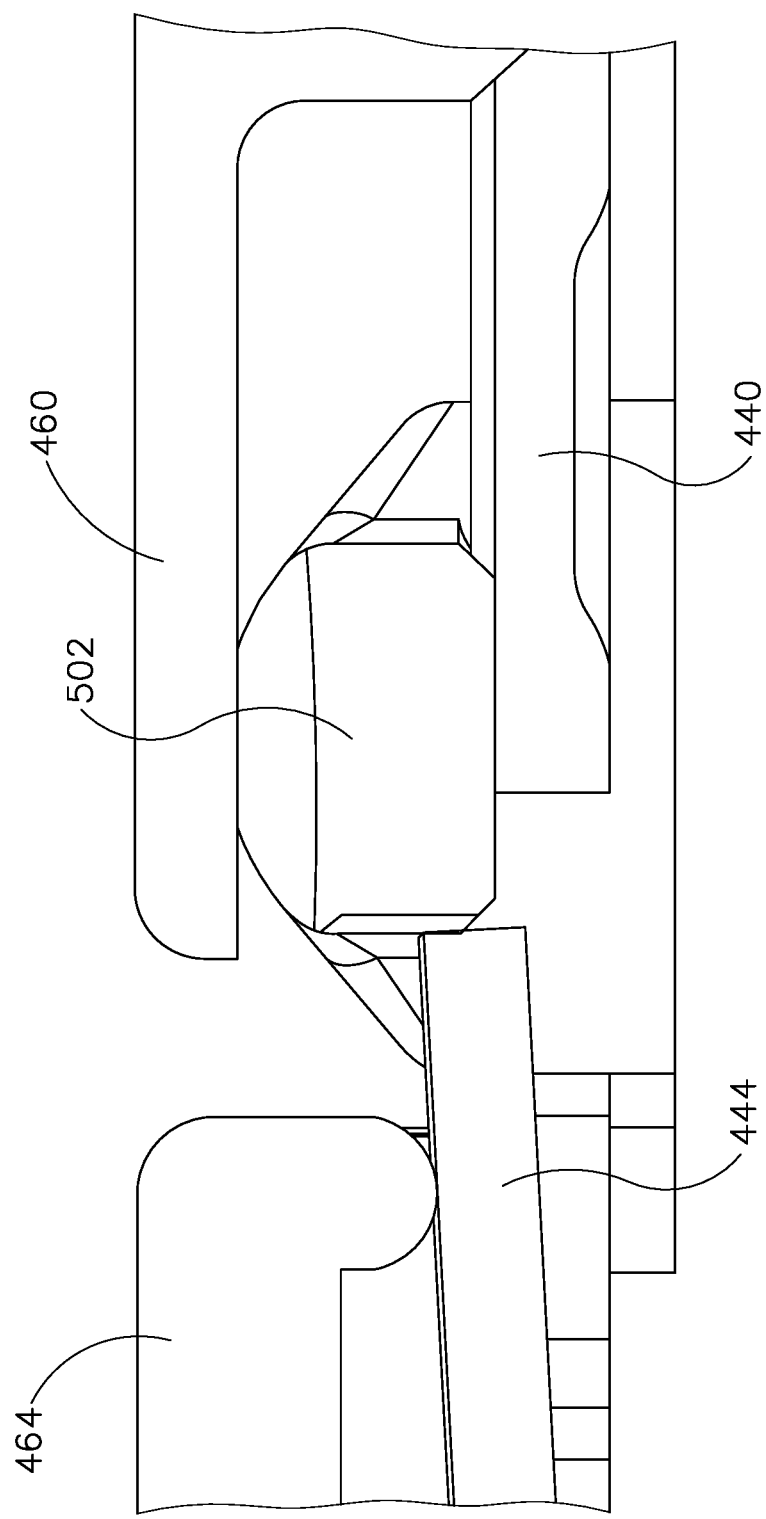
FIG. 28A depicts a cross-sectional top view of a locking assembly of the instrument of FIG. 26A, with the lock in a locking position.
Figure 28B:
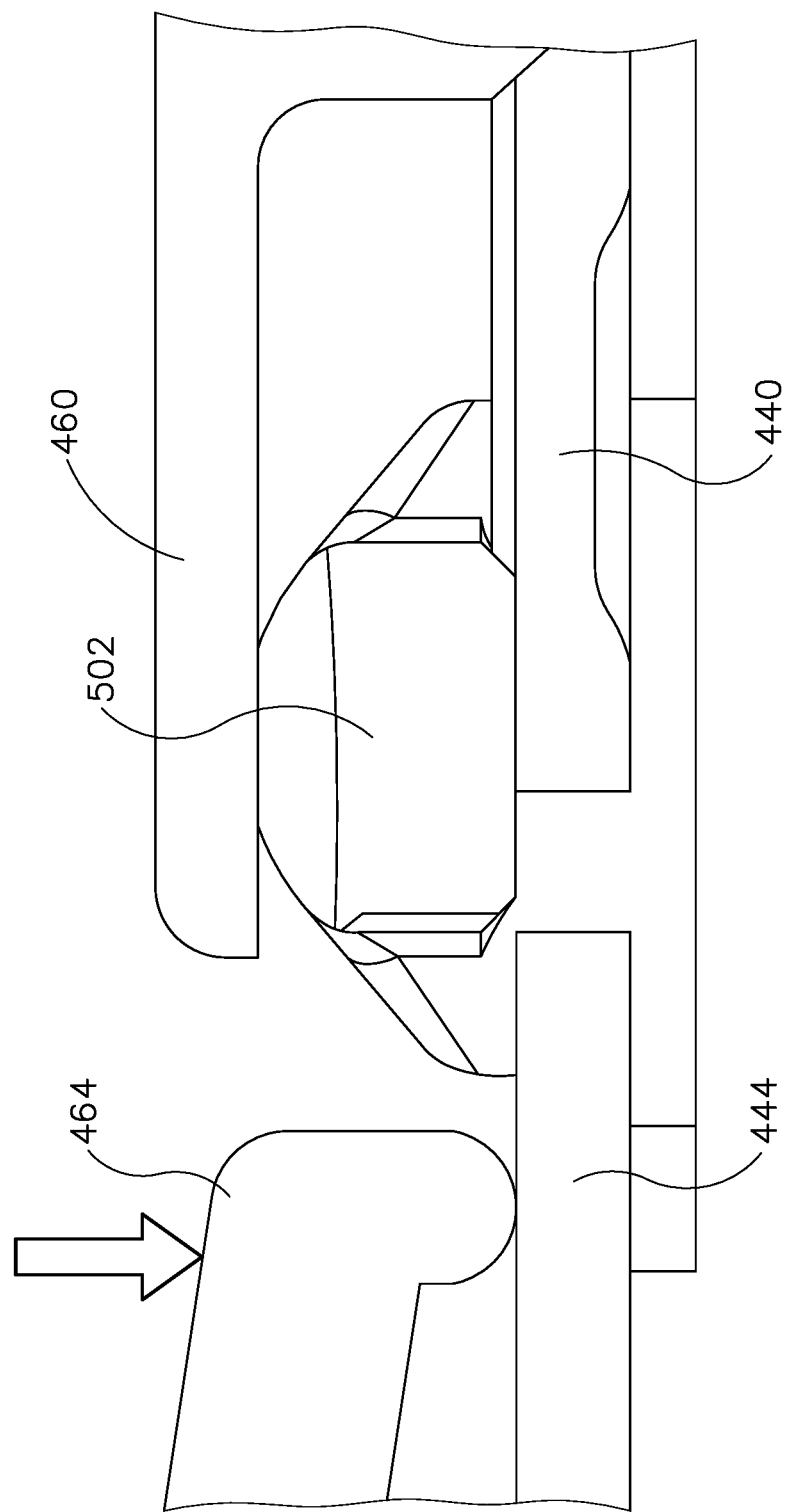
FIG. 28B depicts a cross-sectional top view of a locking assembly of the instrument of FIG. 26A, with the lock deflected to an unlocking position.

It should be understood, that when clamp arm assembly (400) is rotated from the position shown in FIG. 26D to the position shown in FIG. 26E, the bottom surface of t-nut (502) makes contact with the top surface of resilient lock (444), thereby flexing resilient lock (444) toward recess (432). Once the bottom surface oft-nut (502) no longer engages the top surface of resilient lock (444), resilient lock (444) springs back to its natural position, as shown in FIG. 28A.

Figure 27A:
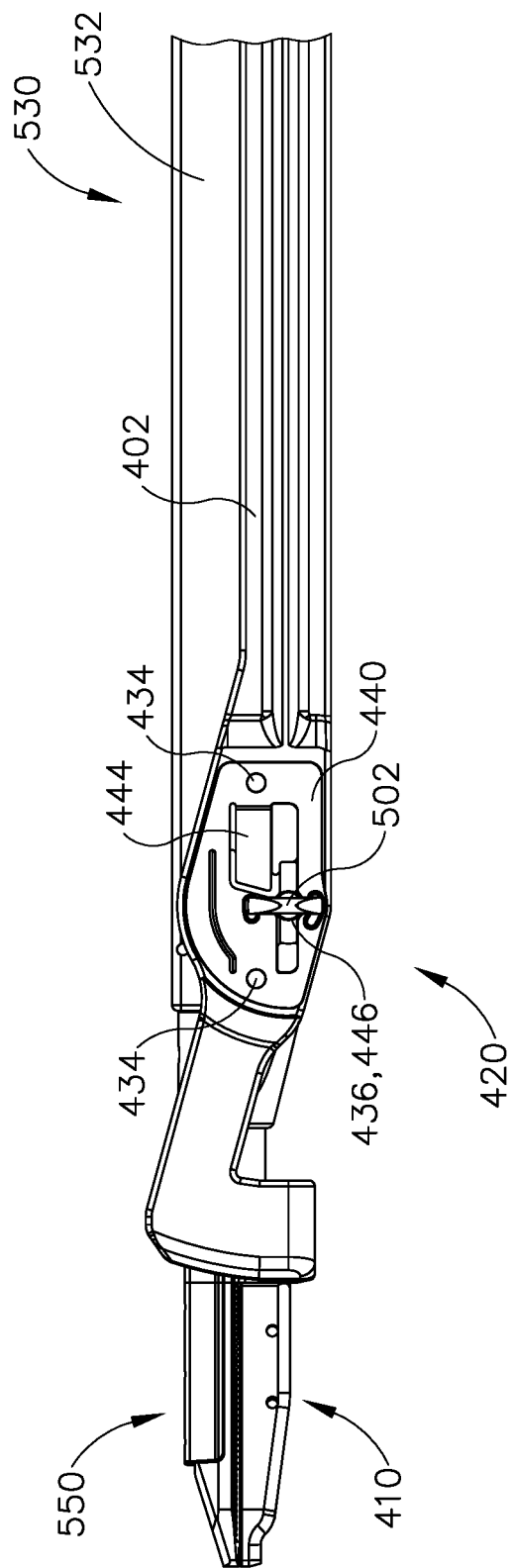
FIG. 27A depicts a side elevational view of the distal portion of the instrument of FIG. 26A, with a pivot cap omitted, and with the clamp arm in a closed position.
Figure 27B:
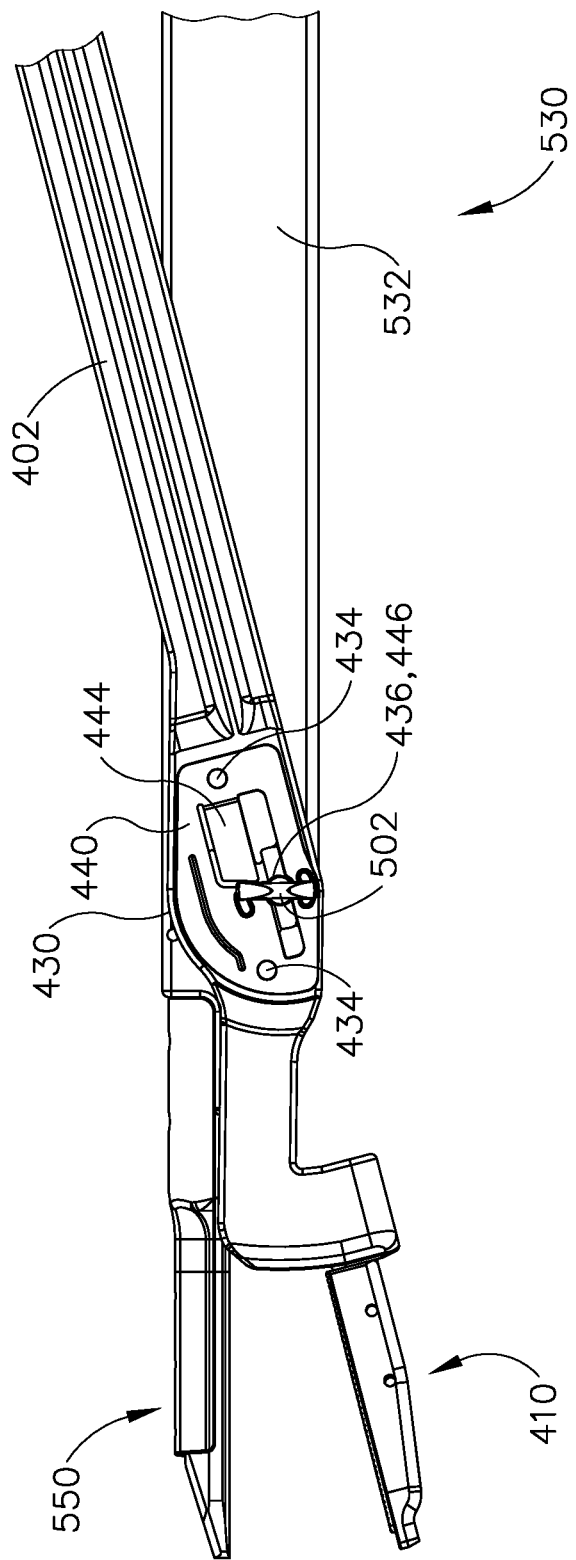
FIG. 27B depicts a side elevational view of the distal portion of the instrument of FIG. 26A, with the pivot cap omitted, and with the clamp arm in a first open position as restricted by a lock.

Resilient lock (444) extends outwardly from the rest of pivot lock (440), toward pivot cap (460). As shown in FIGS. 27A-27B, resilient lock (444), in its natural position, may engage t-nut (502) if clamp arm assembly (400) is rotated to a predetermined locking angle. T-nut (502) is rotationally fixed about its own longitudinal axis relative to outer sheath (532). Therefore, interaction between t-nut (502) and resilient lock (444) limits the rotation of clamp arm assembly (400) when resilient lock (444) is in its natural position.

Resilient lock (444) thus restricts the degree to which clamp pad assembly (410) may be pivoted away from blade assembly (550).

Figure 27C:
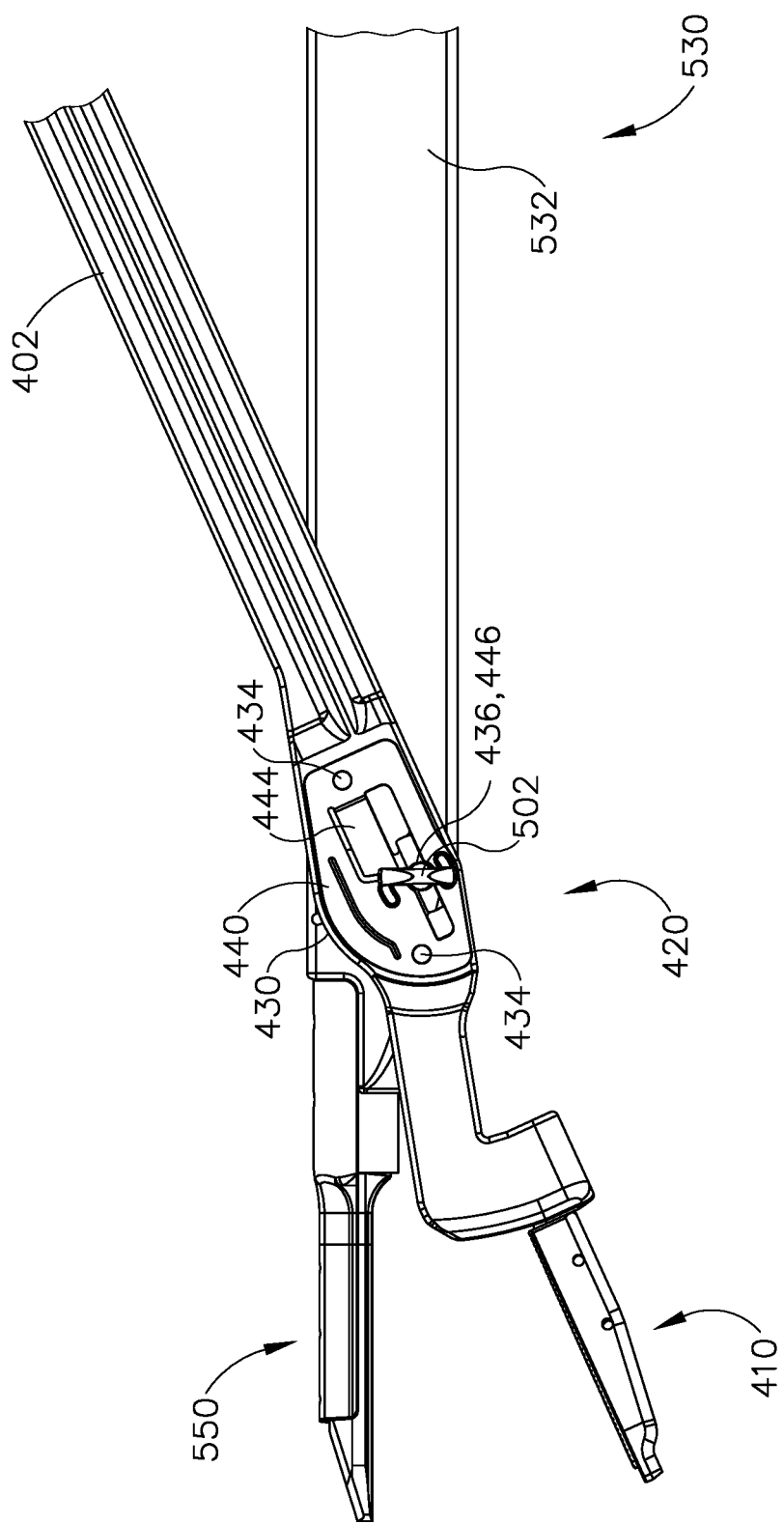
FIG. 27C depicts a side elevational view of the distal portion of the instrument of FIG. 26A, with the pivot cap omitted, and with the lock deflected to enable the clamp to pivot beyond the first open position.
Figure 27D:
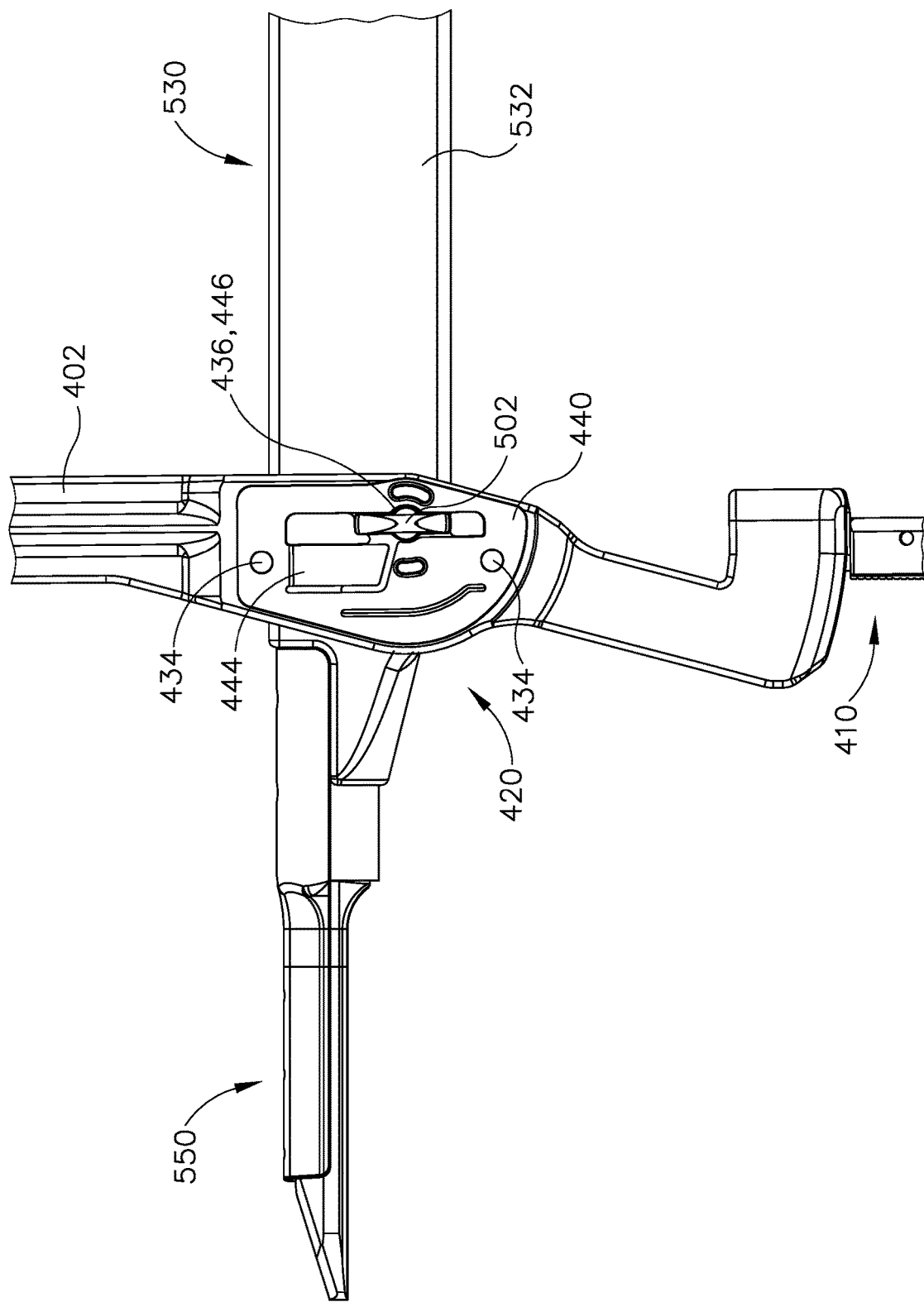
FIG. 27D depicts a side elevational view of the distal portion of the instrument of FIG. 26A, with the pivot cap omitted, and with the clamp arm pivoted to a removal position.

Pivot cap (460) includes unlocking feature (464). Unlocking feature (464) is also resilient, but is biased toward a position that is aligned with the rest of pivot cap (460) as shown in FIG. 28A. As shown in the transition from FIG. 28A to FIG. 28B, an operator may press unlocking feature (464) toward pivot lock (440), thereby forcing unlocking feature (464) to engage resilient lock (444). As such, resilient lock (444) will then flex to be aligned with the rest of pivot lock (440). Once resilient lock (444) is aligned with the rest of pivot lock (440), resilient lock (444) is no longer positioned to engage t-nut (502), and the operator may thus rotate clamp arm assembly (400) past the predetermined locking angle. As shown in FIG. 27C, the bottom surface of the head of t-nut (502) may now engage the top surface of resilient lock (444). At this point, t-nut (502) and resilient lock (444) may no longer restrict the angular rotation of clamp arm assembly (400). Therefore, clamp arm assembly (400) may be rotated to the position shown in FIG. 27D, where t-nut (502) is aligned with complementary openings (436, 446, 466). Clamp arm assembly (400) may then be removed from shaft assembly (530) by pulling clamp arm assembly (400) laterally away from shaft assembly (530) along the longitudinal axis fo t-nut (502).

Figure 29:
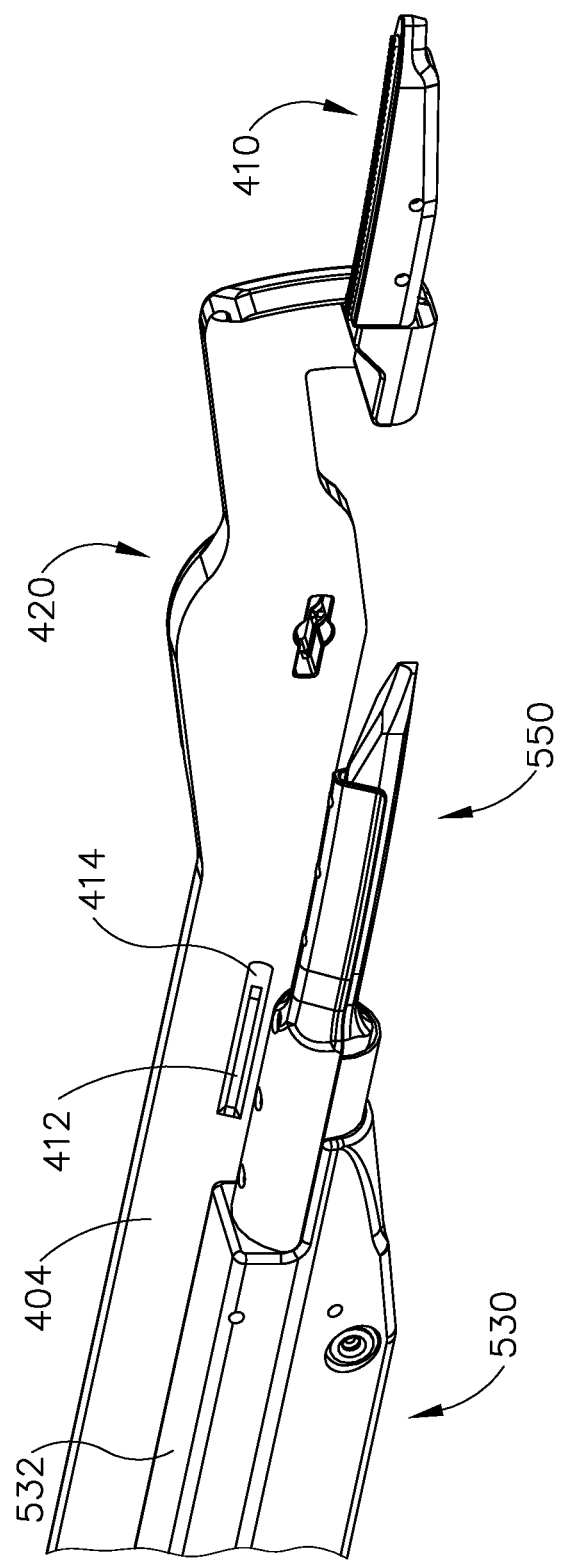
FIG. 29 depicts a perspective view of the distal portion of the instrument of FIG. 26A, with the clamp arm separated from the handle assembly.
Figure 30:
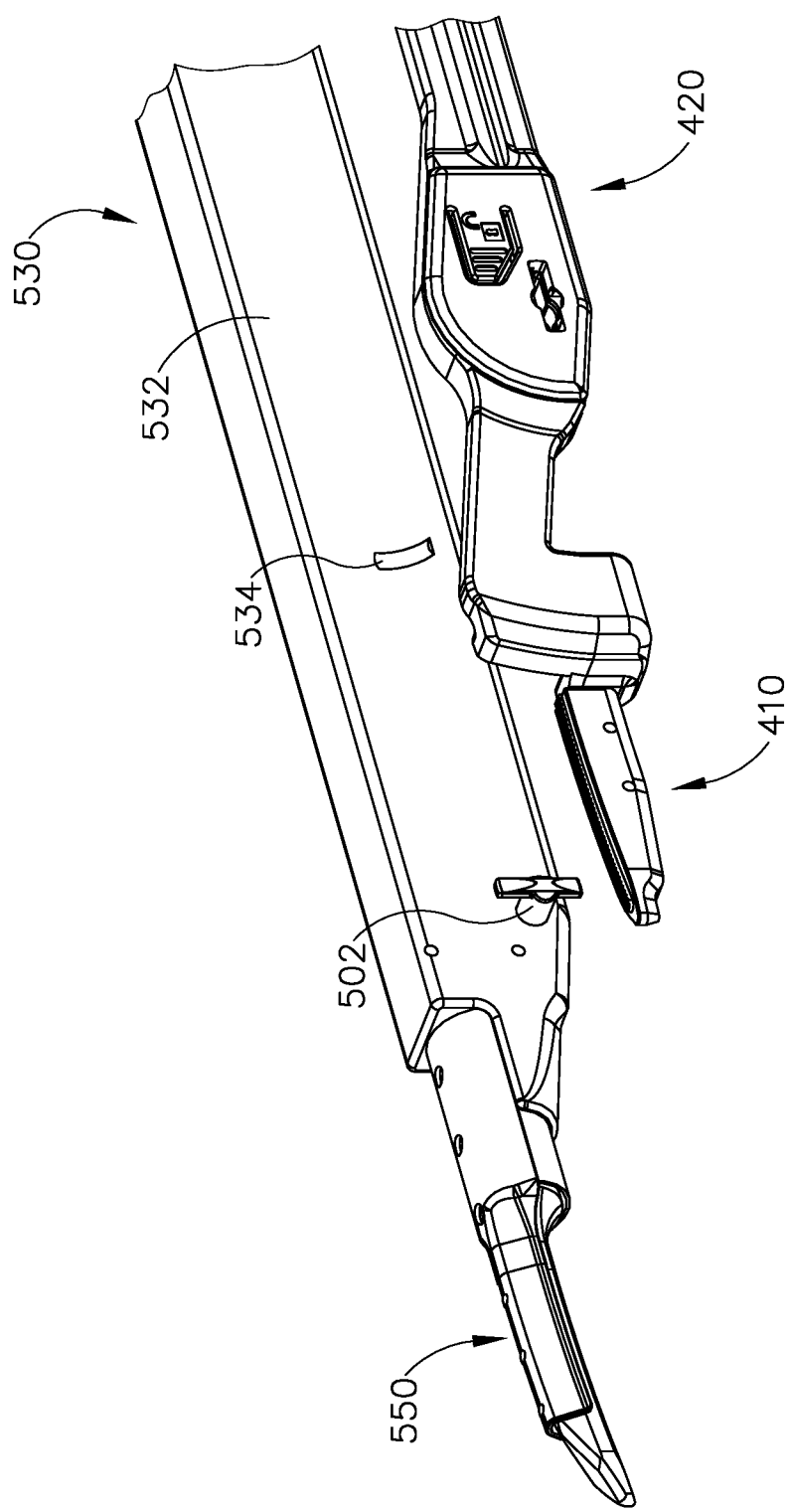
FIG. 30 depicts another perspective view of the distal portion of the instrument of FIG. 26A, with the clamp arm separated from the handle assembly.
Figure 31:
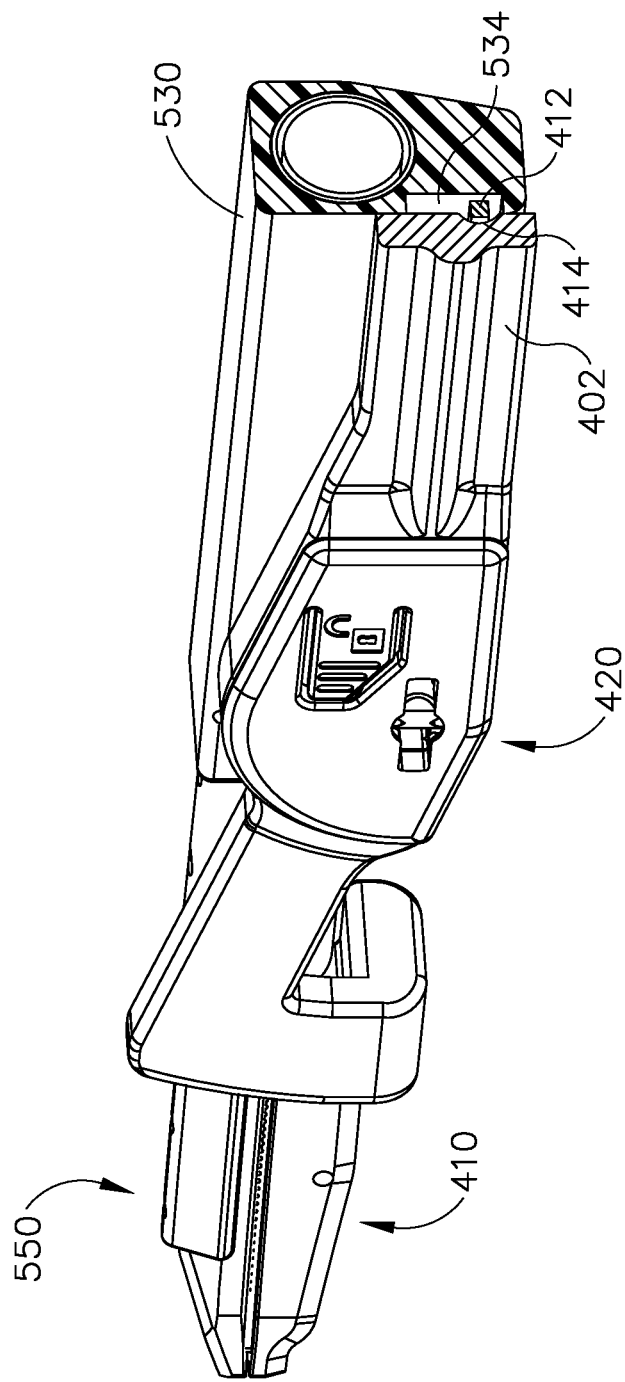
FIG. 31 depicts a cross-sectional perspective view of the distal portion of the instrument of FIG. 26A, showing engagement of detent features.

In some instances, instead of having a predetermined locking angle, it may be desirable to provide tactile feedback to an operator indicating to a user that clamp arm assembly (400) has been rotated past a predetermined angle relative to shaft assembly (530). This way, a user may not necessarily be restricted on the angle formed between clamp pad assembly (410) and blade assembly (550). In such instances, as shown in FIGS. 29 and 31, clamp arm assembly (400) may include a resilient, cantilevered detent (412) slightly protruding from a recess (414). Cantilevered detent (412) may be positioned to align within an arcuate slot (534) formed laterally in outer sheath (532) as shown in FIGS. 30-31. As shown in FIG. 31, cantilevered detent (412) is resiliently biased to slightly protrude from an interior face (404) of clamp arm assembly (400) such that the end of cantilevered detent (412) rests within slot (534). Once clamp arm assembly (400) is pivoted past a predetermined angle, the end of cantilevered detent (412) makes contact with the end of slot (534), thereby providing tactile feedback to an operator (e.g., by providing some degree of resistance to further pivotal movement of clamp arm assembly (400) relative to shaft assembly (530)), indicating that clamp arm assembly (400) has been rotated to the predetermined angle. In some instances, recess (414) allows cantilevered detent (412) to deflect fully into recess (414) to enable the operator to continue pivoting clamp arm assembly (400) relative to shaft assembly (530) beyond the predetermined angle, though the operator must overcome the additional force required to deflect detent (412) fully into recess (414).

G. Exemplary Use of Instrument

Figure 32:
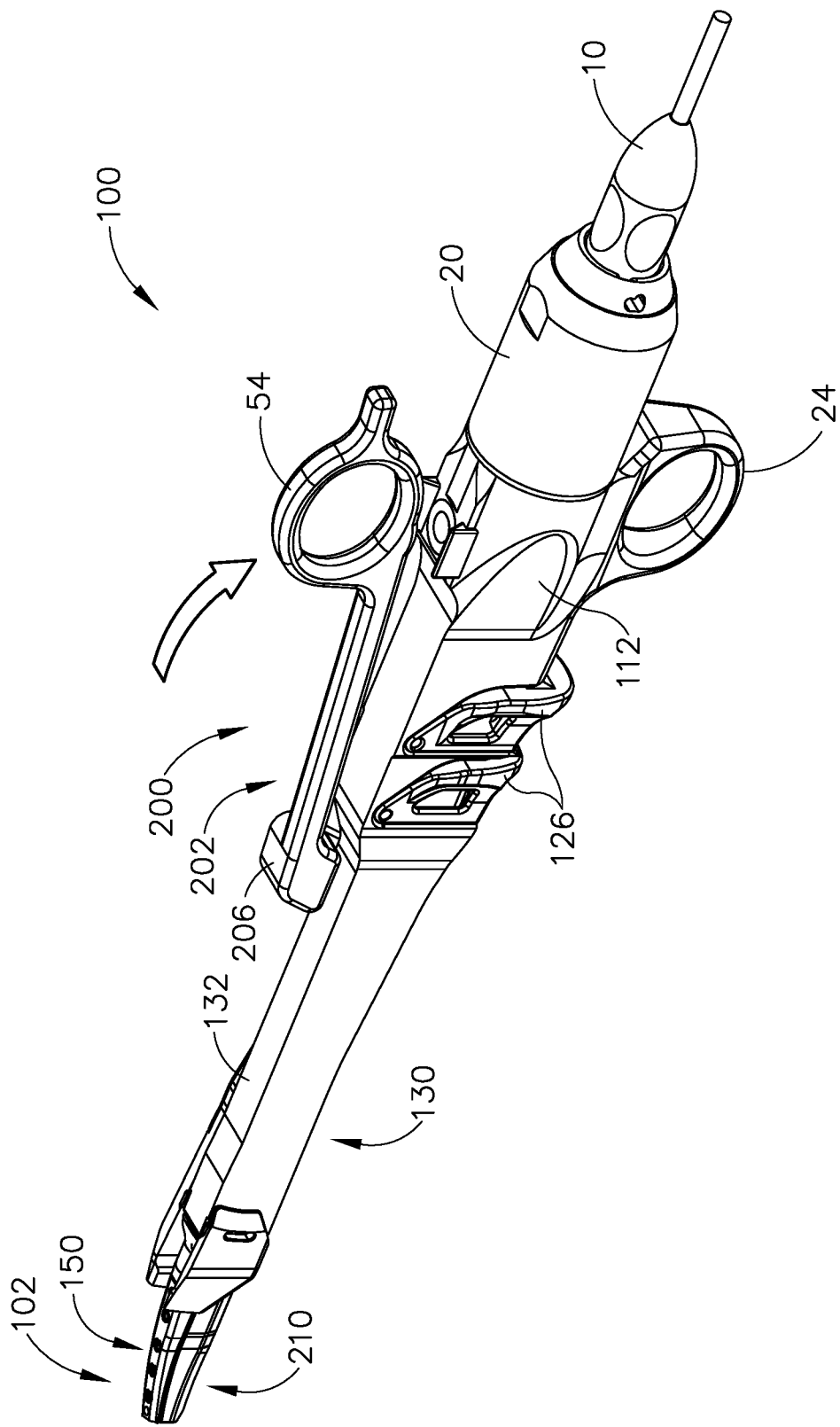
FIG. 32 depicts another perspective view of the instrument of FIG. 1A.

FIGS. 32-35 show an exemplary use of instrument (10) during a surgical procedure. It should be understood that prior to such a procedure, an operator may couple clamp arm assembly (200) to handle assembly (110) using the procedures and methods described above. As can be seen in FIG. 32, an operator may clamp end effector (102) by pivoting clamp arm assembly (200) from the position shown in FIG. 1B to the position shown in FIG. 32, with tissue captured between clamp pad assembly (210) and blade (152). End effector (102) may then cut and/or seal tissue using a combination of ultrasonic and RF energy, respectively.

As described above, button (280) is disposed near the proximal end of handle assembly (110). In particular, button (280) is disposed in a position that is adjacent to grip (54). Button (280) is configured to be activated after a predetermined amount of clamping force has been applied by an operator to clamp arm assembly (200). For instance, as shown in FIG. 32, when a suitable amount of clamping force is applied, clamp arm assembly (200) will deflect slightly. Such a deflection results in the underside of grip (54) contacting button (280) to actuate button (280).

When button (280) is actuated, a signal is sent to generator (5) that a suitable amount of clamping force has been applied. In the present example, the signal from button (280) to generator (5) causes generator (5) to either initiate a sealing algorithm (if one of buttons (126) is already being actuated) or enable initiation of a sealing algorithm (which would thereafter be initiated in response to actuation of a button (126)). As described above, actuation of button (280) lets the user know that clamp arm assembly (200) is fully compressed and the appropriate force is on the tissue to achieve a proper seal during execution of a sealing algorithm. In some procedures a desired quality for a seal is best achieved with there is sufficient heat and pressure applied to the tissue and/or vessel. In such examples where sufficient heat and pressure on the tissue is desired, without such sufficient pressure, the seal could be compromised. In an example where button (280) is not depressed or activated, where one of buttons (126) is actuated to seal the tissue, a user may understand that the appropriate force on the tissue for proper sealing was not obtained when the RF energy for sealing was applied to the tissue. Similarly, actuation of button (280) can be monitored through the sealing action to understand if the appropriate amount of force was maintained on the tissue throughout the application of the RF energy for sealing the tissue. The following examples represent several possible scenarios of how generator (5) may react to a combination of button (280) being actuated and one of buttons (126) being actuated. It should be understood that the following examples are merely illustrative.

In a first exemplary scenario, button (126) and button (280) are both actuated. In the present example, the actuation of button (126) and button (280) initiates a seal only mode where RF energy is provided and no or lower harmonic energy is provided. This condition indicates to generator (5) the presence of all conditions necessary to suitably seal tissue. Accordingly, generator (5) will initiate a sealing algorithm to apply RF energy, with or without ultrasonic energy, to any tissue captured between clamp pad assembly (210) and blade (152). In some other examples, only ultrasonic energy may be used for sealing, while in other examples only RF energy may be used for sealing. In the present example, once the sealing algorithm is complete an end tone or seal complete tone, or other auditory or visual indicator may be provided by generator (5). The completion of the sealing algorithm may be dictated when a threshold of impedance is reached. Although the end tone may be provided in the present example, the occurrence of the end tone does not end the application of RF energy. On the contrary, in the present example RF energy continues after the end tone so long as button (126) and button (280) continue to be actuated. In the present example, a timer may also be provided where if the RF sealing takes longer than a predetermined amount of time then an error tone sounds to tell the operator to release and re-grasp the tissue and/or vessel.

In a second exemplary scenario, button (280) is not activated, but button (126) is activated. In the present example, this action initiates a spot coagulation mode where RF energy is provided at a normal or higher voltage and no or lower harmonic energy is provided. In this scenario, generator (5) initiates a coagulation algorithm to apply RF energy, with or without ultrasonic energy, to tissue that is captured between clamp pad assembly (210) and blade (152). However, no end tone or other indication will be provided to the operator. Similarly, no error tone will be provided to the operator. Instead, the coagulation algorithm will continue to run for as long as button (126) is activated so the operator can perform spot coagulation with no timeout or interruptions in RF energy application. In this manner, the clamp assembly (200) can be slightly open or spread apart to aid in spot or side coagulation.

In a third exemplary scenario, if button (280) is not activated while button (126) is activated, generator (5) activates a touch up algorithm. When the touch up algorithm is activated, a higher voltage is applied to the RF circuit to ablate any excess tissue that may be captured between clamp pad assembly (210) and blade (152).

In a fourth exemplary scenario, if button (280) is not activated while button (126) is activated, generator (5) applies no voltage to the RF circuit. Instead, generator (5) simply supplies an operator with an error tone, or other auditory or visual indicator to indicate an error.

In a fifth exemplary scenario, button (126) and button (280) are both actuated and generator (5) initiates a sealing algorithm where RF energy is provided and an increase in harmonic energy is provided for sealing. Accordingly, in this example, while depressing button (126) alone may provide RF energy and/or no or low harmonic energy, when depressing or actuating both button (126) and button (280), the increased harmonic energy is provided for sealing. In the present example, once the sealing algorithm is complete an end tone or seal complete tone, or other auditory or visual indicator may be provided by generator (5). The completion of the sealing algorithm may be dictated when a threshold of impedance is reached. Although the end tone may be provided in the present example, RF energy and increased harmonic energy continues after the end tone so long as button (126) and button (280) continue to be actuated. In the present example, a timer may also be provided where if the sealing takes longer than a predetermined amount of time then an error tone sounds to tell the operator to release and re-grasp the tissue and/or vessel. In other examples where actuating both buttons (126, 280) causes an increase in the harmonic energy, after the end tone occurs, one or more of the RF energy and harmonic energy may cease until a release and re-grasping step is performed by the operator.

In some examples, button (280) is omitted. In examples where button (280) is omitted, it may still be desirable to sense the force applied to tissue through end effector (102) because seal quality may be generally related to the force applied to tissue via end effector (102). In addition to or as an alternative to button (280), tissue impendence may be measured by generator (5) to determine whether adequate force is being applied to tissue. In particular, in some examples generator (5) is configured to measure the impedance of tissue captured between electrode (218) and blade (152) by applying a test voltage through electrode (218) and blade (152). When generator (5) measures harmonic impedance within a certain predetermined range, generator (5) will determine that a suitable amount of force is being applied to tissue captured between clamp pad assembly (210) and blade (152) and thereby positively activate a force indicator.

As similarly described above with respect to button (280), generator (5) may be responsive to measurements of harmonic impedance by similarly activating various algorithms. For instance, in configurations where button (280) is omitted, positive activation of the force indicator can be equated to activation of button (280) as described in the above scenarios where button (280) is present, and generator (5) configured to respond in the same manner described above. For instance, in a first exemplary scenario when button (126) is activated along with a force indicator being activated (e.g., where harmonic impendence indicates that blade (152) is under a clamping load, thereby indicating a clamping force by clamp pad assembly (210)), generator (5) responds by activating the sealing algorithm as described above.

In a second exemplary scenario, if button (126) is activated without corresponding activation of a force indicator (e.g., where harmonic impendence does not indicate that blade (152) is under a clamping load, thereby indicating either no clamping force or an insufficient clamping force by clamp pad assembly (210)), then generator (5) may still initiate the coagulation algorithm as described above.

In a third exemplary scenario, if button (126) is activated without activation of the force indicator, generator (5) activates a touch up algorithm. When the touch up algorithm is activated, a higher voltage is applied to the RF circuit to ablate any excess tissue that may be captured between clamp pad assembly (210) and blade (152).

In a fourth exemplary scenario, if button (126) is activated without activation of force indicator, generator (5) applies no voltage to the RF circuit. Instead, generator (5) simply supplies an operator with an error tone or other auditory or visual indicator to indicate an error.

In a fifth exemplary scenario, button (126) and the force indicator are both activated and generator (5) initiates a sealing algorithm where RF energy is provided and an increase in harmonic energy is provided for sealing. Accordingly, in this example, while depressing button (126) alone may provide RF energy and/or no or low harmonic energy, when depressing or actuating button (126) when the force indicator is also activated, the increased harmonic energy is provided for sealing. In the present example, once the sealing algorithm is complete an end tone or seal complete tone, or other auditory or visual indicator may be provided by generator (5). The completion of the sealing algorithm may be dictated when a threshold of impedance is reached. Although the end tone may be provided in the present example, RF energy and increased harmonic energy continues after the end tone so long as button (126) and the force indicator continue to be activated. In the present example, a timer may also be provided where if the sealing takes longer than a predetermined amount of time then an error tone sounds to tell the operator to release and re-grasp the tissue and/or vessel. In other examples where an increase in the harmonic energy occurs in response to activation of both button (126) and the force indicator, after the end tone occurs, one or more of the RF energy and harmonic energy may cease until a release and re-grasping step is performed by the operator.

Figure 35:
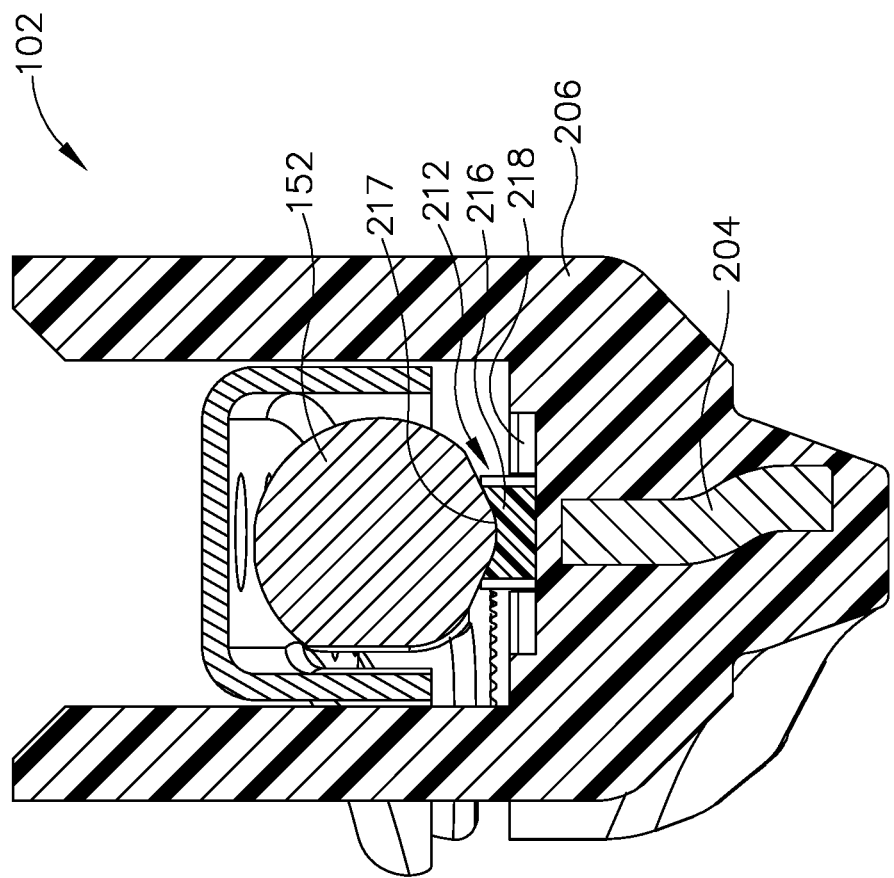
FIG. 35 depicts a cross-sectional view of the end effector of FIG. 1A, taken along line 35-35 of FIG. 33.

FIGS. 33-35 show use of various features of clamp pad assembly (210) when instrument (100) is in use. As can be seen in FIGS. 33 and 34, when end effector (102) is closed, clamp pad assembly (210) is positioned to compress tissue against blade (150) to thereby sever the tissue when blade (150) is activated with ultrasonic energy. Clamp pad (212) stops short of the distal end of end effector (102). Moreover, the underside of the distal end of blade (152) is recessed. This combination of clamp pad (212) stopping short and the distal end of blade (152) being recessed forms a non-cutting region (286) at the distal end of end effector (102). Thus, while tissue may be compressed at a relatively high pressure between blade (150) and clamp pad (212), tissue will be compressed at a relatively lower pressure in the non-cutting region (286). In the present example, end effector (102) is configured such that the gap of non-cutting region (286) is sized to prevent blade (150) from achieving sufficient tissue compression with clamp arm assembly (210) to cut the tissue ultrasonically. In other words, tissue that is captured in non-cutting region (286) will not be cut by blade (150) even when blade (150) is activated ultrasonically in the present example.

While blade (150) does not meaningfully apply ultrasonic energy to tissue that is captured within non-cutting region (286) (i.e., not meaningful enough to cut the tissue), this distal region of blade (150) associated with non-cutting region (286) may still serve a purpose of providing a return path for RF energy communicated through end effector (102). As described above, electrode (218) generally surrounds the perimeter of clamp pad (212), including wrapping around the distal end of clamp pad (212). Because electrode (218) surrounds the perimeter of clamp pad (212), it should be understood that at least a portion of electrode (218) extends distally of clamp pad (212) within end effector (102) into non-cutting region (286). Accordingly, when tissue is captured between clamp pad assembly (210) and blade (150), the region of tissue that is disposed within non-cutting region (286) is only sealed through RF energy, but is not cut by ultrasonic energy. As a consequence, this generally results in any cut tissue having a sealed portion ahead of any cut line. In some examples, such a feature may be desirable to prevent any inadvertent openings in the tissue from being created by a tissue cutting operation.

FIG. 35 shows operation of locating portion (216) of clamp pad (212) during a cutting and/or sealing sequence by end effector (102). As described above, locating portion (216) extends upwardly above gripping portion (213) with an indented upper surface (217). As can be seen in FIG. 35, when end effector (102) is in the closed configuration, indented upper surface (217) of locating portion (216) receives blade (152). When blade (152) is received within upper surface (217) of locating portion (216), upper surface (217) and blade (152) interact cooperatively to locate relative to each other, such that upper surface (217) and blade (152) cooperate to guide blade (152) and clamp arm assembly (212) into alignment with each other as blade end effector (102) reaches the closed configuration. Thus, upper surface (217) ensures that blade (152) and clamp pad (212) are generally aligned relative to each other.

H. Exemplary Translating Pivot

Figure 36A:
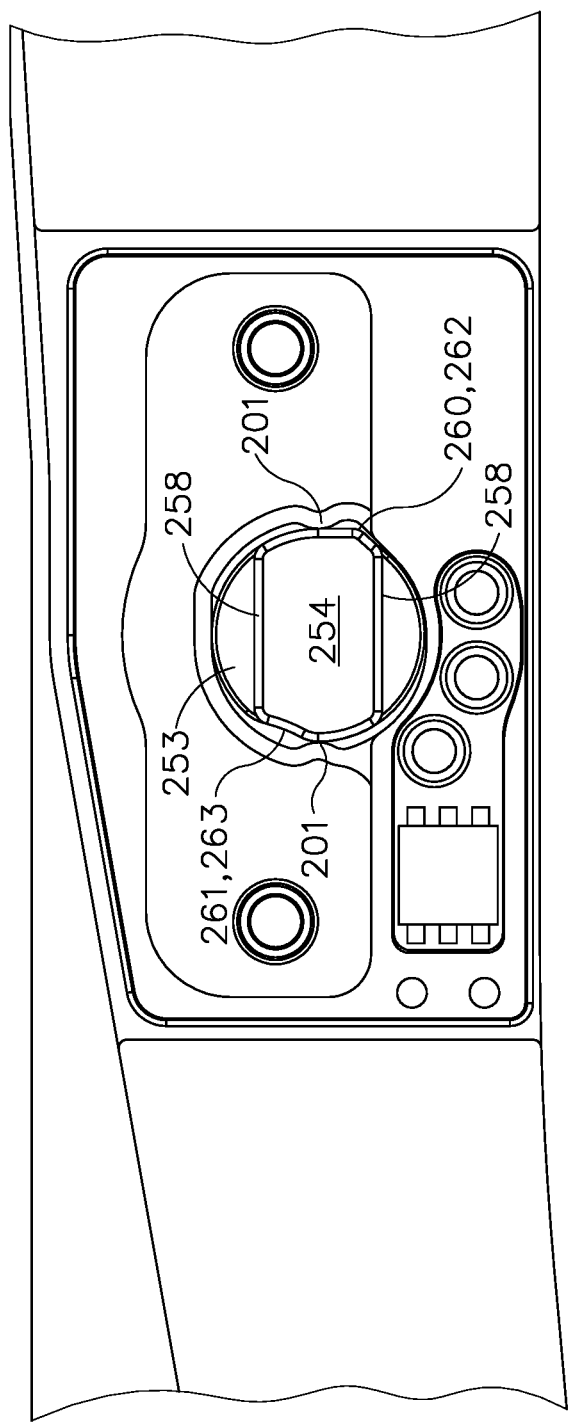
FIG. 36A depicts a side elevational view of some of the coupling features of FIG. 11, with the clamp arm in a first pivotal position in relation to the handle assembly.
Figure 36B:
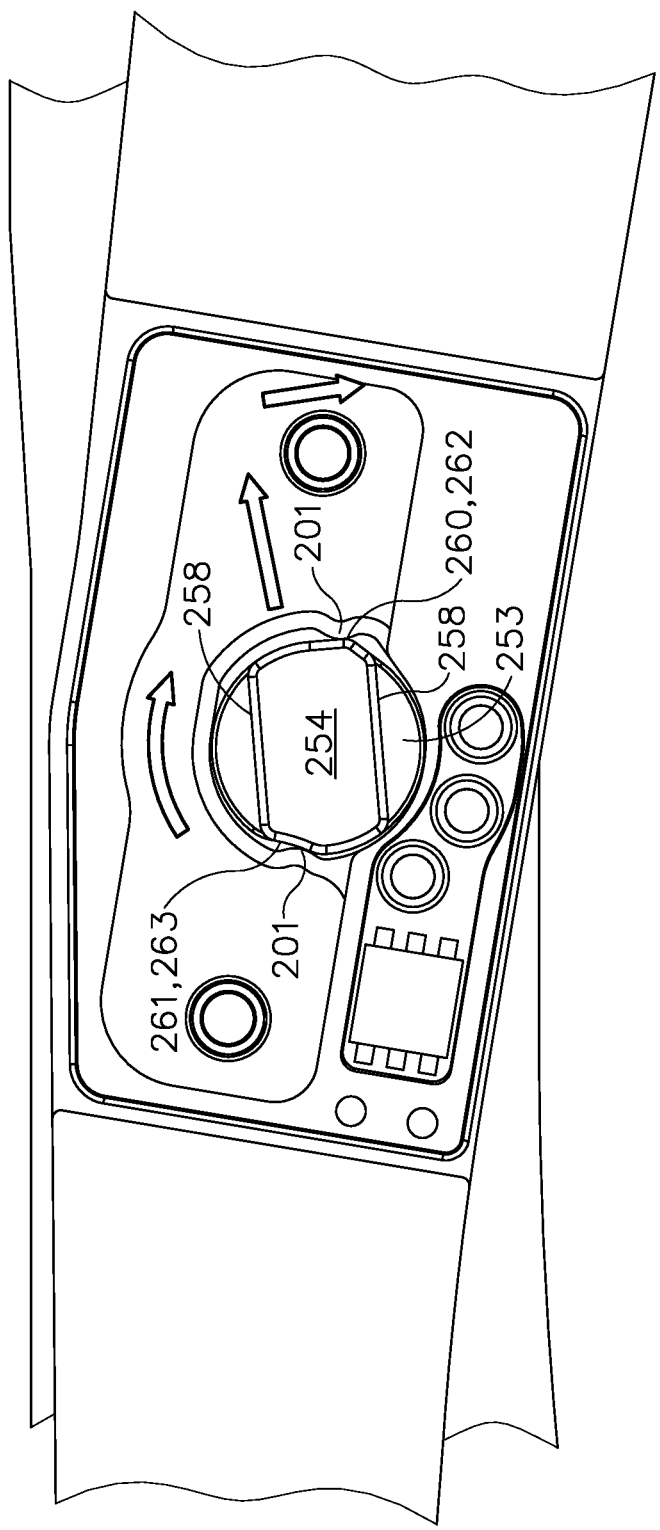
FIG. 36B depicts a side elevational view of some of the coupling features of FIG. 11, with the clamp arm in a second pivotal position in relation to the handle assembly.
Figure 37:
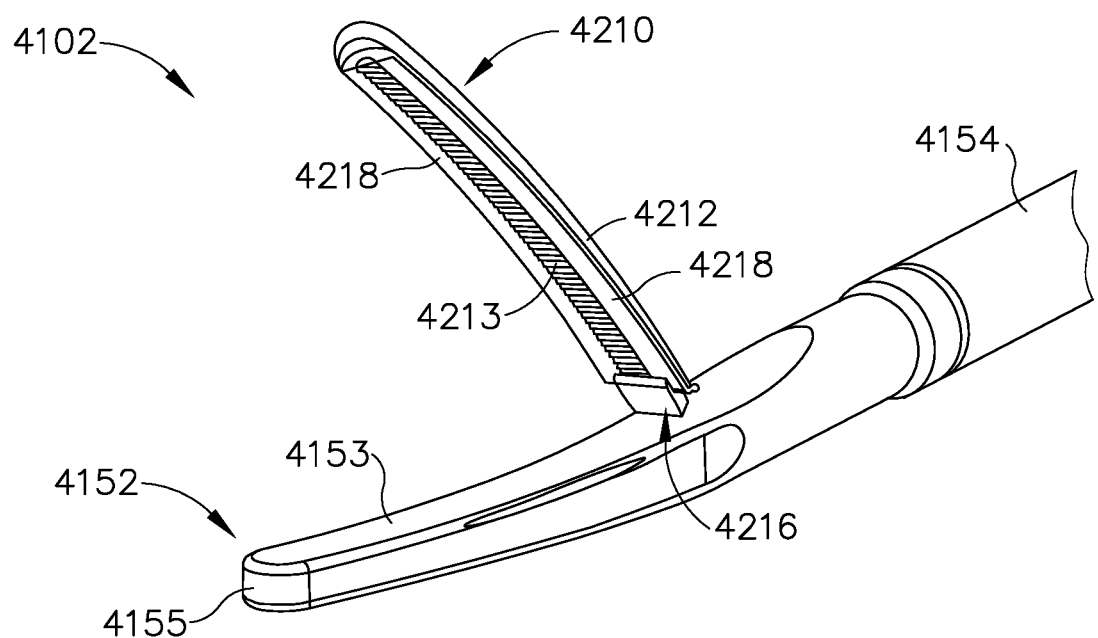
FIG. 37 depicts a perspective view of another exemplary end effector for use with the surgical instruments described herein, with the end effector in an open configuration.

As mentioned above, translation features (260, 261, 262, 263) are configured to translate clamp arm assembly (200) as clamp arm assembly (200) is pivoted relative to handle assembly (110) through interaction with corresponding protrusions (201) (shown in FIG. 16) in body (206) of clamp arm assembly (200). As shown in FIGS. 36A-36B, protrusions (201) of clamp arm assembly (200) are dimensioned to make contact with the exterior of attachment portion (254) and base (253). Specifically, protrusions (201) are dimensioned to contact translation features (260, 261, 262, 263) as clamp arm assembly (200) pivots relative to handle assembly (110). The geometry of translation features (260, 261, 262, 263) forces protrusions (201), and therefore clamp arm assembly (200), distally and downwardly relative to handle assembly (110) when end effector (102) transitions to the open position. Conversely, the geometry of translation features (260, 261, 262, 263) forces protrusions (201), and therefore clamp arm assembly (200), proximally and upwardly relative to handle assembly (110) when end effector (102) transitions to the closed position.

In other words, translation features (260, 261, 262, 263) act as a camming feature as protrusions (201) pivot around attachment portion (254) and base (253). This may allow clamp arm to pull tissue grasped by end effector (102) back toward handle assembly (110) when closing to prevent a milking effect. This may also reduce the occurrence of "tags" of tissue (e.g., flattened but uncut regions of tissue). This may also allow clamp arm assembly (200) to swivel and lock into place with tighter tolerances than if clamp arm assembly (200) just pivoted without translation. Tighter tolerances may occur due to clamp arm assembly (200) tightening to attachment portion (254) and base (253) as clamp arm assembly (200) rotates to a closed position. This tightening may reduce front to back misalignment.

II. Exemplary Alternative End Effectors

A. Overview

FIGS. 37-56 illustrate other exemplary end effectors that may be used with any of instruments described herein, including instrument (100). In this regard, the clamp pad assemblies of the end effectors described below may be readily substituted for any of the clamp arm assemblies described above, including clamp arm assemblies (200, 400). Similarly, the blade assemblies of the end effectors described below may be substituted for any of the blades or blade assemblies described above, including blade (152) and blade assembly (550). Each of the exemplary end effectors described below comprise an ultrasonic blade that is formed unitarily with a waveguide.

While not shown in FIGS. 37-56, it should be understood that each of the end effectors described below can also include a heat shield similar to heat shield (170) described above. Of course a heat shield is not required in all versions and thus may be omitted from the end effectors described below if desired. Each of the clamp pad assemblies of the exemplary end effectors described below further comprise a clamp pad and an electrode. In use, the exemplary end effectors shown in FIGS. 37-56, and described further below, are all able to provide ultrasonic cutting, ultrasonic sealing, and RF electrosurgical sealing as described above. The exemplary end effectors described below present alternative features, at least some of which include alternative blade shapes, electrode offsets, and clamp pad designs. These and other details will be described in greater detail in the following sections and paragraphs.

B. Flat Blade with Proximal Pad Bumper

FIGS. 37-40 illustrate an end effector (4102) comprising an ultrasonic blade (4152) connected with a waveguide (4154); and a clamp pad assembly (4210) including a clamp pad (4212) and electrode (4218). Waveguide (4154) is connectable with the various shaft assemblies of the instruments described above in the same or similar manner as waveguide (154). Blade (4152) is configured with a flat surface (4153) for cutting and sealing. Blade (4152) is also configured with an arcuate shape and a blunt distal end (4155) as shown. As discussed above, the side of blade (4152) opposite to flat surface (4153) may be protected by a heat shield as shown and described above with respect to other versions.

Clamp pad assembly (4210) is connectable with one of the various clamp arm assemblies of the instruments described above. For example, clamp pad assembly (4210) is connectable with clamp arm assembly (200) in the same or similar manner that clamp pad assembly (210) connects with clamp arm assembly (200). In view of the teachings herein, other ways in which clamp pad assembly (4210)

connects with the various clamp arm assemblies described herein, including but not limited to clamp arm assemblies (200, 400, 1200, 2200, 3200), will be apparent to those of ordinary skill in the art.

Figure 39:
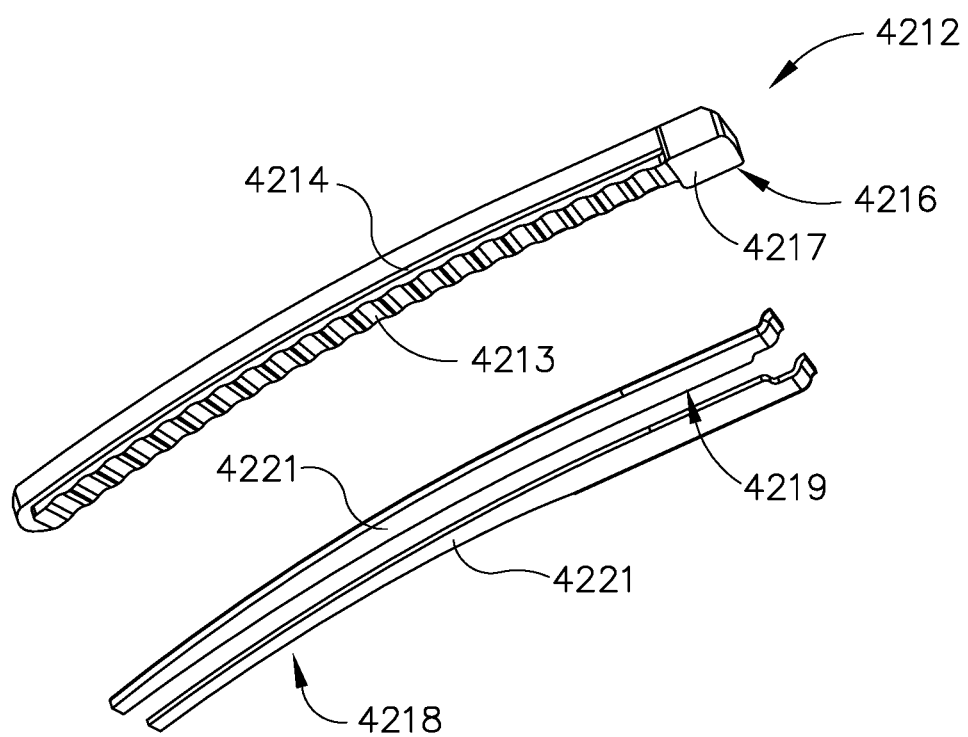
FIG. 39 depicts an exploded view of a clamp pad assembly of the end effector of FIG. 37.

FIG. 39 shows clamp pad assembly (4210) in greater detail. As can be seen, clamp pad assembly (4210) comprises a clamp pad (4212) and an electrode (4218). Clamp pad (4212) comprises a single generally homogenous insulating material such as polytetrafluoroethylene (PTFE), rubber, and/or other similar insulating materials. The particular shape of clamp pad (4212) generally corresponds to the shape of blade (4152). In particular, clamp pad (4212) generally defines a shape similar to an outline of blade (4152). Clamp pad (4212) comprises a gripping portion (4213) configured to grip tissue and hold such tissue in position as the tissue is being clamped between clamp pad assembly (4210) and ultrasonic blade (4152). In the present example, gripping portion (4213) includes a repeating pattern of ribs or teeth to enhance the grippability of gripping portion (4213). In other examples, gripping portion (4213) is equipped with numerous other features to enhance grippability such as knurling, irregular surface patterns, or any other generally rough surface. In still other examples, gripping portion (4213) is equipped with a merely flat surface without any particular feature to enhance grippability. Gripping portion (4213) terminates inwardly of the outer lateral edges of clamp pad (4212). This defines a shoulder (4214) in clamp pad (4212) that is generally configured to maintain clamp pad (4212) within the clamp arm assembly via electrode (4218) as described further below.

Clamp pad (4212) also comprises pad bumper (4216) defined in clamp pad (4212) at the proximal end of clamp pad (4212). Pad bumper (4216) is generally configured to maintain relative positioning between clamp pad (4212) and blade (4152) during clamping, and thereby act as a non-conductive gap setting feature to maintain spacing between blade (4152) and electrode (4218). Pad bumper (4216) comprises a first surface (4217) configured to contact surface (4153) of blade (4152). In the illustrated version, first surface (4217) of pad bumper (4216) is flat, which corresponds with the flat profile of surface (4153) of blade (4152). Accordingly, it should be understood that the profile of first surface (4217) generally corresponds to the profile of blade (4152) at the location of contact such that first surface (4217) is configured to receive blade (4152).

Figure 38:
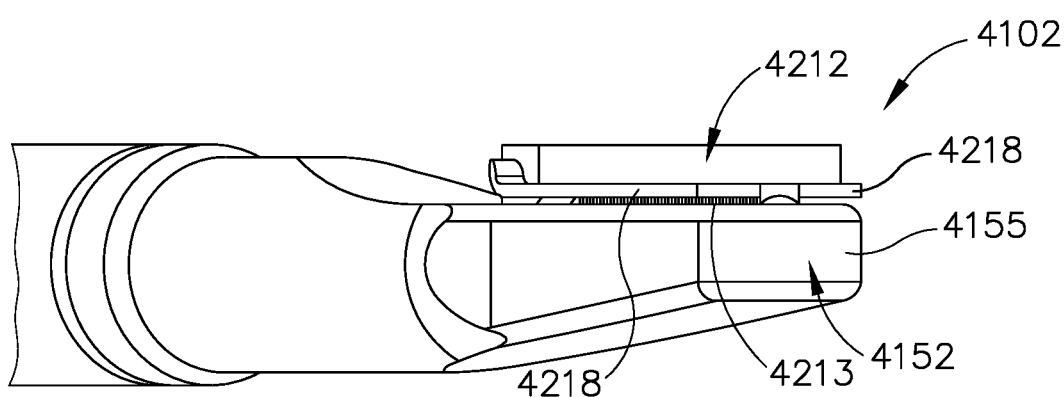
FIG. 38 depicts another perspective view of the end effector of FIG. 37, with the end effector in a closed configuration.
Figure 40:
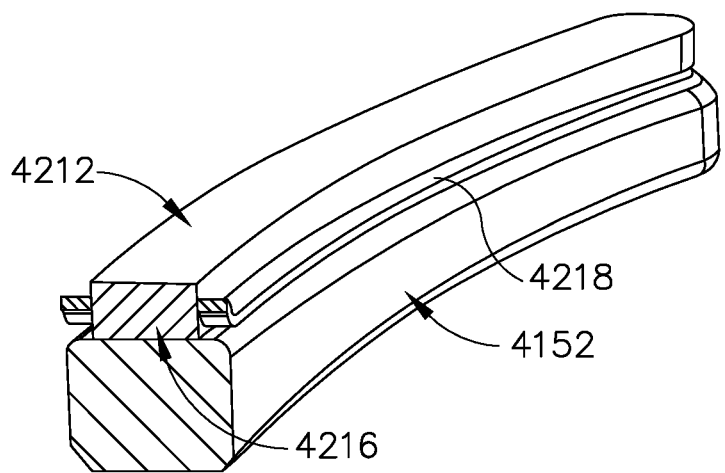
FIG. 40 depicts a cross-sectional view of the end effector of FIG. 37.
Figure 41:
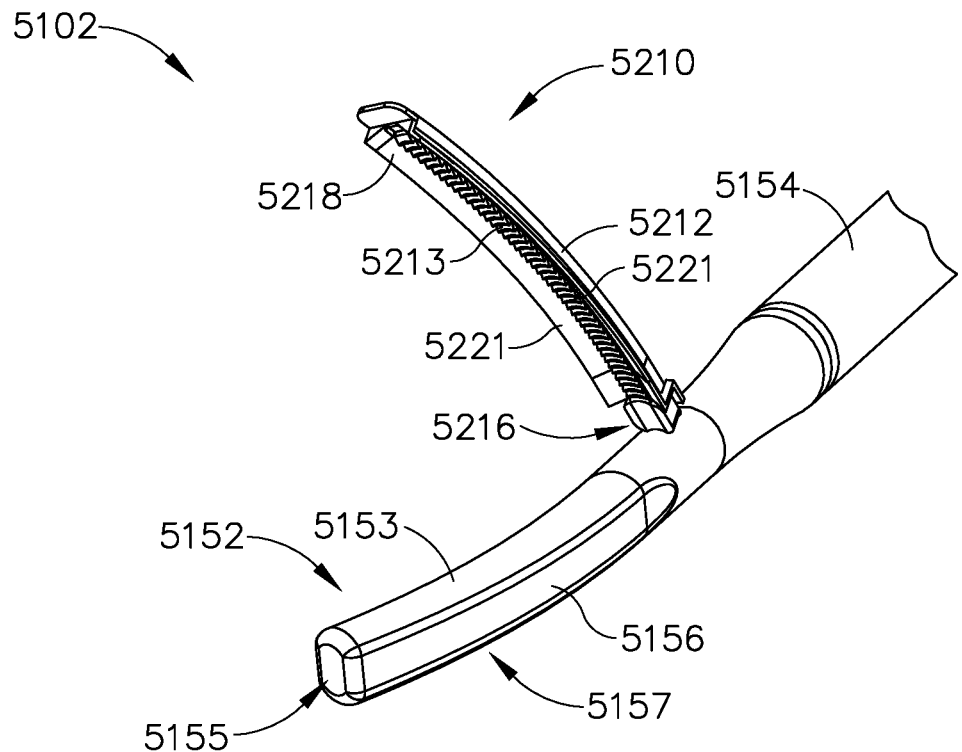
FIG. 41 depicts a perspective view of another exemplary end effector for use with the surgical instruments described herein, with the end effector in an open configuration.

When end effector (4102) is in an assembled state, pad bumper (4216) extends further towards flat surface (4153) of blade (4152) compared to electrode (4218). In this configuration, when end effector (4102) is in a closed position as shown in FIGS. 38 and 40, pad bumper (4216) acts as a spacer or provides a spacing to prevent electrode (4218) from contacting blade (4152) and thereby causing a short circuit when RF electrosurgical energy is used to provide RF electrosurgical sealing. Pad bumper (4216) comprises a width that matches the width of clamp pad (4212). Accordingly, in the present version, pad bumper (4216) does not include a shoulder portion similar to shoulder (4214) that extends along the remainder of clamp pad (4212).

Electrode (4218) comprises a single relatively thin strip of relatively rigid electrically conducting material. In some examples electrode (4218) comprises an electrically conductive metal such as copper, gold, steel, aluminum, silver, etc. In still other examples, electrode (4218) comprises an electrically conductive non-metallic material such as conducting polymers, silicides, graphite, etc. The thickness of electrode (4218) is generally thinner than gripping portion (4213) of clamp pad (4212), such that gripping portion (4213) protrudes proudly past the surface of electrode (4218) facing blade (4152). However, electrode (4218) is still generally thick enough to maintain a suitable amount of structural rigidity. The particular shape of electrode (4218) generally corresponds to the shape of clamp pad (4212). In particular, electrode (4218) generally defines a shape similar to an outline of clamp pad (4212). Electrode (4218) further defines an opening (4219) therein. Opening (4219) is configured to receive gripping portion (4213) of clamp pad (4212) therethrough such that electrode (4218) is configured to engage with shoulder (4214) of clamp pad (4212). In the illustrated version of FIGS. 37-40, when end effector (4102) is in the closed or clamping position, a tissue-contacting surface (4221) of electrode (4218) is oriented generally parallel to flat surface (4153) of blade (4152).

When clamp pad assembly (4210) is assembled, clamp pad (4212) is first inserted into a clamp pad receiving channel of a clamp arm assembly, e.g. receiving channel (208) of clamp arm assembly (200). As described above, clamp pad receiving channel (208) is defined in the distal end of a body (202). Electrode (4218) is then inserted over clamp pad (4212), with electrode (4218) seating on shoulder (4214) of clamp pad (4212), and with gripping portion (4213) of clamp pad (4212) protruding through opening (4219). Electrode (4218) is then resistance welded or otherwise secured to body (202). In the present example, electrode (4218) is resistance welded in place to structural core (204) of body (202) at the proximal and distal ends of electrode (4218).

In other examples, electrode (4218) is resistance welded at any other suitable location in addition to, or in lieu of, welding at the distal and proximal ends of electrode (4218). In still other examples, resistance welds are omitted entirely and electrode (4218) is secured to body (202) by any other suitable means such as other welding processes and/or adhesive bonding, etc. It should be understood that once electrode (4218) is secured to body (202), electrode (4218) also couples clamp pad (4212) to body (202) by engagement between electrode (4218) and shoulder (4214) of clamp pad (4212). Accordingly, the thickness of electrode (4218) is generally thick enough to provide enough rigidity to couple clamp pad (4212) to body (202). In other versions, clamp pad assembly (4210) may be assembled with other clamp arm assemblies (400, 1200, 2200, 3200), as will be understood by those of ordinary skill in the art in view of the teachings herein.

Electrode (4218) is configured to cooperate with blade (4152) to provide bipolar RF electrosurgical energy to tissue that is captured between clamp pad assembly (4210) and blade (4152). In particular, electrode (4218) is activated with RF energy and blade (4152) provides a return path for the RF energy. It should therefore be understood that blade (4152) is capable of serving two distinct roles in the present example—one role of applying ultrasonic energy to tissue that is in contact with blade (4152) and another role of cooperating with electrode (4218) to provide bipolar RF energy to tissue that is captured between clamp pad assembly (4210) and blade (4152).

In some versions, the ultrasonic energy and RF energy are applied simultaneously. In some other versions, the ultrasonic energy and RF energy are applied in an automatically alternating fashion. In some other versions, the ultrasonic energy and RF energy are applied in a simple series (e.g., ultrasonic energy first, followed by RF energy). In some other versions, the ultrasonic energy and RF energy are selectively applied independently. Other suitable features that may be used to provide communication of RF energy through electrode (4218) and blade (4152) will be apparent to those of ordinary skill in the art in view of the teachings herein.

In the present example, because electrode (4218) is generally thinner than gripping portion (4213) of clamp pad (4212), gripping portion (4213) generally protrudes proudly from surface (4221) of electrode (4218) that faces blade (4152) so as to prevent blade (4152) from directly contacting electrode (4218) when end effector (4102) is in a closed or clamping configuration. Thus, it should be understood that electrode (4218) is generally not configured to physically contact blade (4152). However, as described above, electrical continuity for RF energy is generally achieved by passing electrical current through a patient's tissue as it is cut and/or sealed, and in some versions this electrical current flows between electrode (4218) and blade (4152). In this regard, end effector (4102) comprises multiple features that provide spacing to prevent contact between conductive blade (4152) and electrode (4218) to prevent short circuiting when using RF electrosurgical energy. As discussed above, one such feature is gripping portion (4213), and another such feature is pad bumper (4216).

The location of pad bumper (4216) is proximally positioned along clamp pad (4212) as discussed above. Furthermore and as also described above, the pivoting action of the clamp arm assembly is provided at a pivoting location that is proximal to clamp pad assembly (4210). Accordingly, when moving end effector (4102) to a closed position for clamping, pad bumper (4216) will contact surface (4153) of blade (4152) before gripping portion (4213) to prevent contact between blade (4152) and electrode (4218). Pad bumper (4216) thus prevents a short circuit when using RF electrosurgical energy.

Additionally, the size of pad bumper (4216), being wider and generally greater in surface area per unit of length along clamp pad (4212) compared to gripping portion (4213), allows for a substantially larger area of clamp pad (4212) to contact blade (4152). This greater area combined with the proximal location of pad bumper (4216) can contribute to less blade (4152) displacement and less heat build-up where pad bumper (4216) contacts blade (4152). This in turn reduces flow of pad material and warping of clamp pad (4212), so as to reduce the wear and lengthen the life or use cycle of clamp pad (4212).

As shown in the illustrated version, electrode (4218) extends proximally alongside pad bumper (4216). However, the width of electrode (4218) in this area alongside pad bumper (4216) is less compared to the width of electrode (4218) in the areas alongside gripping portion (4213) where shoulder (4214) is present. To maintain cut and seal quality and integrity, pad bumper (4216) and the accompanying reduced width electrode (4218) alongside pad bumper (4216) are positioned proximally of tissue stops (290, 1290, 1296, 2290, 2296). In this configuration, tissue is prevented from entering the proximal region where pad bumper (4216) is located. Therefore, tissue cutting and sealing is not required to occur along pad bumper (4216) region and instead is reserved for the area between gripping portion (4213) of clamp pad (4212) and blade (4152). In view of the teachings herein, various ways to position pad bumper (4216) relative to tissue stops (290, 1290, 1296, 2290, 2296) to achieve acceptable cutting and sealing performance while providing spacing features to prevent short circuits between electrode (4218) and blade (4152) will be apparent to those of ordinary skill in the art.

Referring to FIGS. 38 and 40, in the illustrated version, electrode (4218) has no offset with blade (4152). Generally, electrode offset represents the amount of overlap of the electrode beyond the lateral edge of the blade from a profile view of the end effector. Thus in the present example where there is no offset for electrode (4218), the width of electrode (4218) follows the width of blade (4152) along its length such that there is no overhang (positive offset) or setback (negative offset) of electrode (4218) relative to the side edges of blade (4152). As will be described further below, in other versions, some of which may include end effectors having flat blades, electrode (4218) can be configured such that there is an offset relative to blade (4152), e.g. a positive offset where electrode (4218) overhangs blade (4152) on each side along the length of blade (4152).

In some versions of a flat blade having an electrode with a positive offset where the electrode width extends past the edges or side surfaces of the flat blade on each side, improved hemostasis may be observed over a similar end effector without an offset electrode. In studying performance, burst pressure data may be collected from previously sealed tissue using both the end effector having a flat blade with no offset, and the end effector having a flat blade with the offset. By way of example only, three tissue types may be studied: bundles, large carotids, and Thyrocervical vessels. For all three tissue types, the average burst pressure may increase when using the end effector with the flat blade and offset electrode. The burst pressure recorded may be the pressure at which the previously sealed tissue leaked. Thus a higher burst pressure would be indicative of a stronger seal. By way of example only, for tissue bundles, the flat blade with offset may show an improvement of about 9% in burst pressure over the flat blade with no offset in some examples. For the large carotids, an improvement of about 11% in burst pressure may be observed in some examples. For the Thyrocervical vessels, an improvement of about 250/% in burst pressure may be observed in some examples.

C. Rounded Blade with Proximal Pad Bumper

FIGS. 41-44 illustrate an end effector (5102) comprising an ultrasonic blade (5152) connected with a waveguide (5154), and a clamp pad assembly (5210) including a clamp pad (5212) and electrode (5218). Waveguide (5154) is connectable with the various shaft assemblies of the instruments described above in the same or similar manner as waveguide (154). Blade (5152) is configured with a rounded upper surface (5153) for cutting and sealing, with flat side surfaces (5156) on each side and a rounded lower surface (5157). Blade (5152) is also configured with an arcuate shape and a blunt distal end (5155) as shown. As discussed above, lower surface (5157) of blade (5152) may be protected by a heat shield as shown and described above with respect to other versions.

Clamp pad assembly (5210) is connectable with one of the various clamp arm assemblies of the instruments described above. For example, clamp pad assembly (5210) is connectable with clamp arm assembly (200) in the same or similar manner that clamp pad assembly (210) connects with clamp arm assembly (200). In view of the teachings herein, other ways in which clamp pad assembly (5210) may connect with the various clamp arm assemblies described herein, including but not limited to clamp arm assemblies (200, 400, 1200, 2200, 3200), will be apparent to those of ordinary skill in the art.

Figure 43:
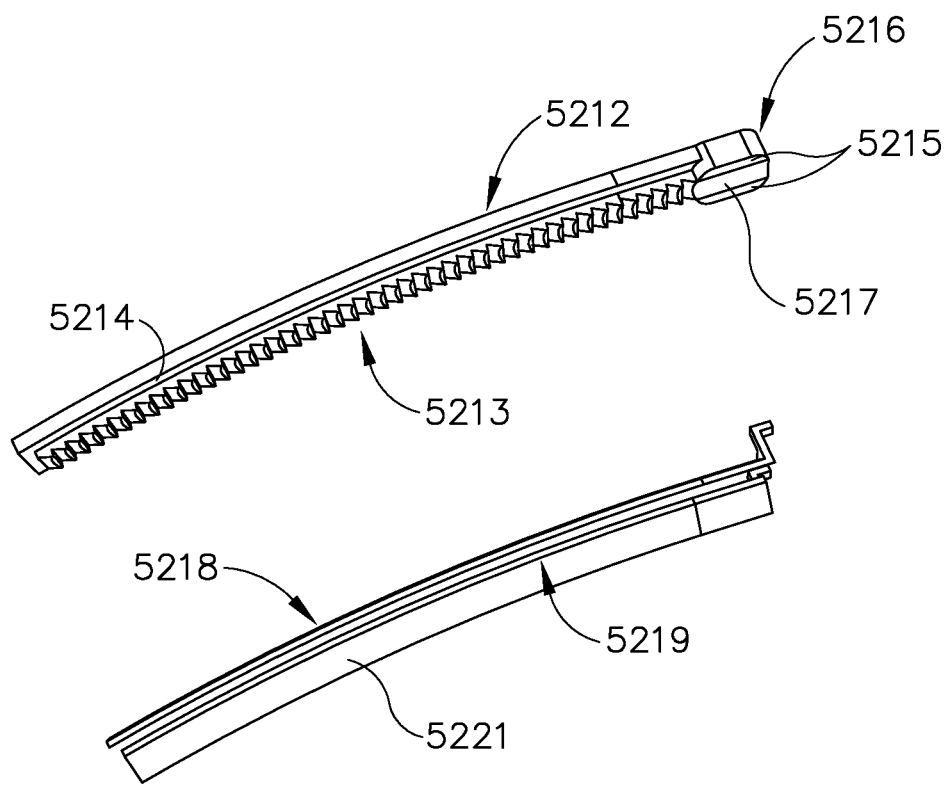
FIG. 43 depicts an exploded view of a clamp pad assembly of the end effector of FIG. 41.

FIG. 43 shows clamp pad assembly (5210) in greater detail. As can be seen, clamp pad assembly (5210) comprises a clamp pad (5212) and an electrode (5218). Clamp pad (5212) comprises a single generally homogenous insulating material such as polytetrafluoroethylene (PTFE), rubber, and/or other similar insulating materials. The particular shape of clamp pad (5212) generally corresponds to the shape of blade (5152). In particular, clamp pad (5212) generally defines a shape similar to an outline of blade (5152). Clamp pad (5212) comprises a gripping portion (5213) configured to grip tissue and hold such tissue in position as the tissue is being clamped between clamp pad assembly (5210) and ultrasonic blade (5152).

In the present example, gripping portion (5213) includes a repeating pattern of ribs or teeth to enhance the grippability of gripping portion (5213). In other examples, gripping portion (5213) is equipped with numerous other features to enhance grippability such as knurling, irregular surface patterns, or any other generally rough surface. In still other examples, gripping portion (5213) is equipped with a merely flat surface without any particular feature to enhance grippability. Gripping portion (5213) terminates inwardly of the outer lateral edges of clamp pad (5212). This defines a shoulder (5214) in clamp pad (5212) that is generally configured to maintain clamp pad (5212) within the clamp arm assembly via electrode (5218) as described further below.

Clamp pad (5212) also comprises pad bumper (5216) defined in clamp pad (5212) at the proximal end of clamp pad (5212). Pad bumper (5216) is generally configured to maintain relative positioning between clamp pad (5212) and blade (5152) during clamping, and thereby act as a non-conductive gap setting feature to maintain spacing between blade (5152) and electrode (5218). Pad bumper (5216) comprises a first surface (5217) configured to contact surface (5153) of blade (5152). In the illustrated version, first surface (5217) of pad bumper (5216) is curved, which corresponds with the curved profile of rounded upper surface (5153) of blade (5152). Accordingly, it should be understood that the profile of first surface (5217) generally corresponds to the profile of blade (5152) at the location of contact such that first surface (5217) is configured to receive blade (5152).

Figure 42:
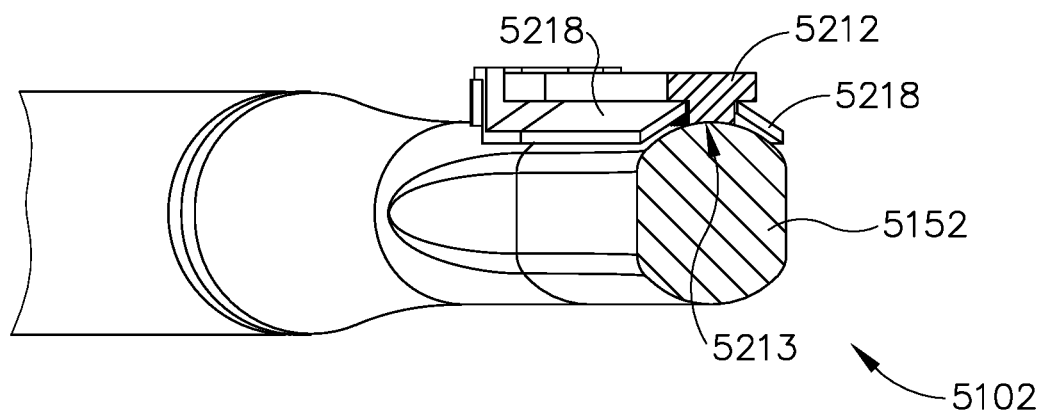
FIG. 42 depicts a cross-sectional view of the end effector of FIG. 41, with the end effector in a closed configuration, and with the cross-section taken at an intermediate region of the end effector.
Figure 44:
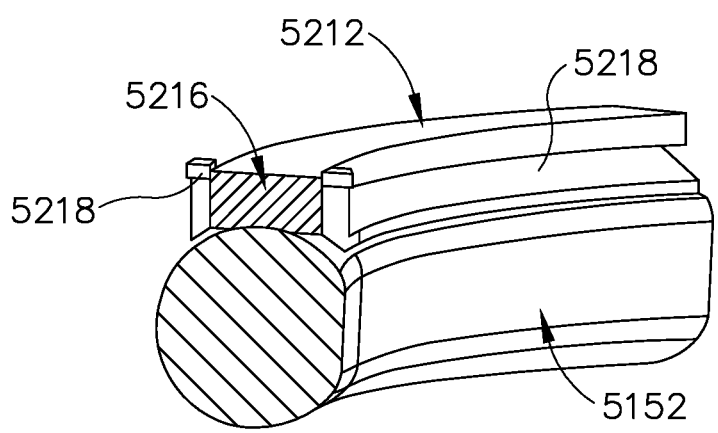
FIG. 44 depicts a cross-sectional view of the end effector of FIG. 41, and with the cross-section taken at a proximal region of the end effector.
Figure 45:
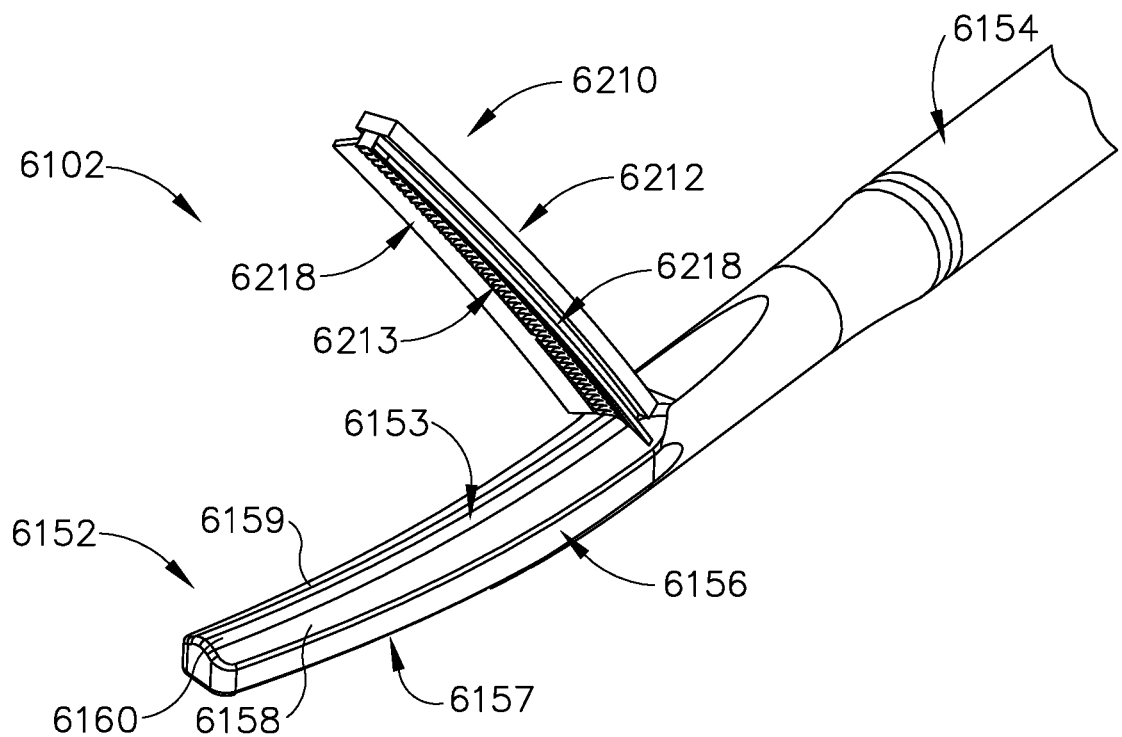
FIG. 45 depicts a perspective view of another exemplary end effector for use with the surgical instruments described herein, with the end effector in an open configuration.

As shown in the illustrated version, pad bumper (5216) further comprises flat shoulders (5215) on each longitudinal side of pad bumper (5216). When end effector (5102) is in an assembled state, pad bumper (5216) extends further towards rounded upper surface (5153) of blade (5152) compared to electrode (5218). In this configuration, when end effector (5102) is in a closed position as shown in FIGS. 42 and 44, pad bumper (5216) acts as a spacer or provides a spacing or gap setting function to prevent electrode (5218) from contacting blade (5152) and thereby causing a short circuit when RF electrosurgical energy is used to provide RF electrosurgical sealing. Pad bumper (5216) comprises a width that matches the width of clamp pad (5212). In the present version, shoulders (5215) that extend along each longitudinal side of pad bumper (5216) are located along a separate plane from shoulder (5214) that extends along the remainder of clamp pad (5212).

Electrode (5218) comprises a single relatively thin strip of relatively rigid electrically conducting material. In some examples electrode (5218) comprises an electrically conductive metal such as copper, gold, steel, aluminum, silver, etc. In still other examples, electrode (5218) comprises an electrically conductive non-metallic material such as conducting polymers, silicides, graphite, etc. The thickness of electrode (5218) is generally thinner than gripping portion (5213) of clamp pad (5212), such that gripping portion (5213) protrudes proudly past the surface of electrode (5218) facing blade (5152). However, electrode (5218) is still generally thick enough to maintain a suitable amount of structural rigidity. The particular shape of electrode (5218) generally corresponds to the shape of clamp pad (5212). In particular, electrode (5218) generally defines a shape similar to an outline of clamp pad (5212). Electrode (5218) further defines an opening (5219) therein. Opening (5219) is configured to receive gripping portion (5213) of clamp pad (5212) therethrough such that electrode (5218) is configured to engage with shoulder (5214) of clamp pad (5212).

In the illustrated version of FIGS. 40-44, when end effector (5102) is in the closed or clamping position, a tissue-contacting surface (5221) of electrode (5218) is oriented generally facing a longitudinal axis extending through blade (5152). In this manner, surface (5221) faces rounded upper surface (5153) of blade (45152). In the present example, surface (5221) is flat while upper surface (5153) is rounded. With this configuration, a gap between surface (5221) of electrode (5218) and upper surface (5153) of blade (5152) is smallest along a longitudinal centerline of electrode (5218). In some other versions, surface (5221) has a matching curvature to rounded upper surface (5153) such that the gap between surface (5221) and upper surface (5153) is consistent along the length of blade (5152) and electrode (5218).

When clamp pad assembly (5210) is assembled, clamp pad (5212) is first inserted into a clamp pad receiving channel of a clamp arm assembly, e.g. receiving channel (208) of clamp arm assembly (200). As described above, clamp pad receiving channel (208) is defined in the distal end of a body (202). Electrode (5218) is then inserted over clamp pad (5212), with electrode (5218) seating on shoulder (5214) of clamp pad (5212), and with gripping portion (5213) of clamp pad (5212) protruding through opening (5219). Electrode (5218) is then resistance welded or otherwise secured to body (202). In the present example, electrode (5218) is resistance welded in place to structural core (204) of body (202) at the proximal and distal ends of electrode (5218).

In other examples, electrode (5218) is resistance welded at any other suitable location in addition to, or in lieu of, welding at the distal and proximal ends of electrode (5218). In still other examples, resistance welds are omitted entirely and electrode (5218) is secured to body (202) by any other suitable means such as other welding processes and/or adhesive bonding, etc. It should be understood that once electrode (5218) is secured to body (202), electrode (5218) also couples clamp pad (5212) to body (202) by engagement between electrode (5218) and shoulder (5214) of clamp pad (5212). Accordingly, the thickness of electrode (5218) is generally thick enough to provide enough rigidity to couple clamp pad (5212) to body (202). In other versions, clamp pad assembly (5210) may be assembled with other clamp arm assemblies (400, 1200, 2200, 3200), as will be understood by those of ordinary skill in the art in view of the teachings herein.

Electrode (5218) is configured to cooperate with blade (5152) to provide bipolar RF electrosurgical energy to tissue that is captured between clamp pad assembly (5210) and blade (5152). In particular, electrode (5218) is activated with RF energy and blade (5152) provides a return path for the RF energy. It should therefore be understood that blade (5152) is capable of serving two distinct roles in the present example—one role of applying ultrasonic energy to tissue that is in contact with blade (5152) and another role of cooperating with electrode (5218) to provide bipolar RF energy to tissue that is captured between clamp pad assembly (5210) and blade (5152).

In some versions, the ultrasonic energy and RF energy are applied simultaneously. In some other versions, the ultrasonic energy and RF energy are applied in an automatically alternating fashion. In some other versions, the ultrasonic energy and RF energy are applied in a simple series (e.g., ultrasonic energy first, followed by RF energy). In some other versions, the ultrasonic energy and RF energy are selectively applied independently. Other suitable features that may be used to provide communication of RF energy through electrode (5218) and blade (5152) will be apparent to those of ordinary skill in the art in view of the teachings herein.

In the present example, because electrode (5218) is generally thinner than gripping portion (5213) of clamp pad (5212), gripping portion (5213) generally protrudes proudly from surface (5221) of electrode (5218) that faces blade (5152) so as to prevent blade (5152) from directly contacting electrode (5218) when end effector (5102) is in a closed or clamping configuration. Thus, it should be understood that electrode (5218) is generally not configured to physically contact blade (5152). However, as described above, electrical continuity for RF energy is generally achieved by passing electrical current through a patient's tissue as it is cut and/or sealed, and in some versions this electrical current flows between electrode (5218) and blade (5152). In this regard, end effector (5102) comprises multiple features that provide spacing to prevent contact between conductive blade (5152) and electrode (5218) to prevent short circuiting when using RF electrosurgical energy. As discussed above, one such feature is gripping portion (5213), and another such feature is pad bumper (5216).

The location of pad bumper (5216) is proximally positioned along clamp pad (5212) as discussed above. Furthermore, and as also described above, the pivoting action of the clamp arm assembly is provided at a pivoting location that is proximal to clamp pad assembly (5210). Accordingly, when moving the instrument to a closed position for clamping, pad bumper (5216) will contact surface (5153) of blade (5152) before gripping portion (5213) to prevent contact between blade (5152) and electrode (5218). Pad bumper (5216) thus prevents a short circuit when using RF electrosurgical energy.

Additionally, the size of pad bumper (5216), being wider and generally greater in surface area per unit of length along clamp pad (5212) compared to gripping portion (5213), allows for a substantially larger area of clamp pad (5212) to contact blade (5152). This greater area combined with the proximal location of pad bumper (5216) can contribute to less blade (5152) displacement and less heat build-up where pad bumper (5216) contacts blade (5152). This in turn reduces flow of pad material and warping of clamp pad (5212) so as to reduce the wear and lengthen the life or use cycle of clamp pad (5212).

As shown in the illustrated version, electrode (5218) extends proximally alongside pad bumper (5216). However, the width of electrode (5218) in this area alongside pad bumper (5216) is less compared to the width of electrode (5218) in the areas alongside gripping portion (5213) where shoulder (5214) is present. To maintain cut and seal quality and integrity, pad bumper (5216) and the accompanying reduced width electrode (5218) alongside pad bumper (5216) are positioned proximally of tissue stops (290, 1290, 1296, 2290, 2296). In this configuration, tissue is prevented from entering the proximal region where pad bumper (5216) is located. Therefore, tissue cutting and sealing is not required to occur along pad bumper (5216) region and instead is reserved for the area between gripping portion (5213) of clamp pad (5212) and blade (5152). In view of the teachings herein, various ways to position pad bumper (5216) relative to tissue stops (290, 1290, 1296, 2290, 2296) to achieve acceptable cutting and sealing performance while providing spacing features to prevent short circuits between electrode (5218) and blade (5152) will be apparent to those of ordinary skill in the art.

In an exemplary manufacturing process for blade (5152), a straight rod, e.g. a titanium rod, is turned down to the desired diameter. Next two flat side surfaces (5156) are milled into blade (5152). Next, blade (5152) is bent to the desired curve, e.g. using a mandrel. In view of the teachings herein, other ways to manufacture blade (5152) will be apparent to those of ordinary skill in the art.

Referring to FIGS. 42 and 44, in the illustrated version, electrode (5218) has no offset with blade (5152). Generally, electrode offset represents the amount of overlap of the electrode beyond the lateral edge of the blade from a profile view of the end effector. Thus, in the present example where there is no offset for electrode (5218), the width of electrode (5218) follows the width of blade (5152) along its length such that there is no overhang (positive offset) or setback (negative offset) of electrode (5218) relative to the side edges of blade (5152). As will be described further below, in other versions, some of which may include end effectors having rounded blades, electrode (5218) can be configured such that there is an offset relative to blade (5152), e.g. a positive offset where electrode (5218) overhangs blade (5152) on each side along the length of blade (5152).

In some versions of a rounded blade having an electrode with a positive offset of about 0.02 inches (0.5 millimeters), where the electrode width extends past the edges or side surfaces of the flat blade by about 0.02 inches (0.5 millimeters) on each side, improved hemostasis may be observed over a similar end effector without an offset electrode. In studying performance, burst pressure data may be collected from previously sealed tissue using both the end effector having a rounded blade with no offset, and the end effector having a rounded blade with the about 0.02 inch offset. By way of example only, three tissue types may be studied: bundles, large carotids, and Thyrocervical vessels. For all three tissue types, the average burst pressure may increase when using the end effector with the rounded blade and about 0.02 inch offset electrode. The burst pressure recorded may be the pressure at which the previously sealed tissue leaked. Thus a higher burst pressure would be indicative of a stronger seal. By way of example only, for tissue bundles, the burst pressure with the rounded blade with no offset may be about 817 mm Hg; while the burst pressure with the rounded blade with about 0.02 inch offset may be about 1103.5 mm Hg—an improvement of about 35%. For the large carotids, the burst pressure with the rounded blade with no offset may be about 895.5 mm Hg; while the burst pressure with the rounded blade with about 0.02 inch offset may be about 1430 mm Hg—an improvement of about 60%. For the Thyrocervical vessels, the burst pressure with the rounded blade with no offset may be about 774.5 mm Hg; while the burst pressure with the rounded blade with about 0.02 inch offset may be about 1182.5 mm Hg—an improvement of about 53%. In this testing, the results may thus be statistically significant for all studied tissue types.

In comparing the impact of blade geometry, the study of burst pressure data comparing the flat blade discussed above and the rounded blade discussed here may generally show that the seals with the flat blade have higher burst pressures at fail compared to seals with the rounded blade. This may be the case for both the offset electrode subset and the no offset electrode subset and across all tissue types, except that the rounded blade with the offset electrode may have a higher burst pressure compared to the flat blade with the offset electrode for Thyrocervical vessels.

D. Angled Blade

FIGS. 45-48 illustrate an end effector (6102) comprising an ultrasonic blade (6152) connected with a waveguide (6154), and a clamp pad assembly (6210) including a clamp pad (6212) and electrode (6218). Waveguide (6154) is connectable with the various shaft assemblies of the instruments described above in the same or similar manner as waveguide (154). Blade (6152) is configured with an angled upper surface (6153) for cutting and sealing, with flat side surfaces (6156) on each side and a flat lower surface (6157).

In the present example, an outline of upper surface (6153) in cross section comprises an upside-down "V" shape. Angled upper surface (6153) comprises a first portion (6158), a second portion (6159), and a peak (6160). In the present example, tangent lines to peak (6160) and first portion (6158) intersect and make an angle of about 30 degrees. Similarly, tangent lines to peak (6160) and second portion (6159) intersect and make an angle of about 30 degrees. In other versions, the angles formed by these tangent lines may be greater or lesser. Blade (6152) is also configured with an arcuate shape and a blunt distal end (6155) as shown. As discussed above, lower surface (6157) of blade (6152) may be protected by a heat shield as shown and described above with respect to other versions.

Clamp pad assembly (6210) is connectable with one of the various clamp arm assemblies of the instruments described above. For example, clamp pad assembly (6210) is connectable with clamp arm assembly (200) in the same or similar manner that clamp pad assembly (210) connects with clamp arm assembly (200). In view of the teachings herein, other ways in which clamp pad assembly (6210) connects with the various clamp arm assemblies described herein, including but not limited to clamp arm assemblies (200, 400, 1200, 2200, 3200), will be apparent to those of ordinary skill in the art.

Figure 47:
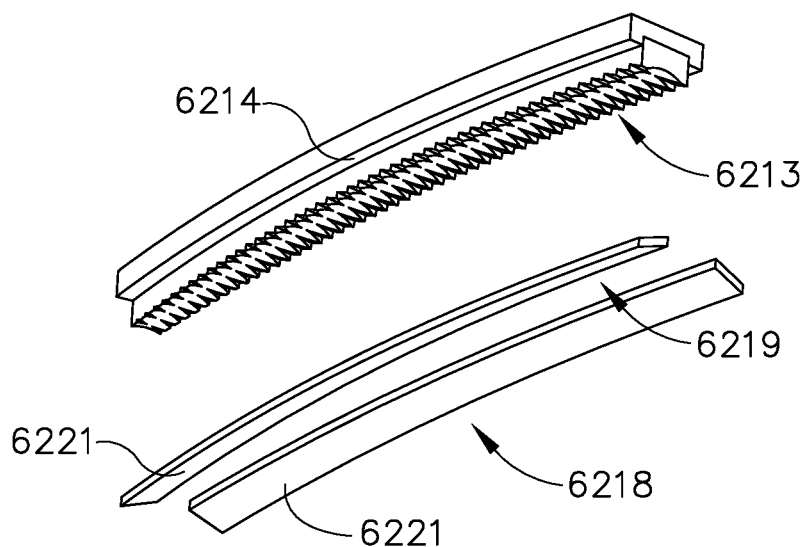
FIG. 47 depicts an exploded view of a clamp pad assembly of the end effector of FIG. 45.

FIG. 47 shows clamp pad assembly (6210) in greater detail. As can be seen, clamp pad assembly (6210) comprises a clamp pad (6212) and an electrode (6218). Clamp pad (6212) comprises a single generally homogenous insulating material such as polytetrafluoroethylene (PTFE), rubber, and/or other similar insulating materials. The particular shape of clamp pad (6212) generally corresponds to the shape of blade (6152). In particular, clamp pad (6212) generally defines a shape similar to an outline of blade (6152). In the illustrated version, blade (6152) and clamp pad (6212) widen as they extend proximally.

Clamp pad (6212) comprises a gripping portion (6213) configured to grip tissue and hold such tissue in position as the tissue is being clamped between clamp pad assembly (6210) and ultrasonic blade (6152). In the present example, gripping portion (6213) includes a repeating pattern of ribs or teeth to enhance the grippability of gripping portion (6213). In other examples, gripping portion (6213) is equipped with numerous other features to enhance grippability such as knurling, irregular surface patterns, or any other generally rough surface. In still other examples, gripping portion (6213) is equipped with a merely flat surface without any particular feature to enhance grippability. Gripping portion (6213) terminates inwardly of the outer lateral edges of clamp pad (6212). This defines a shoulder (6214) in clamp pad (6212) that is generally configured to maintain clamp pad (6212) within the clamp arm assembly via electrode (6218) as described further below. In the present example, gripping portion (6213) of clamp pad (6212) widens as clamp pad (6212) extends in the proximal direction.

In the illustrated version, clamp pad (6212) omits a pad bumper as described above. However, in other versions clamp pad (6212) comprises a pad bumper as described above. In view of the teachings herein, various ways to modify clamp pad (6212) and end effector (6102) to include a pad bumper will be apparent to those of ordinary skill in the art.

Electrode (6218) comprises a single relatively thin strip of relatively rigid electrically conducting material. In some examples electrode (6218) comprises an electrically conductive metal such as copper, gold, steel, aluminum, silver, etc. In still other examples, electrode (6218) comprises an electrically conductive non-metallic material such as conducting polymers, silicides, graphite, etc. The thickness of electrode (6218) is generally thinner than gripping portion (6213) of clamp pad (6212), such that gripping portion (6213) protrudes past the surface of electrode (6218) facing blade (6152). However, electrode (6218) is still generally thick enough to maintain a suitable amount of structural rigidity.

The particular shape of electrode (6218) generally corresponds to the shape of clamp pad (6212). In particular, electrode (6218) generally defines a shape similar to an outline of clamp pad (6212). Electrode (6218) further defines an opening (6219) therein. Opening (6219) is configured to receive gripping portion (6213) of clamp pad (6212) therethrough such that electrode (6218) is configured to engage with shoulder (6214) of clamp pad (6212). In the illustrated version of FIGS. 45-48, when end effector (6102) is in the closed or clamping position, a tissue-contacting surface (6221) of electrode (6218) is oriented generally parallel to first and second portions (6158, 6159) of angled upper surface (6153) of blade (6152).

When clamp pad assembly (6210) is assembled, clamp pad (6212) is first inserted into a clamp pad receiving channel of a clamp arm assembly, e.g. receiving channel (208) of clamp arm assembly (200). As described above, clamp pad receiving channel (208) is defined in the distal end of a body (202). Electrode (6218) is then inserted over clamp pad (6212), with electrode (6218) seating on shoulder (6214) of clamp pad (6212), and with gripping portion (6213) of clamp pad (6212) protruding through opening (6219). Electrode (6218) is then resistance welded or otherwise secured to body (202). In the present example, electrode (6218) is resistance welded in place to structural core (204) of body (202) at the proximal and distal ends of electrode (6218).

In other examples, electrode (6218) is resistance welded at any other suitable location in addition to, or in lieu of, welding at the distal and proximal ends of electrode (6218). In still other examples, resistance welds are omitted entirely and electrode (6218) is secured to body (202) by any other suitable means such as other welding processes and/or adhesive bonding, etc. It should be understood that once electrode (6218) is secured to body (202), electrode (6218) also couples clamp pad (6212) to body (202) by engagement between electrode (6218) and shoulder (6214) of clamp pad (6212). Accordingly, the thickness of electrode (6218) is generally thick enough to provide enough rigidity to couple clamp pad (6212) to body (202). In other versions, clamp pad assembly (6210) may be assembled with other clamp arm assemblies (400, 1200, 2200, 3200), as will be understood by those of ordinary skill in the art in view of the teachings herein.

Electrode (6218) is configured to cooperate with blade (6152) to provide bipolar RF electrosurgical energy to tissue that is captured between clamp pad assembly (6210) and blade (6152). In particular, electrode (6218) is activated with RF energy and blade (6152) provides a return path for the RF energy. It should therefore be understood that blade (6152) is capable of serving two distinct roles in the present example—one role of applying ultrasonic energy to tissue that is in contact with blade (6152) and another role of cooperating with electrode (6218) to provide bipolar RF energy to tissue that is captured between clamp pad assembly (6210) and blade (6152).

In some versions, the ultrasonic energy and RF energy are applied simultaneously. In some other versions, the ultrasonic energy and RF energy are applied in an automatically alternating fashion. In some other versions, the ultrasonic energy and RF energy are applied in a simple series (e.g., ultrasonic energy first, followed by RF energy). In some other versions, the ultrasonic energy and RF energy are selectively applied independently. Other suitable features that may be used to provide communication of RF energy through electrode (6218) and blade (6152) will be apparent to those of ordinary skill in the art in view of the teachings herein.

In the present example, because electrode (6218) is generally thinner than gripping portion (6213) of clamp pad (6212), gripping portion (6213) generally protrudes proudly from surface (6221) of electrode (6218) that faces blade (6152) so as to prevent blade (6152) from directly contacting electrode (6218) when end effector (6102) is in a closed or clamping configuration. Thus, it should be understood that electrode (6218) is generally not configured to physically contact blade (6152). However, as described above, electrical continuity for RF energy is generally achieved by passing electrical current through a patient's tissue as it is cut and/or sealed, and in some versions this electrical current flows between electrode (6218) and blade (6152). In this regard, end effector (6102) comprises features that provide spacing to prevent contact between conductive blade (6152) and electrode (6218) to prevent short circuiting when using RF electrosurgical energy.

Clamp pad (6212) widens as it extends proximally as discussed above. Furthermore, and as also described above, the pivoting action of the clamp arm assembly is provided at a pivoting location that is proximal to clamp pad assembly (6210). Accordingly, when moving the instrument to a closed position for clamping, the widest part of gripping portion (6213) of clamp pad (6212) will contact surface (6153) of blade (6152) before the narrower distal regions of gripping portion (6213). This configuration promotes alignment of clamp pad (6212) with blade (6152) and also promotes proper contact with blade (6152) to prevent contact between blade (6152) and electrode (6218). This configuration thus prevents a short circuit when using RF electrosurgical energy.

Additionally, the wider the proximal region of clamp pad (6212), and generally greater surface area per unit of length in this proximal region compared to the narrower distal region, allows for a substantially larger area of clamp pad (6212) to contact blade (6152). This greater area and its proximal location can contribute to less blade (6152) displacement and less heat build-up where the proximal region of clamp pad (6212) contacts blade (6152). This in turn reduces flow of pad material and warping of clamp pad (6212) so as to reduce the wear and lengthen the life or use cycle of clamp pad (6212).

While in the present example clamp pad (6212) widens as it extends proximally, in another version clamp pad (6212) has a constant width, with gripping portion (6213) widening as gripping portion (6213) extends proximally. In such an example, shoulder (6214) becomes narrower in width as shoulder (6214) extends proximally along clamp pad (6212), and electrode (6218) also becomes narrower in width as it extends proximally along clamp pad (6212). To maintain cut and seal quality and integrity, a proximal region of gripping portion (6213), and the accompanying reduced width electrode (6218) alongside, are positioned proximally of tissue stops (290, 1290, 1296, 2290, 2296). In this configuration tissue is prevented from entering the proximal region where electrode (6218) narrows. Therefore, tissue cutting and sealing is not required to occur along the most proximal region of clamp pad (6212) and instead is reserved for the remainder regions of clamp pad (6212) between gripping portion (6213) and blade (6152). In view of the teachings herein, various ways to position clamp pad (6212) relative to tissue stops (290, 1290, 1296, 2290, 2296) to achieve acceptable cutting and sealing performance while providing spacing features to prevent short circuits between electrode (6218) and blade (6152) will be apparent to those of ordinary skill in the art.

Figure 46:
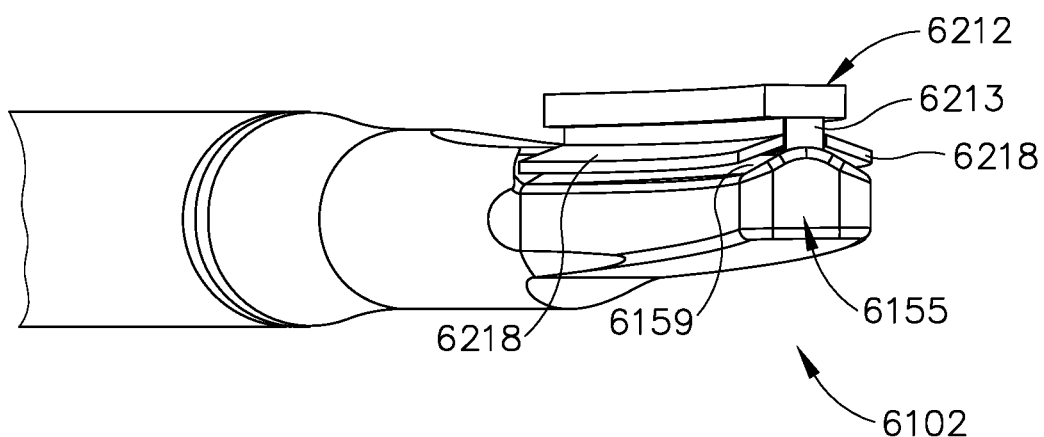
FIG. 46 depicts another perspective view of the end effector of FIG. 45, with the end effector in a closed configuration.
Figure 48:
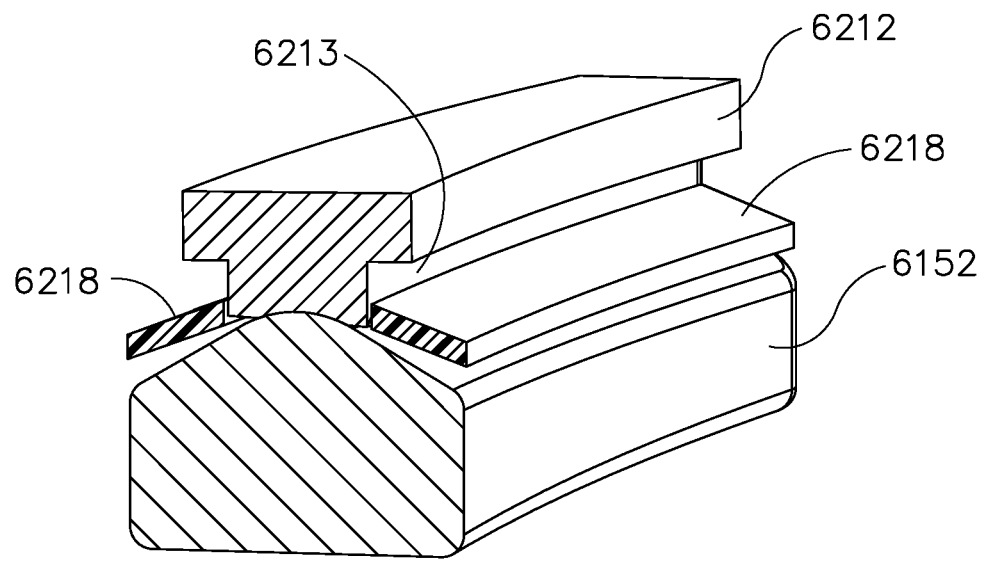
FIG. 48 depicts a cross-sectional view of the end effector of FIG. 45.
Figure 49:
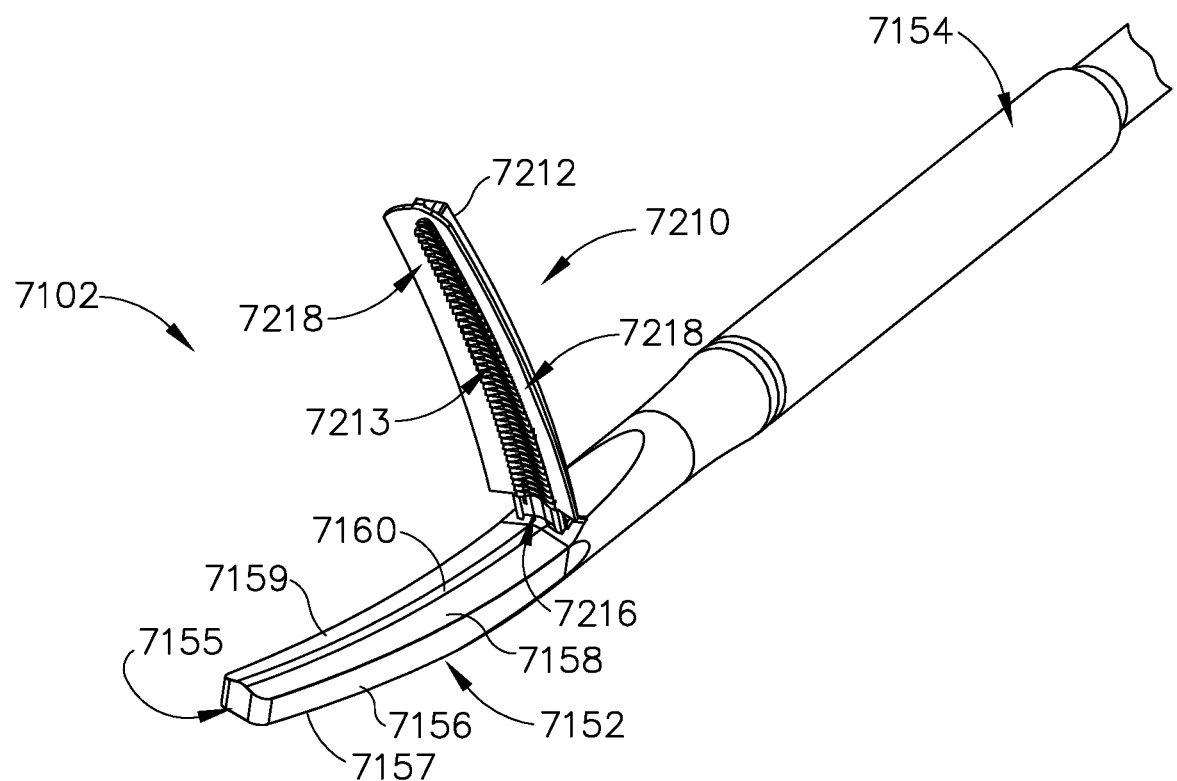
FIG. 49 depicts a perspective view of another exemplary end effector for use with the surgical instruments described herein, with the end effector in an open configuration.

Referring to FIGS. 46 and 48, in the illustrated version, electrode (6218) has no offset with blade (6152). Accordingly, the width of electrode (6218) follows the width of blade (6152) along its length such that there is no overhang (positive offset) or setback (negative offset) of electrode (6218) relative to the flat side surfaces (6156) of blade (6152). In other versions, some of which may include end effectors having angled blades, electrode (6218) can be configured such that there is an offset relative to blade (6152), e.g. a positive offset where electrode (6218) overhangs blade (6152) on each side along the length of blade (6152).

E. Alternative Angled Blade with Offset Electrode and Proximal Pad Bumper

FIGS. 49-52 illustrate an end effector (7102) comprising an ultrasonic blade (7152) connected with a waveguide (7154), and a clamp pad assembly (7210) including a clamp pad (7212) and electrode (7218). Waveguide (7154) is connectable with the various shaft assemblies of the instruments described above in the same or similar manner as waveguide (154). Blade (7152) is configured with an angled upper surface (7153) for cutting and sealing, with flat side surfaces (7156) on each side and a flat lower surface (7157).

In the present example, an outline of upper surface (7153) in cross section comprises an upside-down "V" shape. Angled upper surface (7153) comprises a first portion (7158), a second portion (7159), and a peak (7160). In the present example, tangent lines to peak (7160) and first portion (7158) intersect and make an angle of about 15 degrees. Similarly, tangent lines to peak (7160) and second portion (7159) intersect and make an angle of about 15 degrees. In other versions, the angles formed by these tangent lines may be greater or lesser. Blade (7152) is also configured with an arcuate shape and a blunt distal end (7155) as shown. As discussed above, lower surface (7157) of blade (7152) may be protected by a heat shield as shown and described above with respect to other versions.

Clamp pad assembly (7210) is connectable with one of the various clamp arm assemblies of the instruments described above. For example, clamp pad assembly (7210) is connectable with clamp arm assembly (200) in the same or similar manner that clamp pad assembly (210) connects with clamp arm assembly (200). In view of the teachings herein, other ways in which clamp pad assembly (7210) may connect with the various clamp arm assemblies described herein, including but not limited to clamp arm assemblies (200, 400, 1200, 2200, 3200), will be apparent to those of ordinary skill in the art.

Figure 51:
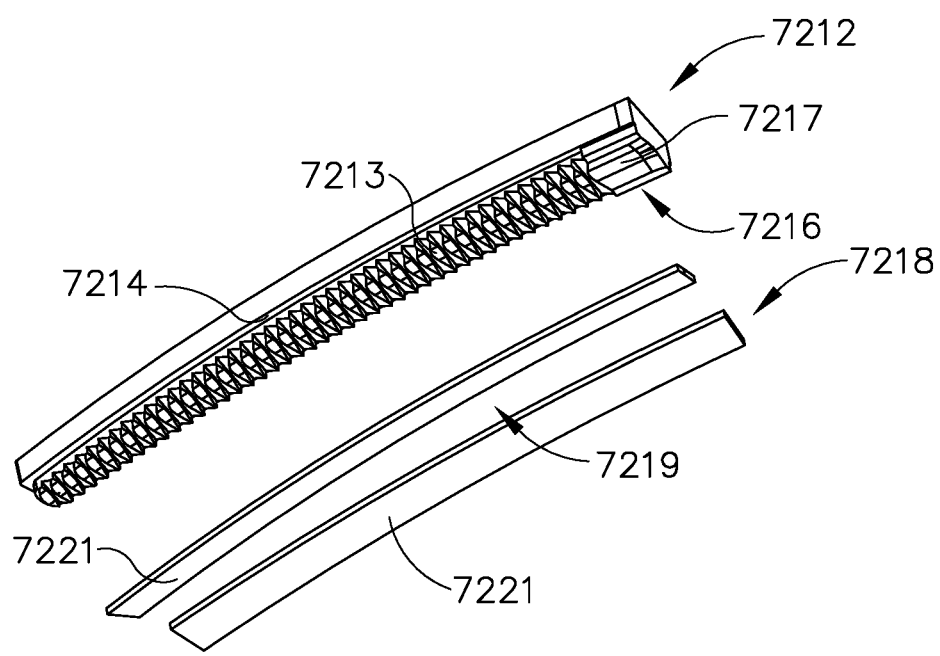
FIG. 51 depicts an exploded view of a clamp pad assembly of the end effector of FIG. 49.

FIG. 51 shows clamp pad assembly (7210) in greater detail. As can be seen, clamp pad assembly (7210) comprises a clamp pad (7212) and an electrode (7218). Clamp pad (7212) comprises a single generally homogenous insulating material such as polytetrafluoroethylene (PTFE), rubber, and/or other similar insulating materials. The particular shape of clamp pad (7212) generally corresponds to the shape of blade (7152). In particular, clamp pad (7212) generally defines a shape similar to an outline of blade (7152). In the illustrated version, blade (7152) and clamp pad (7212) widen as they extend proximally. Clamp pad (7212) comprises a gripping portion (7213) configured to grip tissue and hold such tissue in position as the tissue is being clamped between clamp pad assembly (7210) and ultrasonic blade (7152). In the present example, gripping portion (7213) includes a repeating pattern of ribs or teeth to enhance the grippability of gripping portion (7213).

In other examples, gripping portion (7213) is equipped with numerous other features to enhance grippability such as knurling, irregular surface patterns, or any other generally rough surface. In still other examples, gripping portion (7213) is equipped with a merely flat surface without any particular feature to enhance grippability. Gripping portion (7213) terminates inwardly of the outer lateral edges of clamp pad (7212). This defines a shoulder (7214) in clamp pad (7212) that is generally configured to maintain clamp pad (7212) within the clamp arm assembly via electrode (7218) as described further below. In the present example, gripping portion (7213) of clamp pad (7212) widens as clamp pad (7212) extends in the proximal direction.

Clamp pad (7212) also comprises pad bumper (7216) defined in clamp pad (7212) at the proximal end of clamp pad (7212). Pad bumper (7216) is generally configured to maintain relative positioning between clamp pad (7212) and blade (7152) during clamping, and thereby act as a non-conductive gap setting feature to maintain spacing between blade (7152) and electrode (7218). Pad bumper (7216) comprises a first surface (7217) configured to contact surface (7153) of blade (7152). In the illustrated version, first surface (7217) of pad bumper (7216) is angled, which corresponds with the angled profile of upper surface (7153) of blade (7152). Accordingly, it should be understood that the profile of first surface (7217) generally corresponds to the profile of blade (7152) at the location of contact such that first surface (7217) is configured to receive blade (7152).

Figure 50:
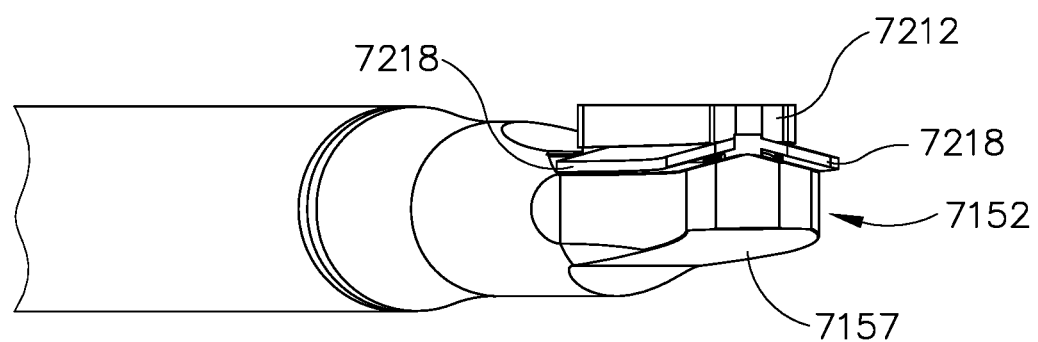
FIG. 50 depicts another perspective view of the end effector of FIG. 49, with the end effector in a closed configuration.
Figure 52:
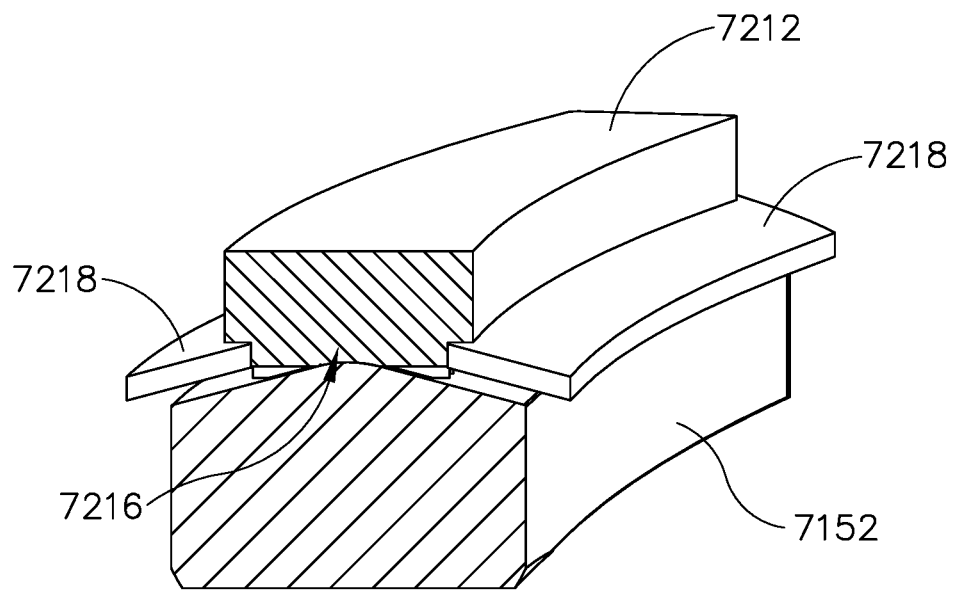
FIG. 52 depicts a cross-sectional view of the end effector of FIG. 49.
Figure 53:
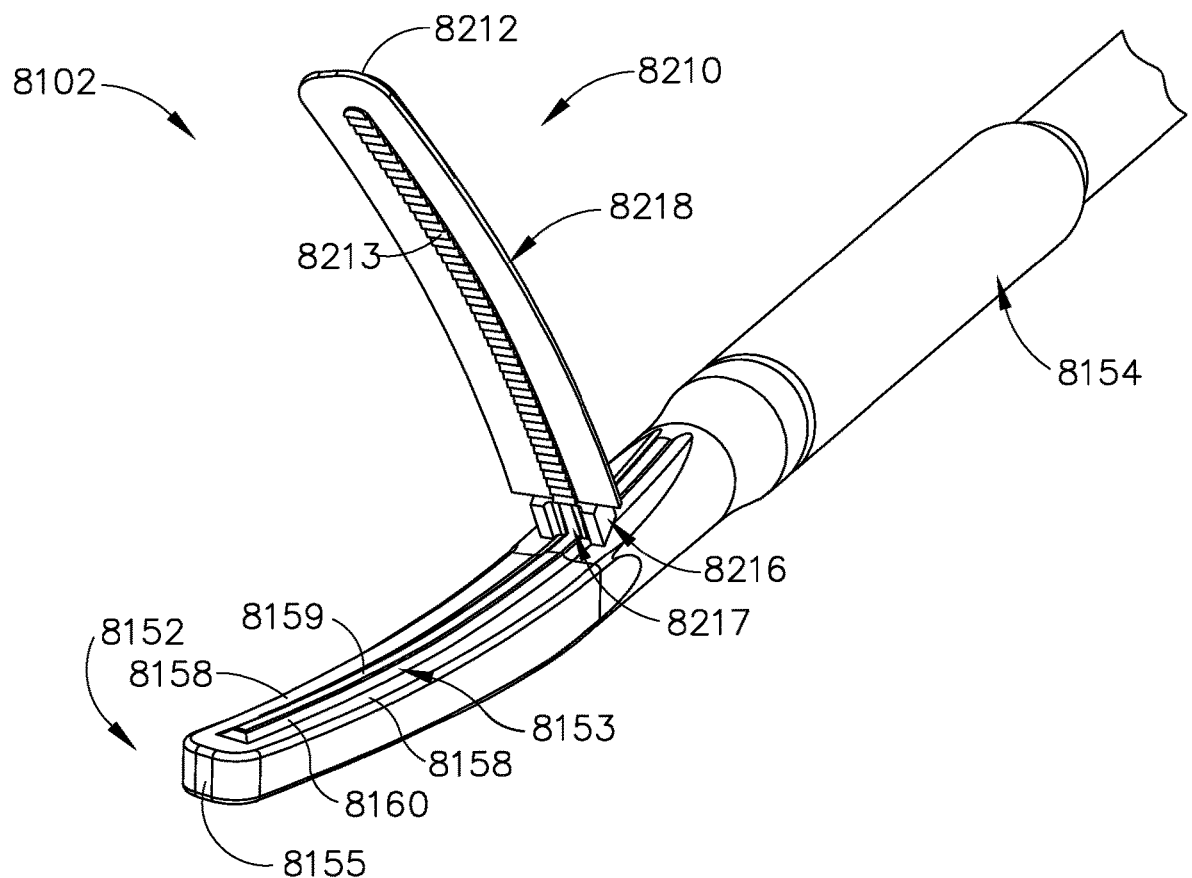
FIG. 53 depicts a perspective view of another exemplary end effector for use with the surgical instruments described herein, with the end effector in an open configuration.

Pad bumper (7216) comprises a width that matches the width of clamp pad (7212). As shown in the illustrated version, shoulders (7214) terminate adjacent to pad bumper (7216), and similarly electrode (7218) terminates at pad bumper (7216). When end effector (7102) is in an assembled state, pad bumper (7216) extends further towards angled upper surface (7153) of blade (7152) compared to electrode (7218). In this configuration, when end effector (7102) is in a closed position as shown in FIGS. 50 and 52, pad bumper (7216) acts as a spacer or provides a spacing or gap setting function to prevent electrode (7218) from contacting blade (7152) and thereby causing a short circuit when RF electrosurgical energy is used to provide RF electrosurgical sealing.

Electrode (7218) comprises a single relatively thin strip of relatively rigid electrically conducting material. In some examples electrode (7218) comprises an electrically conductive metal such as copper, gold, steel, aluminum, silver, etc. In still other examples, electrode (7218) comprises an electrically conductive non-metallic material such as conducting polymers, silicides, graphite, etc. The thickness of electrode (7218) is generally thinner than gripping portion (7213) of clamp pad (7212), such that gripping portion (7213) protrudes past the surface of electrode (7218) facing blade (7152). However, electrode (7218) is still generally thick enough to maintain a suitable amount of structural rigidity.

The particular shape of electrode (7218) generally corresponds to the shape of clamp pad (7212). In particular, electrode (7218) generally defines a shape similar to an outline of clamp pad (7212), excluding clamp pad bumper (7216). Electrode (7218) further defines an opening (7219) therein. Opening (7219) is configured to receive gripping portion (7213) of clamp pad (7212) therethrough such that electrode (7218) is configured to engage with shoulder (7214) of clamp pad (7212). In the illustrated version of FIGS. 49-52, when end effector (7102) is in the closed or clamping position, a tissue-contacting surface (7221) of electrode (7218) is oriented generally parallel to first and second portions (7158, 7159) of angled upper surface (7153) of blade (7152).

When clamp pad assembly (7210) is assembled, clamp pad (7212) is first inserted into a clamp pad receiving channel of a clamp arm assembly, e.g. receiving channel (208) of clamp arm assembly (200). As described above, clamp pad receiving channel (208) is defined in the distal end of a body (202). Electrode (7218) is then inserted over clamp pad (7212), with electrode (7218) seating on shoulder (7214) of clamp pad (7212), and with gripping portion (7213) of clamp pad (7212) protruding through opening (7219). Electrode (7218) is then resistance welded or otherwise secured to body (202). In the present example, electrode (7218) is resistance welded in place to structural core (204) of body (202) at the proximal and distal ends of electrode (7218).

In other examples, electrode (7218) is resistance welded at any other suitable location in addition to, or in lieu of, welding at the distal and proximal ends of electrode (7218). In still other examples, resistance welds are omitted entirely and electrode (7218) is secured to body (202) by any other suitable means such as other welding processes and/or adhesive bonding, etc. It should be understood that once electrode (7218) is secured to body (202), electrode (7218) also couples clamp pad (7212) to body (202) by engagement between electrode (7218) and shoulder (7214) of clamp pad (7212). Accordingly, the thickness of electrode (7218) is generally thick enough to provide enough rigidity to couple clamp pad (7212) to body (202). In other versions, clamp pad assembly (7210) may be assembled with other clamp arm assemblies (400, 1200, 2200, 3200), as will be understood by those of ordinary skill in the art in view of the teachings herein.

Electrode (7218) is configured to cooperate with blade (7152) to provide bipolar RF electrosurgical energy to tissue that is captured between clamp pad assembly (7210) and blade (7152). In particular, electrode (7218) is activated with RF energy and blade (7152) provides a return path for the RF energy. It should therefore be understood that blade (7152) is capable of serving two distinct roles in the present example—one role of applying ultrasonic energy to tissue that is in contact with blade (7152) and another role of cooperating with electrode (7218) to provide bipolar RF energy to tissue that is captured between clamp pad assembly (7210) and blade (7152).

In some versions, the ultrasonic energy and RF energy are applied simultaneously. In some other versions, the ultrasonic energy and RF energy are applied in an automatically alternating fashion. In some other versions, the ultrasonic energy and RF energy are applied in a simple series (e.g., ultrasonic energy first, followed by RF energy). In some other versions, the ultrasonic energy and RF energy are selectively applied independently. Other suitable features that may be used to provide communication of RF energy through electrode (7218) and blade (7152) will be apparent to those of ordinary skill in the art in view of the teachings herein.

In the present example, because electrode (7218) is generally thinner than gripping portion (7213) of clamp pad (7212), gripping portion (7213) generally protrudes proudly from surface (7221) of electrode (7218) that faces blade (7152) so as to prevent blade (7152) from directly contacting electrode (7218) when end effector (7102) is in a closed or clamping configuration. Thus, it should be understood that electrode (7218) is generally not configured to physically contact blade (7152). However, as described above, electrical continuity for RF energy is generally achieved by passing electrical current through a patient's tissue as it is cut and/or sealed, and in some versions this electrical current flows between electrode (7218) and blade (7152). In this regard, end effector (7102) comprises multiple features that provide spacing to prevent contact between conductive blade (7152) and electrode (7218) to prevent short circuiting when using RF electrosurgical energy. As discussed above, one such feature is gripping portion (7213), and another such feature is pad bumper (7216).

The location of pad bumper (7216) is proximally positioned along clamp pad (7212) as discussed above. Furthermore, and as also described above, the pivoting action of the clamp arm assembly is provided at a pivoting location that is proximal to clamp pad assembly (7210). Accordingly, when moving the instrument to a closed position for clamping, pad bumper (7216) will contact surface (7153) of blade (7152) before gripping portion (7213) to prevent contact between blade (7152) and electrode (7218) and thereby a short circuit when using RF electrosurgical energy. Additionally, the size of pad bumper (7216), being wider and generally greater in surface area per unit of length along clamp pad (7212) compared to gripping portion (7213), allows for a substantially larger area of clamp pad (7212) to contact blade (7152). This greater area combined with the proximal location of pad bumper (7216) can contribute to less blade (7152) displacement and less heat build-up where pad bumper (7216) contacts blade (7152). This in turn reduces flow of pad material and warping of clamp pad (7212) so as to reduce the wear and lengthen the life or use cycle of clamp pad (7212).

As shown in the illustrated version, electrode (7218) extends proximally alongside clamp pad (7212) for the length of gripping portion (7213). However, electrode (7218) terminates at pad bumper (7216) and thus is absent in the area alongside pad bumper (7216). To maintain cut and seal quality and integrity, pad bumper (7216) is positioned proximal of tissue stops (290, 1290, 1296, 2290, 2296). In this configuration tissue is prevented from entering the proximal region where pad bumper (7216) is located. Therefore, tissue cutting and sealing is not required to occur along pad bumper (7216) region and instead is reserved for the area between gripping portion (7213) of clamp pad (7212) and blade (7152). In view of the teachings herein, various ways to position pad bumper (7216) relative to tissue stops (290, 1290, 1296, 2290, 2296) to achieve acceptable cutting and sealing performance while providing spacing features to prevent short circuits between electrode (7218) and blade (7152) will be apparent to those of ordinary skill in the art.

Referring to FIGS. 50 and 52, in the illustrated version, electrode (7218) has a positive offset with blade (7152). Accordingly, the width of electrode (7218) extends beyond the width of blade (7152) along its length such that there is an overhang (positive offset) of electrode (7218) relative to the flat side surfaces (7156) of blade (7152). In the present example, the offset is about 0.02 inches (0.5 millimeters) such that the amount of overhang of electrode (7218) relative to blade (7152) along each side of blade (7152) is about 0.02 inches (0.5 millimeters.) In other versions, some of which may include end effectors having angled blades, electrode (7218) can be configured such that there is greater, less, or no offset relative to blade (7152).

F. Bumped Blade with Offset Electrode and Proximal Pad Bumper

FIGS. 53-56 illustrate an end effector (8102) comprising an ultrasonic blade (8152) connected with a waveguide (8154), and a clamp pad assembly (8210) including a clamp pad (8212) and electrode (8218). Waveguide (8154) is connectable with the various shaft assemblies of the instruments described above in the same or similar manner as waveguide (154).

Blade (8152) is configured with a raised surface (8153) surrounded by a flat surface (8158) for cutting and sealing. Raised surface (8153) is generally centered along the length of blade (8152). Raised surface (8153) comprises an upper flat surface (8159) and sloped side surfaces (8160). Blade (8152) is also configured with an arcuate shape and a blunt distal end (8155) as shown. As discussed above, the opposite side of blade (8152) to raised surface (8153) and flat surface (8158) may be protected by a heat shield as shown and described above with respect to other versions.

Clamp pad assembly (8210) is connectable with one of the various clamp arm assemblies of the instruments described above. For example, clamp pad assembly (8210) is connectable with clamp arm assembly (200) in the same or similar manner that clamp pad assembly (210) connects with clamp arm assembly (200). In view of the teachings herein, other ways in which clamp pad assembly (8210) may be connected with the various clamp arm assemblies described herein, including but not limited to clamp arm assemblies (200, 400, 1200, 2200, 3200), will be apparent to those of ordinary skill in the art.

Figure 55:
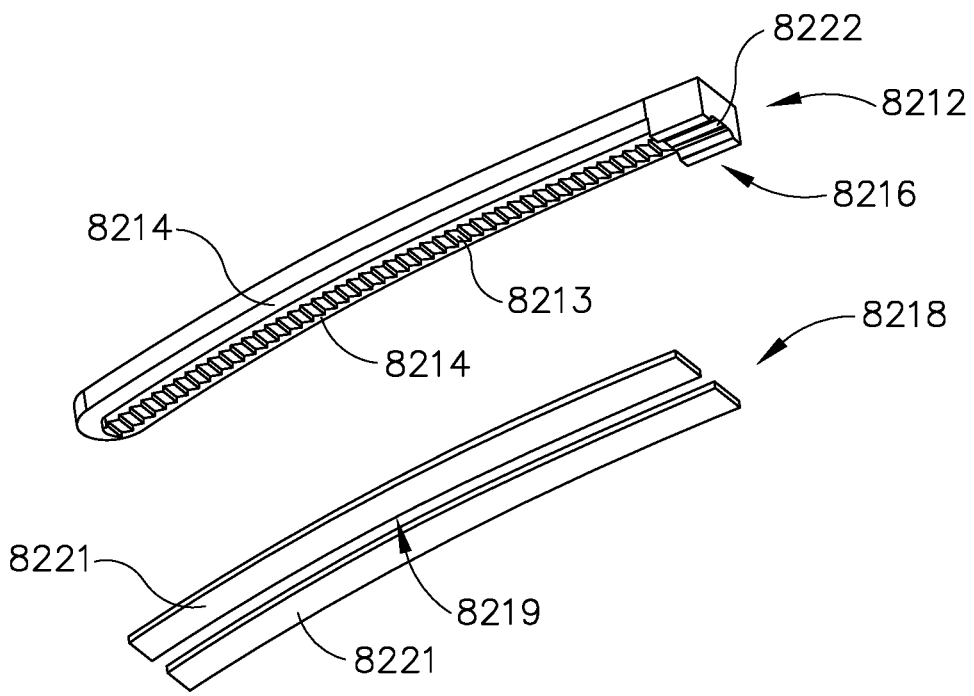
FIG. 55 depicts an exploded view of a clamp pad assembly of the end effector of FIG. 53.

FIG. 55 shows clamp pad assembly (8210) in greater detail. As can be seen, clamp pad assembly (8210) comprises a clamp pad (8212) and an electrode (8218). Clamp pad (8212) comprises a single generally homogenous insulating material such as polytetrafluoroethylene (PTFE), rubber, and/or other similar insulating materials. The particular shape of clamp pad (8212) generally corresponds to the shape of blade (8152). In particular, clamp pad (8212) generally defines a shape similar to an outline of blade (8152). Clamp pad (8212) comprises a gripping portion (8213) configured to grip tissue and hold such tissue in position as the tissue is being clamped between clamp pad assembly (8210) and ultrasonic blade (8152).

In the present example, gripping portion (8213) includes a repeating pattern of ribs or teeth to enhance the grippability of gripping portion (8213). In other examples, gripping portion (8213) is equipped with numerous other features to enhance grippability such as knurling, irregular surface patterns, or any other generally rough surface. In still other examples, gripping portion (8213) is equipped with a merely flat surface without any particular feature to enhance grippability. Gripping portion (8213) terminates inwardly of the outer lateral edges of clamp pad (8212). This defines a shoulder (8214) in clamp pad (8212) that is generally configured to maintain clamp pad (8212) within the clamp arm assembly via electrode (8218) as described further below.

Clamp pad (8212) also comprises pad bumper (8216) defined in clamp pad (8212) at the proximal end of clamp pad (8212). Pad bumper (8216) is generally configured to maintain relative positioning between clamp pad (8212) and blade (8152) during clamping, and thereby act as a non-conductive gap setting feature to maintain spacing between blade (8152) and electrode (8218). Pad bumper (8216) comprises a first surface (8217) configured to contact raised surface (8153) and flat surface (8158) of blade (8152). In the illustrated version, first surface (8217) of pad bumper (8216) comprises a recess (8222), which corresponds with raised surface (8153) of blade (8152) such that a proximal region of raised surface (8153) fits within recess (8219). Accordingly, it should be understood that the profile of first surface (8217) generally corresponds to the profile of blade (8152) at the location of contact such that first surface (8217) is configured to receive blade (8152).

Figure 54:
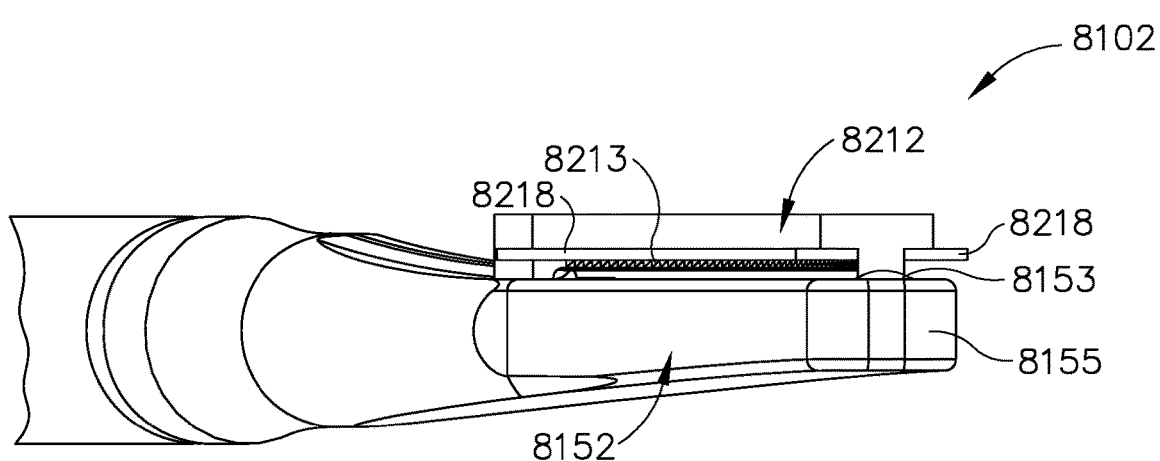
FIG. 54 depicts another perspective view of the end effector of FIG. 53, with the end effector in a closed configuration.
Figure 56:
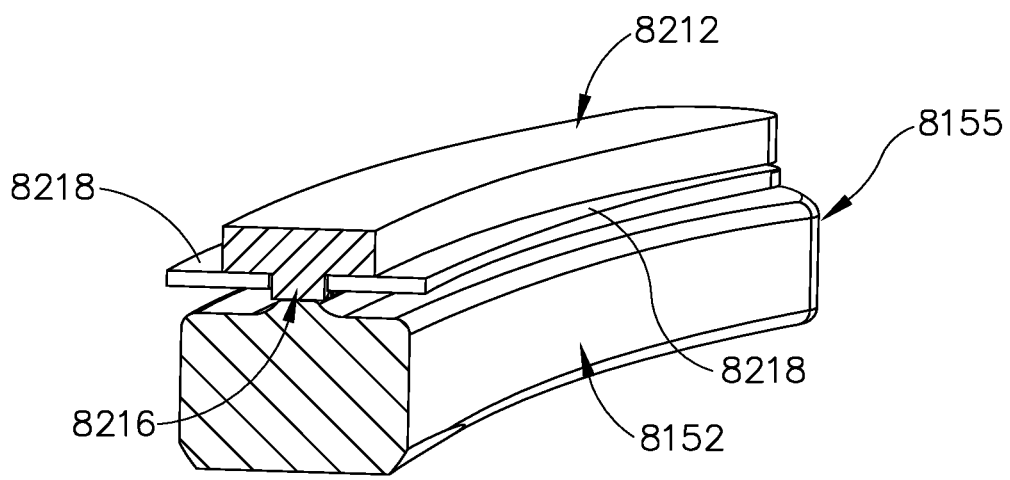
FIG. 56 depicts a cross-sectional view of the end effector of FIG. 53.

Pad bumper (8216) comprises a width that matches the width of clamp pad (8212). As shown in the illustrated version, shoulders (8214) terminate adjacent to pad bumper (8216), and similarly electrode (8218) terminates at pad bumper (8216). When end effector (8102) is in an assembled state, pad bumper (8216) extends further towards raised surface (8153) and flat surface (8158) of blade (8152) compared to electrode (8218). In this configuration, when end effector (8102) is in a closed position as shown in FIGS. 54 and 56, pad bumper (8216) acts as a spacer or provides a spacing to prevent electrode (8218) from contacting blade (8152) and thereby causing a short circuit when RF electrosurgical energy is used to provide RF electrosurgical sealing.

Electrode (8218) comprises a single relatively thin strip of relatively rigid electrically conducting material. In some examples electrode (8218) comprises an electrically conductive metal such as copper, gold, steel, aluminum, silver, etc. In still other examples, electrode (8218) comprises an electrically conductive non-metallic material such as conducting polymers, silicides, graphite, etc. The thickness of electrode (8218) is generally thinner than gripping portion (8213) of clamp pad (8212), such that gripping portion (8213) protrudes past the surface of electrode (8218) facing blade (8152). However, electrode (8218) is still generally thick enough to maintain a suitable amount of structural rigidity.

The particular shape of electrode (8218) generally corresponds to the shape of clamp pad (8212). In particular, electrode (8218) generally defines a shape similar to an outline of clamp pad (8212) excluding clamp pad bumper (8216). Electrode (8218) further defines an opening (8219) therein. Opening (8219) is configured to receive gripping portion (8213) of clamp pad (8212) therethrough such that electrode (8218) is configured to engage with shoulder (8214) of clamp pad (8212). In the illustrated version of FIGS. 54 and 56, when end effector (8102) is in the closed or clamping position, a tissue-contacting surface (8221) of electrode (8218) is oriented generally parallel to upper flat surface (8159) of raised surface (8153) and flat surface (8158) of blade (8152).

When clamp pad assembly (8210) is assembled, clamp pad (8212) is first inserted into a clamp pad receiving channel of a clamp arm assembly, e.g. receiving channel (208) of clamp arm assembly (200). As described above, clamp pad receiving channel (208) is defined in the distal end of a body (202). Electrode (8218) is then inserted over clamp pad (8212), with electrode (8218) seating on shoulder (8214) of clamp pad (8212), and with gripping portion (8213) of clamp pad (8212) protruding through opening (8219). Electrode (8218) is then resistance welded or otherwise secured to body (202). In the present example, electrode (8218) is resistance welded in place to structural core (204) of body (202) at the proximal and distal ends of electrode (8218). In other examples, electrode (8218) is resistance welded at any other suitable location in addition to, or in lieu of, welding at the distal and proximal ends of electrode (8218). In still other examples, resistance welds are omitted entirely and electrode (8218) is secured to body (202) by any other suitable means such as other welding processes and/or adhesive bonding, etc.

It should be understood that once electrode (8218) is secured to body (202), electrode (8218) also couples clamp pad (8212) to body (202) by engagement between electrode (8218) and shoulder (8214) of clamp pad (8212). Accordingly, the thickness of electrode (8218) is generally thick enough to provide enough rigidity to couple clamp pad (8212) to body (202). In other versions, clamp pad assembly (8210) may be assembled with other clamp arm assemblies (400, 1200, 2200, 3200), as will be understood by those of ordinary skill in the art in view of the teachings herein.

Electrode (8218) is configured to cooperate with blade (8152) to provide bipolar RF electrosurgical energy to tissue that is captured between clamp pad assembly (8210) and blade (8152). In particular, electrode (8218) is activated with RF energy and blade (8152) provides a return path for the RF energy. It should therefore be understood that blade (8152) is capable of serving two distinct roles in the present example—one role of applying ultrasonic energy to tissue that is in contact with blade (8152) and another role of cooperating with electrode (8218) to provide bipolar RF energy to tissue that is captured between clamp pad assembly (8210) and blade (8152).

In some versions, the ultrasonic energy and RF energy are applied simultaneously. In some other versions, the ultrasonic energy and RF energy are applied in an automatically alternating fashion. In some other versions, the ultrasonic energy and RF energy are applied in a simple series (e.g., ultrasonic energy first, followed by RF energy). In some other versions, the ultrasonic energy and RF energy are selectively applied independently. Other suitable features that may be used to provide communication of RF energy through electrode (8218) and blade (8152) will be apparent to those of ordinary skill in the art in view of the teachings herein.

In the present example, because electrode (8218) is generally thinner than gripping portion (8213) of clamp pad (8212), gripping portion (8213) generally protrudes proudly from surface (8221) of electrode (8218) that faces blade (8152) so as to prevent blade (8152) from directly contacting electrode (8218) when end effector (8102) is in a closed or clamping configuration. Thus, it should be understood that electrode (8218) is generally not configured to physically contact blade (8152). However, as described above, electrical continuity for RF energy is generally achieved by passing electrical current through a patient's tissue as it is cut and/or sealed, and in some versions this electrical current flows between electrode (8218) and blade (8152). In this regard, end effector (8102) comprises multiple features that provide spacing to prevent contact between conductive blade (8152) and electrode (8218) to prevent short circuiting when using RF electrosurgical energy. As discussed above, one such feature is gripping portion (8213), and another such feature is pad bumper (8216).

The location of pad bumper (8216) is proximally positioned along clamp pad (8212) as discussed above. Furthermore, and as also described above, the pivoting action of the clamp arm assembly is provided at a pivoting location that is proximal to clamp pad assembly (8210). Accordingly, when moving the instrument to a closed position for clamping, pad bumper (8216) will contact surface (8153) of blade (8152) before gripping portion (8213) to prevent contact between blade (8152) and electrode (8218). Pad bumper (8216) will thus prevent a short circuit when using RF electrosurgical energy.

Additionally, the size of pad bumper (8216), being wider and generally greater in surface area per unit of length along clamp pad (8212) compared to gripping portion (8213), allows for a substantially larger area of clamp pad (8212) to contact blade (8152). This greater area combined with the proximal location of pad bumper (8216) can contribute to less blade (8152) displacement and less heat build-up where pad bumper (8216) contacts blade (8152). This in turn reduces flow of pad material and warping of clamp pad (8212) so as to reduce the wear and lengthen the life or use cycle of clamp pad (8212).

As shown in the illustrated version, electrode (8218) extends proximally alongside clamp pad (8212) for the length of gripping portion (8213). However, electrode (8218) terminates at pad bumper (8216) and thus is absent in the area alongside pad bumper (8216). To maintain cut and seal quality and integrity, pad bumper (8216) is positioned proximal of tissue stops (290, 1290, 1296, 2290, 2296). In this configuration tissue is prevented from entering the proximal region where pad bumper (8216) is located. Therefore, tissue cutting and sealing is not required to occur along pad bumper (8216) region and instead is reserved for the area between gripping portion (8213) of clamp pad (8212) and blade (8152). In view of the teachings herein, various ways to position pad bumper (8216) relative to tissue stops (290, 1290, 1296, 2290, 2296) to achieve acceptable cutting and sealing performance while providing spacing features to prevent short circuits between electrode (8218) and blade (8152) will be apparent to those of ordinary skill in the art.

Referring to FIGS. 54 and 56, in the illustrated version, electrode (8218) has a positive offset with blade (8152). Accordingly, the width of electrode (8218) extends beyond the width of blade (8152) along its length such that there is an overhang (positive offset) of electrode (8218) relative to the flat side surfaces (8156) of blade (8152). In the present example, the offset is about 0.02 inches (0.5 millimeters) such that the amount of overhang of electrode (8218) relative to blade (8152) along each side of blade (8152) is about 0.02 inches (0.5 millimeters). In other versions, some of which may include end effectors having blades with raised surfaces surrounded by a flat surface, electrode (8218) can be configured such that there is greater, less, or no offset relative to blade (8152).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body, wherein the body includes an electrical conductor; (b) an ultrasonic blade extending distally from the body, wherein the ultrasonic blade is operable to apply ultrasonic energy to tissue; (c) a clamp arm pivotably coupled with the body at a pivot assembly, wherein the clamp arm is operable to compress tissue against the ultrasonic blade, wherein the clamp arm comprises an electrode operable to apply RF energy to tissue; and (d) a resilient member located within the pivot assembly, wherein the resilient member is configured to provide electrical continuity between the electrode of the clamp arm and the electrical conductor of the body.

Example 2

The surgical instrument of Example 1, wherein the clamp arm is removable from the body.

Example 3

The surgical instrument of any one or more of Examples 1 through 2, wherein the clamp arm further comprises an conductive plate, wherein the conductive plate provides a path for electrical continuity between the electrode and the resilient member.

Example 4

The surgical instrument of any one or more of Examples 1 through 3, wherein the electrical conductor comprises a conductive member extending about a proximal portion of the ultrasonic blade, wherein the resilient member is configured to resiliently bear against the conductive member.

Example 5

The surgical instrument of Example 4, wherein the conductive member comprises a tube.

Example 6

The surgical instrument of any one or more of Examples 1 through 5, wherein the resilient member comprises a spring arm.

Example 7

The surgical instrument of any one or more of Examples 1 through 6, wherein the electrical conductor is in communication with an RF energy transmission source.

Example 8

The surgical instrument of any one or more of Examples 1 through 7, wherein the ultrasonic blade is configured to cooperate with the electrode to apply bipolar RF energy to tissue captured between the clamp arm and the ultrasonic blade.

Example 9

The surgical instrument of any one or more of Examples 1 through 8, wherein the clamp arm further comprises a tissue clamping surface, wherein the tissue clamping surface protrudes beyond the electrode such that the electrode is recessed relative to the tissue clamping surface.

Example 10

A surgical instrument, comprising: (a) a body; (b) an ultrasonic blade extending distally from the body, wherein the ultrasonic blade is operable to apply ultrasonic energy to tissue; and (c) a clamp arm pivotably coupled with the body at a pivot assembly, wherein the clamp arm is operable to compress tissue against the ultrasonic blade, wherein the clamp arm comprises (i) an electrode operable to apply RF energy to tissue, and (ii) a tissue clamping feature, wherein the tissue clamping feature is configured to compress tissue against the ultrasonic blade, wherein the electrode is further configured to secure the position of the tissue clamping feature within the clamp arm.

Example 11

The surgical instrument of Example 10, wherein the tissue clamping feature includes a tissue clamping surface, wherein the tissue clamping surface protrudes beyond the electrode such that the electrode is recessed relative to the tissue clamping surface.

Example 12

The surgical instrument of any one or more of Examples 10 through 11, wherein the tissue clamping feature comprises polytetrafluoroethylene.

Example 13

The surgical instrument of any one or more of Examples 10 through 12, wherein the clamp arm further defines a cavity, wherein at least a portion of the tissue clamping feature is positioned in the cavity.

Example 14

The surgical instrument of any one or more of Examples 10 through 13 in combination with the surgical instrument of any one or more of Examples 1 through 9.

Example 15

A surgical instrument, comprising: (a) a body; (b) an ultrasonic blade extending distally from the body, wherein the ultrasonic blade is operable to apply ultrasonic energy to tissue; (c) a clamp arm pivotably coupled with the body at a pivot assembly, wherein the clamp arm is operable to compress tissue against the ultrasonic blade; and (d) a heat shield, wherein the heat shield is movable toward and away from the ultrasonic blade to thereby selectively shield a portion of the ultrasonic blade.

Example 16

The surgical instrument of Example 15, wherein the heat shield is configured to pivot toward and away from the ultrasonic blade.

Example 17

The surgical instrument of Example 16, wherein the heat shield is pivotable toward and away from the ultrasonic blade along a first plane, wherein the clamp arm is pivotable toward and away from the ultrasonic blade along the first plane.

Example 18

The surgical instrument of any one or more of Examples 15 through 17, wherein the heat shield is configured to approach a first lateral side of the ultrasonic blade, wherein the clamp arm is configured to approach a second lateral side of the ultrasonic blade.

Example 19

The surgical instrument of Example 18, wherein the second lateral side is opposite to the first lateral side.

Example 20

The surgical instrument of any one or more of Examples 15 through 19, wherein at least a portion of the heat shield includes a low friction material.

Example 21

The surgical instrument of Example 20, wherein the low friction material comprises polytetrafluoroethylene.

Example 22

The surgical instrument of any one or more of Examples 15 through 21, wherein the heat shield has a distal end including a protrusion, wherein the protrusion is configured to engage the ultrasonic blade and thereby space a remaining portion of the heat shield away from the ultrasonic blade.

Example 23

The surgical instrument of Example 22, wherein the protrusion comprises a low friction material.

Example 24

The surgical instrument of Example 23, wherein the low friction material comprises polytetrafluoroethylene.

Example 25

The surgical instrument of any one or more of Examples 15 through 24, wherein the heat shield defines a plurality of drainage openings.

Example 26

The surgical instrument of any one or more of Examples 15 through 25 in combination with the surgical instrument of any one or more of Examples 1 through 14.

Example 27

A surgical instrument, comprising: (a) a body, wherein the body includes an electrical conductor, wherein the electrical conductor comprises a coupling post; (b) an ultrasonic blade extending distally from the body, wherein the ultrasonic blade is operable to apply ultrasonic energy to tissue; (c) a clamp arm pivotably coupled with the coupling post, wherein the clamp arm is operable to compress tissue against the ultrasonic blade, wherein the clamp arm comprises an electrode operable to apply RF energy to tissue, wherein the electrode is configured to receive electrical energy through the coupling post.

Example 28

The surgical instrument of Example 27, wherein the coupling post has a T-shape.

Example 29

The surgical instrument of Example 28, wherein the T-shape is configured to enable the clamp arm to me removed from the coupling post when the clamp arm is oriented at a removal angle relative to the body, wherein the T-shape is configured to pivotably secure the clamp arm to the body when the clamp arm is not oriented at the removal angle.

Example 30

The surgical instrument of any one or more of Examples 27 through 29, wherein the clamp arm further comprises a resiliently biased locking feature configured to pivotably secure the clamp arm to the coupling post.

Example 31

The surgical instrument of Example 30, wherein the resiliently biased locking feature is configured to provide a path for electrical communication from the coupling post to the electrode.

Example 32

A surgical instrument, comprising: (a) a body, wherein the body includes a closure sensor; (b) an ultrasonic blade extending distally from the body, wherein the ultrasonic blade is operable to apply ultrasonic energy to tissue; (c) a clamp arm pivotably coupled with the body at a pivot assembly, wherein the clamp arm is operable to compress tissue against the ultrasonic blade, wherein the clamp arm comprises an electrode operable to apply RF energy to tissue, wherein the clamp arm is configured to actuate the closure sensor in response to the clamp arm reaching a predetermined closure angle relative to the body; and (d) a control module in communication with the closure sensor, wherein the control module is operable to select a mode of operation in response to actuation or non-actuation of the closure sensor.

Example 33

The surgical instrument of Example 32, further comprising an activation button, wherein the activation button is positioned to be actuated by an operator, wherein the control module is configured to apply RF energy at a first voltage through the electrode in response to simultaneous actuation of the closure sensor and the activation button.

Example 34

The surgical instrument of Example 33, wherein the control module is further configured to provide a user notification after a sealing algorithm is completed.

Example 35

The surgical instrument of any one or more of Examples 33 through 34, wherein the control module is further configured to provide an error notification to an operator in response to the RF energy being applied for a certain duration prior to notification that the sealing algorithm is complete.

Example 36

The surgical instrument of any one or more of Examples 34 through 35, wherein the control module is configured to apply RF energy through the electrode in response to actuation of the activation button without the closure sensor being actuated.

Example 37

The surgical instrument of any one or more of Examples 34 through 36, wherein the control module is configured to apply RF energy at a second voltage through the electrode in response to actuation of the activation button without the closure sensor being actuated, wherein the second voltage is higher than the first voltage.

Example 38

The surgical instrument of any one or more of Examples 34 through 35, wherein the control module is configured to provide an error indication to an operator, without applying RF energy through the electrode, in response to actuation of the activation button without the closure sensor being actuated.

Example 39

The surgical instrument of any one or more of Examples 33 through 38 in combination with the surgical instrument of any one or more of Examples 1 through 41.

Example 40

A surgical instrument, comprising: (a) a body; (b) an ultrasonic blade extending distally from the body, wherein the ultrasonic blade is operable to apply ultrasonic energy to tissue; (c) a clamp arm pivotably coupled with the body at a pivot assembly, wherein the clamp arm is operable to compress tissue against the ultrasonic blade, wherein the clamp arm comprises an electrode operable to apply RF energy to tissue; (d) a sensor, wherein the sensor is operable to determine whether the ultrasonic blade is engaging tissue;

and (e) a control module in communication with the sensor, wherein the control module is operable to select a mode of operation in response to actuation or non-actuation of the sensor.

Example 41

The surgical instrument of Example 40, wherein the sensor comprises a harmonic impedance sensor.

Example 42

The surgical instrument of any one or more of Examples 40 through 41, further comprising an activation button, wherein the activation button is positioned to be actuated by an operator, wherein the control module is configured to apply RF energy at a first voltage through the electrode in response to actuation of the activation button while the sensor indicates the ultrasonic blade being engaged with tissue.

Example 43

The surgical instrument of Example 42, wherein the control module is further configured to provide a user notification after a sealing algorithm is completed.

Example 44

The surgical instrument of Example 43, wherein the control module is further configured to provide an error notification to an operator in response to the RF energy being applied for a certain duration prior to notification that the sealing algorithm is complete.

Example 45

The surgical instrument of any one or more of Examples 42 through 44, wherein the control module is configured to apply RF energy through the electrode in response to actuation of the activation button without the sensor indicating that the ultrasonic blade is engaged with tissue.

Example 46

The surgical instrument of any one or more of Examples 42 through 45, wherein the control module is further configured to apply RF energy at a second voltage through the electrode in response to actuation of the activation button without the sensor indicating that the ultrasonic blade is engaged with tissue, wherein the second voltage is higher than the first voltage.

Example 47

The surgical instrument of any one or more of Examples 42 through 44, wherein the control module is further configured to provide an error indication to an operator, without applying RF energy through the electrode, in response to actuation of the activation button without the sensor indicating that the ultrasonic blade is engaged with tissue.

Example 48

A surgical instrument, comprising: (a) a body; (b) an ultrasonic blade extending distally from the body, wherein the ultrasonic blade is operable to apply ultrasonic energy to tissue; (c) a clamp arm, wherein the clamp arm is operable to compress tissue against the ultrasonic blade; and (d) a pivot assembly, wherein the clamp arm is pivotably coupled to the body at the pivot assembly, wherein the pivot assembly is configured to provide pivotal movement of the clamp arm relative to the body about a fixed axis as the clamp arm pivots toward the ultrasonic blade through a first range of motion, wherein the pivot assembly is configured to provide a combination of pivotal movement of the clamp arm relative to the body and translational movement of the clamp arm relative to the body as the clamp arm pivots toward the ultrasonic blade through a second range of motion.

Example 49

The surgical instrument of Example 48, wherein the pivot assembly comprises a cam surface having a first cam profile and a second cam profile, wherein the first cam profile is configured to provide pivotal movement of the clamp arm relative to the body about a fixed axis as the clamp arm pivots toward the ultrasonic blade through the first range of motion, wherein the second cam profile is configured to provide a combination of pivotal movement of the clamp arm relative to the body and translational movement of the clamp arm relative to the body as the clamp arm pivots toward the ultrasonic blade through the second range of motion.

Example 50

The surgical instrument of any one or more of Examples 48 through 49, wherein the pivot assembly is configured to provide a combination of pivotal movement of the clamp arm relative to the body and proximal translation of the clamp arm relative to the body as the clamp arm pivots toward the ultrasonic blade through a second range of motion.

Example 51

A surgical instrument, comprising: (a) a body; (b) an ultrasonic blade extending distally from the body, wherein the ultrasonic blade is operable to apply ultrasonic energy to tissue; (c) a clamp arm pivotably coupled with the body at a pivot assembly, wherein the clamp arm is operable to compress tissue against the ultrasonic blade; (d) an acoustic waveguide extending through the body, wherein the ultrasonic blade is located at a distal end of the acoustic waveguide; and (e) a seal interposed between a distal portion of the acoustic waveguide and the body, wherein the seal is configured to cooperate with features of the body to prevent one or both of rotation or translation of the ultrasonic blade relative to the body.

Example 52

The surgical instrument of Example 51, wherein the seal comprises flats, wherein the flats are configured to engage with the features of the body to prevent one or both of rotation or translation of the ultrasonic blade relative to the body.

Example 53

The surgical instrument of any one or more of Examples 51 through 52, wherein the features of the body comprise pins, wherein the pins are oriented transversely in relation to the acoustic waveguide.

Example 54

The surgical instrument of any one or more of Examples 51 through 53, wherein the seal comprises an elastomeric material.

Example 55

A surgical instrument, comprising: (a) a body, wherein the body comprises a plurality of discrete electrical contacts; (b) an ultrasonic blade extending distally from the body, wherein the ultrasonic blade is operable to apply ultrasonic energy to tissue; (c) a clamp arm pivotably coupled with the body at a pivot assembly, wherein the clamp arm is operable to compress tissue against the ultrasonic blade, wherein the clamp arm comprises a plurality of discrete electrical contacts, wherein the discrete electrical contacts of the clamp arm are configured to maintain electrical continuity with the discrete electrical contacts of the body as the clamp arm pivots relative to the body.

Example 56

The surgical instrument of Example 55, wherein either the discrete electrical contacts of the body or the discrete electrical contacts of the clamp arm are spring loaded to maintain contact with the other of the discrete electrical contacts of the body or the discrete electrical contacts of the clamp arm.

Example 57

The surgical instrument of any one or more of Examples 55 through 56, further comprising a seal configured to hermetically seal the discrete electrical contacts of the body and the discrete electrical contacts of the clamp arm.

Example 58

The surgical instrument of any one or more of Examples 55 through 57, wherein the clamp arm further comprises a data feature in communication with the discrete electrical contacts of the clamp arm, wherein the discrete electrical contacts of the body are configured to receive data from the data feature via the discrete electrical contacts of the clamp arm.

Example 59

The surgical instrument of Example 58, wherein the data feature comprises a sensor.

Example 60

The surgical instrument of any one or more of Examples 58 through 59, wherein the data feature comprises an EEPROM.

Example 61

A surgical instrument, comprising: (a) a body; (b) an ultrasonic blade extending distally from the body, wherein the ultrasonic blade is operable to apply ultrasonic energy to tissue, wherein the ultrasonic blade has a tissue engaging surface having a proximal region and a distal region, wherein the proximal region is recessed relative to the distal region; (c) a clamp arm pivotably coupled with the body at a pivot assembly, wherein the clamp arm is operable to compress tissue against the ultrasonic blade, wherein the proximal region of the tissue engaging surface of the ultrasonic blade is configured to ultrasonically sever tissue compressed between the clamp arm and the tissue engaging surface of the ultrasonic blade, wherein the distal region of the tissue engaging surface of the ultrasonic blade is not configured to ultrasonically sever tissue compressed between the clamp arm and the tissue engaging surface of the ultrasonic blade.

Example 62

The surgical instrument of Example 61, wherein the clamp arm comprises an electrode, wherein the electrode is operable to apply RF energy to tissue.

Example 63

The surgical instrument of Example 62, wherein the ultrasonic blade is configured to cooperate with the electrode to apply bipolar RF energy to tissue captured between the tissue engaging surface and the electrode.

Example 64

The surgical instrument of Example 63, wherein the distal region of the tissue engaging surface of the ultrasonic blade is configured to cooperate with the electrode to seal tissue captured between the distal region of the tissue engaging surface of the ultrasonic blade and the electrode with RF energy.

Example 65

A surgical instrument, comprising: (a) a body; (b) an ultrasonic blade extending distally from the body, wherein the ultrasonic blade is operable to apply ultrasonic energy to tissue; and (c) a clamp arm pivotably coupled with the body at a pivot assembly, wherein the clamp arm is operable to compress tissue against the ultrasonic blade, wherein the clamp arm comprises (i) an electrode operable to apply RF energy to tissue, (ii) a tissue clamping feature, wherein the tissue clamping feature is configured to compress tissue against the ultrasonic blade, and (iii) a gap setting feature, wherein the gap setting feature comprises a non-conductive material and is configured to maintain a space between the electrode and the ultrasonic blade when the instrument is in a clamping position.

Example 66

The surgical instrument of Example 65, wherein the electrode is further configured to secure the position of the tissue clamping feature within the clamp arm.

Example 67

The surgical instrument of any one or more of Examples 65 through 66, wherein the gap setting feature comprises a clamp pad bumper.

Example 68

The surgical instrument of Example 67, wherein the clamp pad bumper has a larger surface area per unit length compared to the tissue clamping feature.

Example 69

The surgical instrument of any one or more of Examples 65 through 68, further comprising (d) a first tissue stop feature extending toward the clamp arm; and (e) a second tissue stop feature extending away from the clamp arm, wherein the second tissue stop feature is configured to pivot with the clamp arm, wherein the first and second tissue stop features are configured to restrict passage of tissue to proximal regions of the ultrasonic blade and clamp arm.

Example 70

The surgical instrument of any one or more of Examples 65 through 69, wherein the gap setting feature is positioned proximal to the first and second tissue stops.

Example 71

A surgical instrument, comprising: (a) a body; (b) an ultrasonic blade extending distally from the body, wherein the ultrasonic blade is operable to apply ultrasonic energy to tissue; and (c) a clamp arm pivotably coupled with the body at a pivot assembly, wherein the clamp arm is operable to compress tissue against the ultrasonic blade, wherein the clamp arm comprises (i) a tissue clamping feature, wherein the tissue clamping feature is configured to compress tissue against the ultrasonic blade, and (ii) an electrode operable to apply RF energy to tissue, wherein the electrode is offset relative to the ultrasonic blade.

Example 72

The surgical instrument of Example 71, wherein the electrode comprises a positive offset relative to the ultrasonic blade.

Example 73

The surgical instrument of any one or more of Examples 71 through 72, wherein the electrode comprises an offset of about 0.02 inches.

Example 74

A surgical instrument, comprising: (a) a body; (b) an ultrasonic blade extending distally from the body, wherein the ultrasonic blade is operable to apply ultrasonic energy to tissue, wherein the ultrasonic blade comprises a flat surface configured for ultrasonic cutting and sealing; and (c) a clamp arm pivotably coupled with the body at a pivot assembly, wherein the clamp arm is operable to compress tissue against the ultrasonic blade, wherein the clamp arm comprises an electrode operable to apply RF energy to tissue.

Example 75

A surgical instrument, comprising: (a) a body; (b) an ultrasonic blade extending distally from the body, wherein the ultrasonic blade is operable to apply ultrasonic energy to tissue, wherein the ultrasonic blade comprises a rounded surface configured for ultrasonic cutting and sealing; and (c) a clamp arm pivotably coupled with the body at a pivot assembly, wherein the clamp arm is operable to compress tissue against the ultrasonic blade, wherein the clamp arm comprises an electrode operable to apply RF energy to tissue.

Example 76

A surgical instrument, comprising: (a) a body; (b) an ultrasonic blade extending distally from the body, wherein the ultrasonic blade is operable to apply ultrasonic energy to tissue, wherein the ultrasonic blade comprises an angled surface configured for ultrasonic cutting and sealing; and (c) a clamp arm pivotably coupled with the body at a pivot assembly, wherein the clamp arm is operable to compress tissue against the ultrasonic blade, wherein the clamp arm comprises an electrode operable to apply RF energy to tissue.

Example 77

The surgical instrument of Example 76, wherein the angled surface comprises about a 30 degree angle.

Example 78

The surgical instrument of Example 76, wherein the angled surface comprises about a 15 degree angle.

Example 79

A surgical instrument, comprising: (a) a body; (b) an ultrasonic blade extending distally from the body, wherein the ultrasonic blade is operable to apply ultrasonic energy to tissue, wherein the ultrasonic blade comprises a raised surface surrounded by a flat surface configured for ultrasonic cutting and sealing; and (c) a clamp arm pivotably coupled with the body at a pivot assembly, wherein the clamp arm is operable to compress tissue against the ultrasonic blade, wherein the clamp arm comprises an electrode operable to apply RF energy to tissue.

Example 80

A surgical instrument, comprising: (a) a body, wherein the body includes an electrical conductor, wherein the body defines a longitudinal axis; (b) an ultrasonic blade extending distally from the body, wherein the ultrasonic blade is operable to apply ultrasonic energy to tissue; (c) a clamp arm pivotably coupled with the body at a pivot assembly, wherein the clamp arm is operable to compress tissue against the ultrasonic blade, wherein the clamp arm comprises an electrode operable to apply RF energy to tissue, wherein the clamp arm is configured to be loaded onto and removed from the body at the pivot assembly along a path that is transverse to the longitudinal axis defined by the body; and (d) a resilient member located within the pivot assembly, wherein the resilient member is configured to provide electrical continuity between the electrode of the clamp arm and the electrical conductor of the body.

Example 81

The surgical instrument of Example 80, wherein the ultrasonic blade is configured to cooperate with the electrode to apply bipolar RF energy to tissue captured between the clamp arm and the ultrasonic blade.

Example 82

The surgical instrument of any one or more of Examples 80 through 81, wherein the clamp arm further comprises a tissue clamping surface, wherein the tissue clamping surface protrudes beyond the electrode such that the electrode is recessed relative to the tissue clamping surface.

Example 83

The surgical instrument of any one or more of Examples 80 through 82, further comprising a heat shield, wherein the heat shield is movable toward and away from the ultrasonic blade to thereby selectively shield a portion of the ultrasonic blade, wherein the heat shield is configured to approach a first lateral side of the ultrasonic blade, wherein the clamp arm is configured to approach a second lateral side of the ultrasonic blade.

Example 84

The surgical instrument of any one or more of Examples 80 through 83, wherein the body comprises a plurality of discrete electrical contacts, wherein the clamp arm comprises a plurality of discrete electrical contacts, wherein the discrete electrical contacts of the clamp arm are configured to maintain electrical continuity with the discrete electrical contacts of the body as the clamp arm pivots relative to the body.

Example 85

The surgical instrument of any one or more of Examples 80 through 84, wherein the clamp arm further comprises a data feature in communication with the discrete electrical contacts of the clamp arm, wherein the discrete electrical contacts of the body are configured to receive data from the data feature via the discrete electrical contacts of the clamp arm, wherein the data feature comprises an EEPROM.

Example 86

The surgical instrument of any one or more of Examples 80 through 85, further comprising a control module, wherein the body includes a closure sensor in communication with the control module, wherein the clamp arm is configured to actuate the closure sensor in response to the clamp arm reaching a predetermined closure angle relative to the body, wherein the control module is operable to select a mode of operation in response to actuation or non-actuation of the closure sensor.

Example 87

The surgical instrument of Example 86, further comprising an activation button, wherein the activation button is positioned to be actuated by an operator, wherein the control module is configured to apply RF energy at a first voltage through the electrode in response to simultaneous actuation of the closure sensor and the activation button.

Example 88

The surgical instrument of Example 87, wherein the control module is configured to apply RF energy through the electrode in response to actuation of the activation button without the closure sensor being actuated.

Example 89

The surgical instrument of Example 87, wherein the control module is configured to provide an error indication to an operator, without applying RF energy through the electrode, in response to actuation of the activation button without the closure sensor being actuated.

Example 90

The surgical instrument of any one or more of Examples 86 through 89, wherein the control module is further configured to provide a user notification after a sealing algorithm is completed.

Example 91

The surgical instrument of any one or more of Examples 86 through 90, wherein the control module is further configured to provide an error notification to an operator in response to the RF energy being applied for a certain duration prior to notification that the sealing algorithm is complete.

Example 92

The surgical instrument of any one or more of Examples 86 through 91, wherein the control module is configured to apply RF energy at a second voltage through the electrode in response to actuation of the activation button without the closure sensor being actuated, wherein the second voltage is higher than the first voltage.

Example 93

The surgical instrument of any one or more of Examples 80 through 92, wherein the pivot assembly is configured to provide pivotal movement of the clamp arm relative to the body about a fixed axis as the clamp arm pivots toward the ultrasonic blade through a first range of motion, wherein the pivot assembly is configured to provide a combination of pivotal movement of the clamp arm relative to the body and translational movement of the clamp arm relative to the body as the clamp arm pivots toward the ultrasonic blade through a second range of motion.

Example 94

The surgical instrument of Example 93, wherein the pivot assembly comprises a cam surface having a first cam profile and a second cam profile, wherein the first cam profile is configured to provide pivotal movement of the clamp arm relative to the body about a fixed axis as the clamp arm pivots toward the ultrasonic blade through the first range of motion, wherein the second cam profile is configured to provide a combination of pivotal movement of the clamp arm relative to the body and translational movement of the clamp arm relative to the body as the clamp arm pivots toward the ultrasonic blade through the second range of motion.

Example 95

A surgical instrument, comprising: (a) a body, wherein the body defines a first longitudinal axis wherein the body includes an electrical conductor, wherein the electrical conductor comprises a coupling post, wherein the coupling post defines a second longitudinal axis, wherein the second longitudinal axis is transverse to the first longitudinal axis; (b) an ultrasonic blade extending distally from the body, wherein the ultrasonic blade is operable to apply ultrasonic energy to tissue; and (c) a clamp arm pivotably coupled with the coupling post, wherein the clamp arm is operable to compress tissue against the ultrasonic blade, wherein the clamp arm comprises an electrode operable to apply RF energy to tissue, wherein the electrode is configured to receive electrical energy through the coupling post, wherein the clamp arm is configured to pivot about the second longitudinal axis, wherein the clamp arm is further configured to translate along the second longitudinal axis.

Example 96

The surgical instrument of Example 95, wherein the coupling post has a T-shape, wherein the T-shape is configured to enable the clamp arm to me removed from the coupling post when the clamp arm is oriented at a removal angle relative to the body, wherein the T-shape is configured to pivotably secure the clamp arm to the body when the clamp arm is not oriented at the removal angle.

Example 97

The surgical instrument of Example 95, wherein the clamp arm further comprises a resiliently biased locking feature configured to pivotably secure the clamp arm to the coupling post.

Example 98

The surgical instrument of Example 95, wherein the resiliently biased locking feature is configured to provide a path for electrical communication from the coupling post to the electrode.

Example 99

A surgical instrument, comprising: (a) a body, wherein the body defines a longitudinal axis, wherein the body defines a pivot post; (b) an ultrasonic blade extending distally from the body, wherein the ultrasonic blade is operable to apply ultrasonic energy to tissue; and (c) a clamp arm, wherein the clamp arm defines a pivot opening configured to receive the pivot post, wherein the clamp arm is operable to compress tissue against the ultrasonic blade, wherein the clamp arm comprises an electrode operable to apply RF energy to tissue, wherein the clamp arm is configured to be loaded onto and removed from the pivot post along a path that is transverse to the longitudinal axis defined by the body when the clamp arm is at a first angular orientation relative to the body, wherein the pivot post is configured to pivotably secure the clamp arm to the body when the clamp arm is within a predefined angular orientation range relative to the body that excludes the first angular orientation, wherein the clamp arm is configured to pivot about the pivot post within the predefined angular orientation range.

IV. Miscellaneous

It should be understood that the various teachings herein may be readily combined with the various teachings of U.S. patent application Ser. No. 15/284,837, entitled "Surgical Instrument with Dual Mode End Effector and Compound Lever with Detents," filed Oct. 4, 2016, published as U.S. Pub. No. 2017/0105755 on Apr. 20, 2017, the disclosure of which is incorporated by reference herein. Various suitable ways in which the teachings herein may be combined with the teachings of U.S. patent application Ser. No. 15/284,837, filed on Oct. 4, 2016, published as U.S. Pub. No. 2017/0105755 on Apr. 20, 2017, will be apparent to those of ordinary skill in the art.

It should be understood that the various teachings herein may be readily combined with the various teachings of U.S. patent application Ser. No. 15/284,855, entitled "Surgical Instrument with Dual Mode End Effector and Modular Clamp Arm Assembly," filed on Oct. 4, 2016, issued as U.S. Pat. No. 10,893,914 on Jan. 19, 2021, the disclosure of which is incorporated by reference herein. Various suitable ways in which the teachings herein may be combined with the teachings of U.S. patent application Ser. No. 15/284,855, filed on Oct. 4, 2016, issued as U.S. Pat. No. 10,893,914 on Jan. 19, 2021, will be apparent to those of ordinary skill in the art.

The various instruments described above may be used in a variety of kinds of surgical procedures. By way of example only, the instruments described above may be used to perform liver resection, colorectal surgical procedures, gynecological surgical procedures, and/or various other kinds of surgical procedures. Various other kinds of procedures and ways in which the instruments described above may be used will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body, wherein the body includes an electrical conductor, wherein the body defines a longitudinal axis;
   (b) an ultrasonic blade extending distally from the body, wherein the ultrasonic blade is operable to apply ultrasonic energy to tissue;
   (c) a clamp arm pivotably coupled with the body at a pivot assembly, wherein the clamp arm is operable to compress tissue against the ultrasonic blade, wherein the clamp arm comprises an electrode operable to apply RF energy to tissue, wherein the clamp arm is configured to be loaded onto and removed from the body at the pivot assembly along a path that is entirely transverse to the longitudinal axis defined by the body; and
   (d) a resilient member located within the pivot assembly, wherein the resilient member is configured to provide electrical continuity between the electrode of the clamp arm and the electrical conductor of the body, wherein the resilient member is configured to be resiliently biased and elastically deformable,
   wherein the pivot assembly is configured to provide pivotal movement of the clamp arm relative to the body about a pivot axis, wherein the path is parallel to the pivot axis.

2. The surgical instrument of claim 1, wherein the ultrasonic blade is configured to cooperate with the electrode to apply bipolar RF energy to tissue captured between the clamp arm and the ultrasonic blade.

3. The surgical instrument of claim 1, wherein the clamp arm further comprises a tissue clamping surface, wherein the tissue clamping surface protrudes beyond the electrode such that the electrode is recessed relative to the tissue clamping surface.

4. The surgical instrument of claim 1, further comprising a heat shield, wherein the heat shield is movable toward and away from the ultrasonic blade to thereby selectively shield a portion of the ultrasonic blade, wherein the heat shield is configured to approach a first lateral side of the ultrasonic blade, wherein the clamp arm is configured to approach a second lateral side of the ultrasonic blade.

5. The surgical instrument of claim 1, wherein the body comprises a plurality of discrete electrical contacts, wherein the clamp arm comprises a plurality of discrete electrical contacts, wherein the discrete electrical contacts of the clamp arm are configured to maintain electrical continuity with the discrete electrical contacts of the body as the clamp arm pivots relative to the body.

6. The surgical instrument of claim 5, wherein the clamp arm further comprises a data feature in communication with the discrete electrical contacts of the clamp arm, wherein the discrete electrical contacts of the body are configured to receive data from the data feature via the discrete electrical contacts of the clamp arm, wherein the data feature comprises an EEPROM.

7. The surgical instrument of claim 1, further comprising a control module, wherein the body includes a closure sensor in communication with the control module, wherein the clamp arm is configured to actuate the closure sensor in response to the clamp arm reaching a predetermined closure angle relative to the body, wherein the control module is operable to select a mode of operation in response to actuation or non-actuation of the closure sensor.

8. The surgical instrument of claim 7, further comprising an activation button, wherein the activation button is positioned to be actuated by an operator, wherein the control module is configured to apply RF energy at a first voltage through the electrode in a first mode of operation in response to simultaneous actuation of the closure sensor and the activation button.

9. The surgical instrument of claim 8, wherein the control module is configured to apply RF energy through the electrode in a second mode of operation in response to actuation of the activation button without the closure sensor being actuated.

10. The surgical instrument of claim 8, wherein the control module is configured to provide an error indication to an operator, without applying RF energy through the electrode, in response to actuation of the activation button without the closure sensor being actuated.

11. The surgical instrument of claim 8, wherein the control module is configured to apply RF energy at a second voltage through the electrode in a second mode of operation in response to actuation of the activation button without the closure sensor being actuated, wherein the second voltage is higher than the first voltage.

12. The surgical instrument of claim 7, wherein the control module is further configured to provide a user notification after a sealing algorithm is completed.

13. The surgical instrument of claim 12, wherein the control module is further configured to provide an error notification to an operator in response to RF energy being applied for a certain duration prior to notification that the sealing algorithm is complete.

14. The surgical instrument of claim 1, wherein the pivot assembly is configured to provide pivotal movement of the clamp arm relative to the body about a fixed axis as the clamp arm pivots toward the ultrasonic blade through a first range of motion, wherein the pivot assembly is configured to provide a combination of pivotal movement of the clamp arm relative to the body and translational movement of the clamp arm relative to the body as the clamp arm pivots toward the ultrasonic blade through a second range of motion.

15. The surgical instrument of claim 14, wherein the pivot assembly comprises a cam surface having a first cam profile and a second cam profile, wherein the first cam profile is configured to provide pivotal movement of the clamp arm relative to the body about the fixed axis as the clamp arm pivots toward the ultrasonic blade through the first range of motion, wherein the second cam profile is configured to provide a combination of pivotal movement of the clamp arm relative to the body and translational movement of the clamp arm relative to the body as the clamp arm pivots toward the ultrasonic blade through the second range of motion.

16. A surgical instrument, comprising:
   (a) a body, wherein the body defines a first longitudinal axis, wherein the body includes an electrical conductor, wherein the electrical conductor comprises a coupling post, wherein the coupling post defines a second longitudinal axis, wherein the second longitudinal axis is transverse to the first longitudinal axis;
   (b) an ultrasonic blade extending distally from the body, wherein the ultrasonic blade is operable to apply ultrasonic energy to tissue; and
   (c) a clamp arm pivotably coupled with the coupling post, wherein the clamp arm is operable to compress tissue against the ultrasonic blade, wherein the clamp arm comprises an electrode operable to apply RF energy to tissue, wherein the electrode is configured to receive electrical energy through the coupling post, wherein the clamp arm is configured to pivot about the second longitudinal axis, wherein the clamp arm is further configured to translate along the second longitudinal axis while remaining continuously electrically coupled to the coupling post.

17. The surgical instrument of claim 16, wherein the coupling post has a T-shape, wherein the T-shape is configured to enable the clamp arm to be removed from the coupling post when the clamp arm is oriented at a removal angle relative to the body, wherein the T-shape is configured to pivotably secure the clamp arm to the body when the clamp arm is not oriented at the removal angle.

18. The surgical instrument of claim 16, wherein the clamp arm further comprises a resiliently biased locking feature configured to pivotably secure the clamp arm to the coupling post.

19. A surgical instrument, comprising:
   (a) a body, wherein the body defines a longitudinal axis, wherein the body includes a pivot post defining a pivot post axis transverse to the longitudinal axis;
   (b) an ultrasonic blade extending distally from the body, wherein the ultrasonic blade is operable to apply ultrasonic energy to tissue; and
   (c) a clamp arm, wherein the clamp arm includes a pivot opening configured to receive the pivot post and defining a pivot opening axis, wherein the clamp arm is operable to compress tissue against the ultrasonic blade, wherein the clamp arm comprises an electrode operable to apply RF energy to tissue,
   wherein the clamp arm is configured to be loaded onto and removed from the pivot post along a path that is transverse to the longitudinal axis defined by the body when the clamp arm is at a first angular orientation relative to the body, wherein the clamp arm is removable from the pivot post along the path when the clamp arm is at the first angular orientation with the pivot opening axis aligned with the pivot post axis,
   wherein the pivot post is configured to pivotably secure the clamp arm to the body when the clamp arm is within a predefined angular orientation range relative to the body that excludes the first angular orientation, wherein the clamp arm is irremovable from the pivot post along the path when the clamp arm is within the predefined angular orientation range with the pivot opening axis aligned with the pivot post axis,
   wherein the clamp arm is configured to pivot about the pivot post within the predefined angular orientation range,
   wherein the pivot post is configured to supply electrical energy to the electrode, wherein the clamp arm is further configured to translate along the pivot post while remaining continuously electrically coupled to the pivot post.

20. The surgical instrument of claim 19, wherein the pivot opening axis is configured to remain aligned with the pivot post axis during rotation of the clamp arm between the first angular orientation at which the clamp arm is removable from the pivot post along the path and the predefined angular orientation range within which the clamp arm is irremovable from the pivot post along the path.

* * * * *